United States Patent [19]
Cheung et al.

[11] Patent Number: 5,352,596
[45] Date of Patent: Oct. 4, 1994

[54] PSEUDORABIES VIRUS DELETION MUTANTS INVOLVING THE EPO AND LLT GENES

[75] Inventors: Andrew K. Cheung; Ronald D. Wesley, both of Ames, Iowa

[73] Assignee: The United States of America as represented by the Secretary of Agriculture, Washington, D.C.

[21] Appl. No.: 945,283

[22] Filed: Sep. 11, 1992

[51] Int. Cl.$^5$ .................. A61K 39/245; C12N 7/04
[52] U.S. Cl. .................. 424/205.1; 424/229.1; 424/815; 435/236; 435/235.1; 435/948; 435/172.3; 935/10; 935/12
[58] Field of Search .................. 424/88, 89, 93 T; 435/236

[56] References Cited

U.S. PATENT DOCUMENTS 4,514,497  4/1985  Kit et al. .................. 435/235
4,711,850  12/1987  Kit et al. .................. 435/235

FOREIGN PATENT DOCUMENTS 0141458  5/1985  European Pat. Off. .
WO87/01287  3/1987  PCT Int'l Appl. .

OTHER PUBLICATIONS

Sacks, W. R. 1987 J. Virology 61(3):829–839.
Ellis, R. W. Jn. Vaccines 1988 S. A. Plotkin & E. A. Mortimer Eds. pp. 568–575.
Andrew K. Cheung, "Detection of Pseudorabies Virus Transcripts in Trigeminal Ganglia of Latently Infected Swine," J. Virology 63(7): 2908–2913 (Jul. 1989).
Andrew K. Cheung, "DNA Nucleotide Sequence Analysis of the Immediate-Early Gene of Pseudorabies Virus," Nucleic Acids Research 17(12): 4637–4646 (1989).
Andrew K. Cheung, "The *Bam*HI J Fragment (0.706 to 0.737 Map Units) of Pseudorabies Virus is Transcriptionally Active During Viral Replication," J. Virology 64(3): 977–983 (Mar. 1990).
Andrew K. Cheung, "Cloning of the Latency Gene and the Early Protein O Gene of Pseudorabies Virus," J. Virology 65(10): 5260–5271 (Oct. 1991).
Neal A. DeLuca et al., "Isolation and Characterization of Deletion Mutants of Herpes Simplex Virus Type 1 in the Gene Encoding Immediate-Early Regulatory Protein ICP4," J. Virology 56(2): 558–570 (Nov. 1985).
Weizhong Cai et al., "Herpes Simplex Virus Type 1 ICP0 Regulates Expression of Immediate-Early, Early, and Late Tenes in Productively Infected Cells," J. Virology 66(5): 2904–2915 (May 1992).
Jianxing Chen et al., "Herpes Simplex Viruses with Mutations in the Gene Encoding ICP0 are Defective in Gene Expression," J. Virology 66(5): 2916–2927 (May 1992).

Primary Examiner—Christine M. Nucker
Assistant Examiner—Michael S. Tuscan
Attorney, Agent, or Firm—M. Howard Silverstein; John D. Fado; Curtis P. Ribando

[57] ABSTRACT

An attenuated pseudorabies virus (PRV) having a reduced ability to reactivate from latency is produced by introducing (1) a genomic modification in the early protein 0 (EP0) gene whereby said virus is characterized by the inability to express the early protein 0; or (2) a genomic modification in the large latency transcript (LLT) gene whereby said virus is characterized by disruption of the synthesis of said large latency transcript; or (3) the genomic modifications described in both (1) and (2). The attenuated virus is useful in a vaccine for psuedorabies-susceptible animals, particularly swine. Swine vaccinated with a deletion mutant in the EP0/LLT overlap region displayed reduced virus shedding and fewer clinical signs than animals inoculated with a wild type virus. The deletion mutant-vaccinated swine also harbored less PRV DNA in the nervous tissue and showed reduced ability to reactivate the virus.

19 Claims, 17 Drawing Sheets

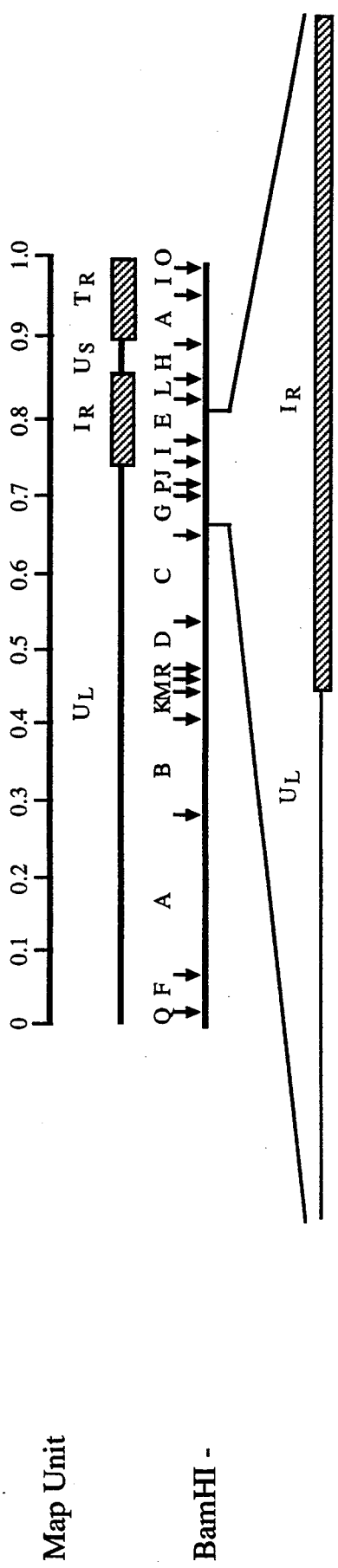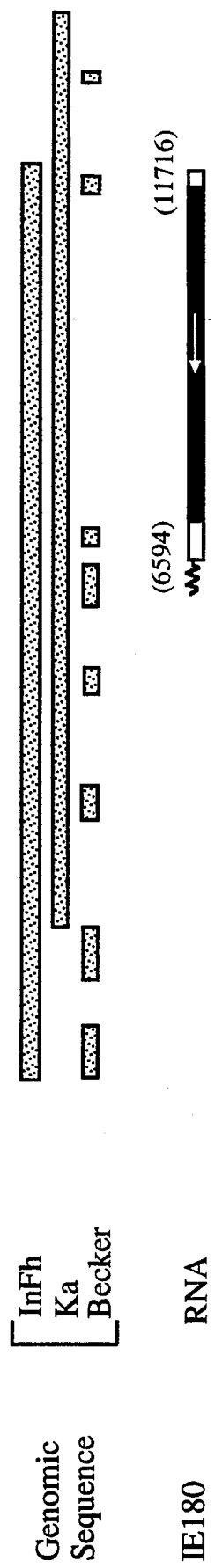
FIG. 1A
FIG. 1B
FIG. 1C

Intron Boundaries

```
                    1511                        6163
                     |                           |
5'  GTC  CAT  GAC  G  GTGAGTGG........CACCGAG  GA  CCA  CCA  TCG  3'
     V    H    D   +                            G    P    P    S
``` cDNA
(Zap 28)

EPO

Location
(InFh Nucleotide)

Poly (A) Site(169)

Poly (A) Signal (195)

Translation Termination (405)

Translation Initiation (1635)

Potential Cap Site (1675)

(1633)

```
                                              *
   1  TATATAATCCCCGGTCCGCGCTCCGCCCACCCATCACAGCAGCCGCGGACGCTG
  55  CGCGCCGGAGCGGTCCATCTCGCCAGCCAGCCAACCAGCCGAGCCGCCCAGCCG
 109  ACCCGAGAGCCCCGAGAGCCAGACTCCCTCAGCCATAGAAGACACCGGGCGGGA
 163  GAGACGGACTGAAAAAATATATCTTTTTTTATTTTGTCTGGGCCTGGAGACCCG
 217  CAGCAGGAGCGGAGGTGGGTGCGGGGCCGGGAGCCGGAGCAGGACCGGGAACAG
                      [aacagg]
 271  GAACAGGAACAGGAACAGGAACAGGAGTGGGGCCGGGAGCAGGAGCAGGAGCGG
 325  GAGCCGAAGTGGGGGCAGGAGCGGCGGCGGCCGCAGCAGCAACAGGGTCGCCCC
 379  AGTCCGCGGCGAGGAAGAGGGAGCTCAGTCGTCGTCCTGGGTGAGGTCGATGAA
 433  GATGGTAGCGGAGCGGGGGGATCCCGACGAGCTAGACGCCGGAGGCCCGCCCCG
 487  GGGGGCGGCGGTCTCGGGGGCAGAGGCAGAGGGCGACGGGCGCCGCATCGAGGA
 541  GGAGGGTGAAGACGAGGGGGAGGAGCGAGCCGAAGCGGCGGTGTTCGCCGACCC 595  CGGGCCGGCCCCGGCCCCCGAGGCACC     ATG CTG CGC AGA GGA CCC CTC GCC GGA
   1                                  M   L   R   R   G   P   L   A   G 649  CGA TGG CGC CTC CGG AGT CTC GCC CTG GGC CTG TCC GCC CGT CCG GCC GCG TCG
  10   R   W   R   L   R   S   L   A   L   G   L   S   A   R   P   A   A   S 703  CAG GCA CCG GGT CCG TCT CTG CTC GCG CCT CAG CAC GGC CGC CCG TCG GGC CCT
  28   Q   A   P   G   P   S   L   L   A   P   Q   H   G   R   P   S   G   P 757  GCG CGG GGA GCG CCT GGG CGC CGG CCT CTG GTC GTC CGC GGA CTC GGA GGC CTC
  46   A   R   G   A   P   G   R   R   P   L   V   V   R   G   L   G   G   L 811  CGT CAG ATC CTC CGT GTG CAC CCC GCT GCT CGA GGC GCC CGA GTC TTC CTC GTC
  64   R   Q   I   L   R   V   H   P   A   A   R   G   A   R   V   F   L   V 865  GGG GGA AGA CAC CTC AGA GTC AGA GTG TGC CTC GGA CTC GGA CGT GTC GAT ATA
  82   G   G   R   H   L   R   V   R   V   C   L   G   L   G   R   V   D   I 919  GTT CAC ACC CTG GTG GCT CAT CGG GGC TCG CCT CTG CAT CCG CCG CAT CCA CTG
 100   V   H   T   L   V   A   H   R   G   S   P   L   H   P   P   H   P   L 973  CGC CGA TAT GTC AAA CAG CGT ATC GAC GAG GGC GTG GGT GTT TGC CCC AAA CAT
 118   R   R   Y   V   K   Q   R   I   D   E   G   V   G   V   C   P   K   H 1027  GGG GAG CAT GGC CTC GGT CAC GCG CTG GCG GTT CAT CCC GTG CTC CTG GAT AAT
 136   G   E   H   G   L   G   H   A   L   A   V   H   P   V   L   L   D   N
                                     g
1081  CTC GAC GAT GTT GTC CAC TAC GGC CTC GCG GAT GGG GTC GCT CTC GAT GAC CGT
 154   L   D   D   V   V   H   Y-D  G   L   A   D   G   V   A   L   D   D   R 1135  CGA GAC CTG CCC ATA AAG CCA GTT GAA GAC GGG GAC TCT GGG GCG GGC GCG AGA
 172   R   D   L   P   I   K   P   V   E   D   G   D   S   G   A   G   A   R 1189  CCC AGA CCC GGA GCC CTG CCC TTC GGC CTC CTC GTG GCG CAC CTC CTC GGT ATA
 190   P   R   P   G   A   L   P   F   G   L   L   V   A   H   L   L   G   I
                                             t
1243  GTC TTC ACC CCA GAT GAC CGC GAA GCC CCC CCC TAC CGG CTC ATC CTC TTC CCC
 208   V   F   T   P   D   D   R   E   A-S  P   P   Y   R   L   I   L   F   P 1297  GTC GAC ATC CGT CGC CCC CTC CAC GGG CGT CTC CAC AAA CGA AGC GTC GCT GTC
 226   V   D   I   R   R   P   L   H   G   R   L   H   K   R   S   V   A   V
```

FIG. 2A(A)

```
                                              c
1351 CAC GTG GTG GAG GAT GGA GGT GAC GCG GGC ATT GCA CAG CGG GCA GGC GGT GCT
244   H   V   V   E   D   G   G   D   A   G  I-L  A   Q   R   A   G   G   A

1405 CGT CAG GGT CCA GCG CTG GAT GCA GTC CAG ACA GAA CTT GTG CAT GCA CGG CAG
262   R   Q   G   P   A   L   D   A   V   Q   T   E   L   V   H   A   R   Q
                                                                          ↓
1459 CGT CTG CGC CTC GGT GGC CGC GAC GTC CAG GCA GAT GGG GCA GTC CAT GAC GGA
280   R   L   R   L   G   G   R   D   V   Q   A   D   G   A   V   H   D   G
                                                                          c
1513 CCA CCA TCG TCT AAC TCC CAC CCG GGA CCA CCG GGA CCC TCG GGA CCA TCT ACA
298   P   P   S   S   N   S   H   P   G   P   P   G   P   S   G   P   S   T
                                                                   ....
1567 TCC CAC CAG GAC CCG CCG GGA CCA CCA ACA CCG TCC ACC TCC CAC CAC CAC CAT
316   S   H   Q   D   P   P   G   P   P   T   P   S   T   S  (H)  H   H   H

1621 CAT CAT CAA GGA CCC CCA ACA TCC CCA AGA CCC TCT ACT TCT TCC CAC CAA GAC
334   H   H   Q   G   P   P   T   S   P   R   P   S   T   S   S   H   Q   D

1675 CCT CCA GGA GGA GGA CCC CCA TCT GCT GAG ACC CAC CAC CAC CAC CAC CAA GAC
352   P   P   G   G   G   P   P   S   A   E   T   H   H   H   H   H   Q   D

1729 CCA CCA GGA GGA GGA CCC CCA TCC ACT TCT TCC CAT CAC CAC CAC CAA GAC CCT
370   P   P   G   G   G   P   P   S   T   S   S   H   H   H   H   Q   D   P

1783 CCA GGA GGA GGA CCC CCG TCA CCC CCA CCA AGA CCC TCC ACC TCT TCT TCT TCC
388   P   G   G   G   P   P   S   P   P   P   R   P   S   T   S   S   S   S

1837 TCC CAC CAG GGA CCC CCA TCC ACA AGA CCA CCT CCA CCC CAG AGA CCA CCG CCA
406   S   H   Q   G   P   P   S   T   R   P   P   P   P   Q   R   P   P   P

1891 AGA TGG CCG CCT CCA TCT CCC CAA AAA ATC TCA GAG ACT CGG GCT GGT TCA GAA
424   R   W   P   P   P   S   P   Q   K   I   S   E   T   R   A   G   S   E

1945 AAT ACA GCA CAA ACT TTA TTT TCT CAC TCT GAA AAT AAA CTC TTT TCT CAC CCG
442   N   T   A   Q   T   L   F   S   H   S   E   N   K   L   F   S   H   P

1999 ATG GGA GAA GGA GGA GAA GGG GAC CGG GGG ACC GCG GGA GGA GAA GGG GAC CGG
460   M   G   E   G   G   E   G   D   R   G   T   A   G   G   E   G   D   R

2053 GAC GAT CCT CGG CCG CCG AGC CCT CCG CCG CGG CCG CCG CCG CCG CTT CCA CCA
478   D   D   P   R   P   P   S   P   P   P   R   P   P   P   P   L   P   P

2107 CCG CCG CCA CCT CCG CCG CCG CCG CAG CCA CCT CCG GCC GGG GGA TCC GCG CGG
496   P   P   P   P   P   P   P   P   Q   P   P   P   A   G   G   S   A   R

2161 AGG AGA AGG AGA GGA GGA GGA GGA GGG CCA CCG GGC CGG GGA GGC AGG CGC CGG
514   R   R   R   R   G   G   G   G   G   P   P   G   R   G   G   R   R   R

2215 GGA GGC AAG CGC CGC CGG GCC GAG GGG ACC GAG GCC GCC GCC GCG GAC GCA GAG
532   G   G   K   R   R   R   A   E   G   T   E   A   A   A   A   D   A   E

2269 GAG GAG GAG GAC GGG GAC GAG GAC GAG GAC GAG GAC CGG GCC GAG GAC GAG GGG
550   E   E   E   D   G   D   E   D   E   D   E   D   R   A   E   D   E   G
```

FIG. 2A(B)

```
2323  AGA GAA GAC GGA GGA GAA GGG CCT CGA GGA GCC GGT GGA GGG GCC GGA GAG TCA
568    R   E   D   G   G   E   G   P   R   G   A   G   G   G   A   G   E   S

2377  GAG TCA GAG TCA GAG TCC AGC CGG GCC GAG GGG GCG CCC CGC TCA GCG GAG CAG
586    E   S   E   S   E   S   S   R   A   E   G   A   P   R   S   A   E   Q

2431  CAG GTA GGG GTT GCC GGC GTC CTC GGC CTC CTC GTC GTC CGA GAT GGC CTC CAC
604    Q   V   G   V   A   G   V   L   G   L   L   V   V   R   D   G   L   H

2485  CTT GAT GGG CCC GAG CGG GCC GCG GGG CCG GCC GTC GCC GCC GCG GAA GCC GAC
622    L   D   G   P   E   R   A   A   G   P   A   V   A   A   A   E   A   D

2539  GAT CTC CAC CGC GGC AGA GTC CTC CCC GTC CTC GCC GGG CCC CCG GGC GCC CGA
640    D   L   H   R   G   R   V   L   P   V   L   A   G   P   P   G   A   R

2593  GGG CCG GTG GGT CTC CAC GGC GCC GCC GGC GGC GGC GCG GAC GCT GGT CTC GAA
658    G   P   V   G   L   H   G   A   A   G   G   G   A   D   A   G   L   E

2647  GGG CGC AAA GTC CCA GCG CAC GGC CGG CGG GGC GCC CGC GGC CGC GAG GGC GCC
676    G   R   K   V   P   A   H   G   R   R   G   A   R   G   R   E   G   A

2701  CGG GGC CAG CAC CAG CGG GGC GGC CTC GGC GTC GGG CTC CAG CAG CGC CGC GGC
694    R   G   Q   H   Q   R   G   G   L   G   V   G   L   Q   Q   R   R   G

2755  GCA GAA GGC GCG CAG CTC GGC CGG CAG GCC CTC GGG GCC GCG GAG CTC GGC GAG
712    A   E   G   A   Q   L   G   R   Q   A   L   G   A   A   E   L   G   E

2809  GCC CCG GCG GCC GCA GGA GAC GAA GAC GGG CCG CAG CGG GGC GCC GAG CCC CCA
730    A   P   A   A   A   G   D   E   D   G   P   Q   R   G   A   E   P   P

2863  GCG GTT GGC CGC GCG GTG CCC GAA GGC GGC GCC CGC GTC AAA GTC CGG GTC CCC
748    A   V   G   R   A   V   P   E   G   G   A   R   V   K   V   R   V   P

2917  GAG CCC GAG CGC GGA GCG CTG GCG GGC CAT GTC CTT GCA GCC GTC CAC GGT GGG
766    E   P   E   R   G   A   L   A   G   H   V   L   A   A   V   H   G   G

2971  GAG CAC GCG CTC GCG GTA GGC GCG CGG CGG CAG CGG GAC CGG GGT CCG GGG CCC
784    E   H   A   L   A   V   G   A   R   R   Q   R   D   R   G   P   G   P

3025  GGC GCG GGT GCT CAC CGT GTA GCG CAC GTT GTC CTG GCG GCA GAG GCG CAG CGG
802    G   A   G   A   H   R   V   A   H   V   V   L   A   A   E   A   Q   R

3079  CTC GGC CCC GGG GTG CAG GCG GGC GAA GGA GGC CTC CAC GCG GGC GAA GCA GGC
820    L   G   P   G   V   Q   A   G   E   G   G   L   H   A   G   E   A   G

3133  CGG GCC CAC GAT GGA GCT CGA GTC CAG GAC GGC CGC GCG GAG CTC GCG GCA CTC
838    R   A   H   D   G   A   R   V   Q   D   G   R   A   E   L   A   A   L

3187  GGG CCA GCG CAC GGC GCA CTG GGC GGC CGG GTC CAG GCG GGC GCG GAC GTA GAC
856    G   P   A   H   G   A   L   G   G   R   V   Q   A   G   A   D   V   D

3241  GTG GTA GTC CCC CAC GGC CGG GCC GTC CGC GGG CCA GTC CTC GAT GGT GTC CAG
874    V   V   V   P   H   G   R   A   V   R   G   P   V   L   D   G   V   Q

3295  CAC GAT GAG CCG GCG CCG CGC CGC GCC GAG CCG CGA GCA GAG GTA CTC GAC GGC
892    H   D   E   P   A   P   R   R   A   E   P   R   A   E   V   L   D   G
```

FIG. 2A(C)

```
3349  GCC GGC GAA GCC GAG GTC CCG CGC CGA GAG CAG CAG CAC CCC CTG GGC GTT GAG
910    A   G   E   A   E   V   P   R   R   E   Q   Q   H   P   L   G   V   E

3403  GCG GCC GAT GTC GGG GCG CCC GGT CCA GTT CCC GGC CCA GGC GTG CGA GTC CGG
928    A   A   D   V   G   A   P   G   P   V   P   G   P   G   V   R   V   R

3457  CGT GCA GAG GCG GTG GGC GAA GGC GGC GAG CAG CGC CGA GAG GCC GCC GCG GCG
946    R   A   E   A   V   G   E   G   G   E   Q   R   R   E   A   A   A   A

3511  CGG GTC CCA GGC CGG GCG CGG GGC GCC CTC GGC GGG CTC GGC GCA GAG CTC CTC
964    R   V   P   G   R   A   R   G   A   L   G   G   L   G   A   E   L   L

3565  GTG GGG CAG CGG GTC GTA GAG CAC CAC CAC GCG CAC GTC CTC GGG GTC GGC TAT
982    V   G   Q   R   V   V   E   H   H   H   A   H   V   L   G   V   G   Y

3619  CTG CCG CAT CCA GGC GGC GCG GCG GCG GAG CGG GGC GCC CGC GGC CCC GCG GCG
1000   L   P   H   P   G   G   A   A   A   E   R   G   A   R   G   P   A   A

3673  CGC GGC GAT GTG CGC CAG GGC GGC CGG GTC GAA GGT GAG CGC CGG GCG CCA GAG
1018   R   G   D   V   R   Q   G   G   R   V   E   G   E   R   R   A   P   E

3727  TTC GGG GAA GAC CTC CTG GTC CAC GAG GGC GCG GGC CAC CTC GGG CGG GCA GTA
1036   F   G   E   D   L   L   V   H   E   G   A   G   H   L   G   R   A   V

3781  GGC GGC GAG GGC CGC GGC GGA GGG CCG CGG CGT GTG GGT CTC GCC GGC CGG GAC
1054   G   G   E   G   R   G   G   G   P   R   R   V   G   L   A   G   R   D

3835  GCG GCG GAA GCC GCC GTC GGG CGC GGG GTG CTC GGG CAT GGG CCC GAG CGG GCG
1072   A   A   E   A   A   V   G   R   G   V   L   G   H   G   P   E   R   A

3889  CCG GAG CCG GTC GTC CTC GGA GGA GGA GGA GGA GGA GGA GGA GGA CAC GAG CGC
1090   P   E   P   V   V   L   G   G   G   G   G   G   G   G   G   H   E   R

3943  GGG AGC GGG GTC CGG AGC GGG CCC GAG TCC GAG GGA GCG GCG CTT GCG CCG GGG
1108   G   S   G   V   R   S   G   P   E   S   E   G   A   A   L   A   P   G

3997  CCC CCG GTC CTC TTC GTC GTC GCG GTG GCC GTG GCC GTC CCC GCG GAG GGC CGA
1126   P   P   V   L   F   V   V   A   V   A   V   A   V   P   A   E   G   R

4051  GCC GGA GAG CCC CTC GTC CTC CTC GCC GTC CCC GGG GCG GCG GGC CCC GGG CGC
1144   A   G   E   P   L   V   L   L   A   V   P   G   A   A   G   P   G   R

4105  GCG GCG CTT CTT CTT GCG CCG CTC GGG CGC TGG GTC CGG GCC GGC GGC GGG GGA
1162   A   A   L   L   L   A   P   L   G   R   W   V   R   A   G   G   G   G

4159  GCT GGC GTA GCC GGA GGA GCC GGA GAG GCC GGA CTT GGT GCC GGA GCT GGA CTT
1180   A   G   V   A   G   G   A   G   E   A   G   L   G   A   G   A   G   L

4213  GGT GCT GGA GCC GGA CTT GGT GCT GGC GGG GCT GGA GGG CCC GGA GCC GGG GAG
1198   G   A   G   A   G   L   G   A   G   G   A   G   G   P   G   A   G   E

4267  GCC GGA GGG GGC GCC CGC CGC CGC CGG CGC CGG CGC TGG GAC GAC GAG GCC GGG
1216   A   G   G   G   A   R   R   R   R   R   R   R   W   D   D   E   A   G
```

FIG. 2A(D)

```
4321  CTG CTC GGG CCA GAG CGG GGG CAG GCC GGG CGC GGG CTC CGC GGG CCC GGG CCG
1234   L   L   G   P   E   R   G   Q   A   G   R   G   L   R   G   P   G   P

4375  CGC GGC GGC CTC GGC GAG CCG GGC CCC GGC CAC GTT GGC CGG GGC GAA GAG GGC
1252   R   G   G   L   G   E   P   G   P   G   H   V   G   R   G   E   E   G

4429  CGC GGC GTA GGT CCA GGC GGC CTC GCG GGC GCG GGC CCC GTC CAC GCT GTA GCG
1270   R   G   V   G   P   G   G   L   A   G   A   G   P   V   H   A   V   A

4483  CAC CAG CGG CGC CAC GGT GCG GGC GAC GAG GGC GAC AGA GTC CGC GGC CTG CTG
1288   H   Q   R   R   H   G   A   G   D   E   G   D   R   V   R   G   L   L

4537  CCG CTC GGC CGG GCC GGC CCC GGG GAT CGC GTC GCG GAG CGC GAG CAG CGC GGC
1306   P   L   G   R   A   G   P   G   D   R   V   A   E   R   E   Q   R   G

4591  GGT CAC CTC CTC GAG GCA GGC GGG CCC GAG GGC GGC CGG GGC GCG GGC GGG CGC
1324   G   H   L   L   E   A   G   G   P   E   G   G   R   G   A   G   G   R

4645  GGG CAG CCG GAG CGG GCA GGG CAG CAG GCG CTC GAG GAC GCC GCG GCA GGC CAG
1342   G   Q   P   E   R   A   G   Q   Q   A   L   E   D   A   A   A   G   Q

4699  GAC GCA GGC GTC CGC CAG CTC GCG GGG CAC GCG GCC GGG CTG CGC GGC GGC GAA
1360   D   A   G   V   R   Q   L   A   G   H   A   A   G   L   R   G   G   E

4753  GGC GGC GCG GAC GCG GGC GCA GAG GGC CTC GAC GGT CGC CTC CCC GGC GCG GGG
1378   G   G   A   D   A   G   A   E   G   L   D   G   R   L   P   G   A   G

4807  GTC CGC GGC GCG GCC CGG GTA GGC CAT GTC GGC GTA GGC CCG GCG GAG GCT CTG
1396   V   R   G   A   A   R   V   G   H   V   G   V   G   P   A   E   A   L

4861  CAG GAT GAA GGT CTT CTG GGT GCG ATC GTA GCG GCG GCT CAT GGC CAC GGC GCT
1414   Q   D   E   G   L   L   G   A   I   V   A   A   A   H   G   H   G   A

4915  CAC CGC GTG CGG CAG GGC CCA GAG CGG GTC CTG GGC GGC CAT GGC GTC CCC GAT
1432   H   R   V   R   Q   G   P   E   R   V   L   G   G   H   G   V   P   D

4969  GTG CGG CAG CGG CGG GGT CAC GCT GCC GGT GAT GAA GGA GCC GTG GCC GTG GGG
1450   V   R   Q   R   R   G   H   A   A   G   D   E   G   A   V   A   V   G

5023  CGC GTG GAC CCG GCG CTG GCA GAA CTG GTT GAA GCG CTG GTC GGG GGC CTG CAT
1468   R   V   D   P   A   L   A   E   L   V   E   A   L   V   G   G   L   H

5077  CCG CGG GTT CTG CAG CCA GGA CAT GGC CTC GCC GGC GGC CCC GCT GTA GAT GAG
1486   P   R   V   L   Q   P   G   H   G   L   A   G   G   P   A   V   D   E

5131  GCG CAC GAG GGC CTC GTG CTG CTT CCT CGA GTC CCC CAT CTC CGG GAT GAA GAC
1504   A   H   E   G   L   V   L   L   P   R   V   P   H   L   R   D   E   D

5185  GGG CAC GGG CCC GGC CGC GGC GCG GTA GCG GGC CGC GGC CTG GCG GAC GTC GTC
1522   G   H   G   P   G   R   G   A   V   A   G   R   G   L   A   D   V   V

5239  CTC GTC CCA GAG CCC CTC GCG GGA GTC CCC GGC GCC GCC GTA GCG GAC GCG GCC
1540   L   V   P   E   P   L   A   G   V   P   G   A   A   V   A   D   A   A
```

FIG. 2B(A)

```
5293  GTC GGC CGG AGG GTC GGA GCC GGG CCA GGG CTC CCC GAG CGG GGT GAG CAG CGG
1558   V   G   R   R   V   G   A   G   P   G   L   P   E   R   G   E   Q   R

5347  CCC GTC GGT CGG CGG GGG CCC GTC GGC CAT GAG CGA GAG GTG GTT GTT GGT GGA
1576   P   V   G   R   R   G   P   V   G   H   E   R   E   V   V   V   G   G

5401  GCG GCG CTT CCT GCG CGG GGG CCG GGC GGG CTC CGG GGC CGG GGC CGG GGA GGC
1594   A   A   L   P   A   R   G   P   G   G   L   R   G   R   G   R   G   G

5455  CGC GGC GGA GGA GGA GGT GGC GGA GGC GGA GGA GGC CGA GGG CCG CGG GGC CGC
1812   R   G   G   G   G   G   G   G   G   G   G   G   R   G   P   R   G   R

5509  GGC GGG CGC CGG CGG AGA CGG TGG CGG CCC GGC GCG GGC GAG TGG GGC GCC GGG
1630   G   G   R   R   R   R   R   W   R   P   G   A   G   E   W   G   A   G

5563  CCG GAC TCC TTC GTC TTC TTC TCC CTC GGA GGA GGA CGA GGA CGA GGA GGA CGA
1648   P   D   S   F   V   F   F   S   L   G   G   G   R   G   R   G   G   R

5617  GGA GGA CGA GGA CGA GGA GGA GGC CGA GCG CCG CGC GGC GGC GGC GGC GGC GGC
1666   G   G   R   G   R   G   G   G   R   A   P   R   G   G   G   G   G   G

5671  GGG GGC CCG GGG GGC GGA GGG CGA GCG GGC CGG GGA GAG GTC CGA GTC GCT GCC
1684   G   G   P   G   G   G   G   R   A   G   R   G   E   V   R   V   A   A

5725  GCC GCT GCT GGA GCT GCT GAA GCC GCG GCC GCG GCG GAG GGC GCC CTC TCC GGC
1702   A   A   A   G   A   A   E   A   A   A   A   A   E   G   A   L   S   G

5779  GCG GCG CCG GCG GGG CTG TCT CTG CAG GGG CGC CCC GCC GTC CCC GGC GAG GCC
1720   A   A   P   A   G   L   S   L   Q   G   R   P   A   V   P   G   E   A

5833  GAG TCC GTC CTC GTC CTT CTC GGG GCC GCG GGC GAC GGG CTC GAC GGC GAC GGT
1738   E   S   V   L   V   L   L   G   A   A   G   D   G   L   D   G   D   G

5887  GGT GGT GGA GCT GGA GCT GGA GTT GGG GTT GGA GGA GAC GGG GCT CCG GGC GCC
1756   G   G   G   A   G   A   G   V   G   V   G   G   D   G   A   P   G   A

5941  AAG CGG CCG AGG ATC GAG CCG CCT CGC GGC GGC GGG CTC GTC GAG CAG GGG CTC
1774   K   R   P   R   I   E   P   P   R   G   G   G   L   V   E   Q   G   L

5995  GCG GTG CTG GTG ATG GTG ACG ACC GCG GTC CCC TCC GCC GGA GGG GGC GCC GCC
1792   A   V   L   V   M   V   T   T   A   V   P   S   A   G   G   G   A   A

6049  GCC GCC GGG CGC CGA GAC CGG CCC GGC GGC GGG GGA GGC TGG GGA AGC GGG CCC
1810   A   A   G   R   R   D   R   P   G   G   G   G   G   W   G   S   G   P

6103  CCG CCG TGC CGG CGC TGC GGC CAC CGC TGC TGG CTG TGC TGG TGG CGC CGG GGT
1828   P   P   C   R   R   C   G   H   R   C   W   L   C   W   W   R   R   G

6157  CCG AGG CCG CGC CGC CGG CCC GGG CTC ACC GAC CGG GTC CCC CCT CGC GGG GGA
1846   P   R   P   R   R   R   P   G   L   T   D   R   V   P   P   R   G   G

6211  CCA TCT CCG CGG GGC CGC CGA GGG GCC GGG GGA GCC GGA GGA GCC GGA GGA GCC
1864   P   S   P   R   G   R   R   G   A   G   G   A   G   G   A
```

FIG. 2B(B)

```
6265 GGA GGA GGA GGA GGC CGG GGA GGC TGC GGA GGG GGA CGA GCG CCC GGG GCC GCC
1882  G   G   G   G   G   R   G   G   C   G   G   G   R   A   P   G   A   A

6319 GGG GGC CCC GGC CTC TGC CGC TGC GAG TGC TGC CGG GGT CGG CGG CCG GGG CCC
1900  G   G   P   G   L   C   R   C   E   C   C   R   G   R   R   P   G   P

6373 GGA GCC GGC CCG GGA CCG GGG CCC GAG GAC GAG GTG ACC GTG CTC GGA GCC CTG
1918  G   A   G   P   G   P   G   P   E   D   E   V   T   V   L   G   A   L

6427 ATG GAG AGC CCG ACC GGG GGA CCC GGC GGC CGG GGA CCC GGG CTC GTC CTC CTC
1936  M   E   S   P   T   G   G   P   G   G   R   G   P   G   L   V   L   L

6481 CTC GTC TTC GTC GTC TAG          CACCACGATCTCGCCCGAGCCCCGGCGGGCGTGCCG
1954  L   V   F   V   V   *
```
```
                                            g
6535 CTGCTGCTGGGCCGAAGGAGGACGGGGCGGCCTCGTGGCTCCGGCCGCGGCCGC
6589 GAGGACGGCGGCCTCGGCCTCGGCGGCGTCGTCGGAGAAGAGGCCGCCCGGGCC
6643 GAAGAGGAGATCCTCGCCGGAGGAGCCGCGGCGCCGGGAGCCCTGGCTGCCGCC
6697 GTCGGGGCCGGACGCGATGCCCTCTTCCTCGGCCGCGGCGGCGGCGGCCGCCAG
6751 GAGCTGGCTGAAGTTGCCCTCGGTCTCGATGAAGTCAAAGAGATCGTCGGCCAT
6805 GGTCTCGATCGGGGTCTTTCTGCCTGAGCGAGGCCGGGCGCCGAGCGCGGAGAG
6859 CGGGCGGCGGAGAAGAAGGAGGAAGGCGGCCGGAGGAGGAGAAGAAGACTCTTC
6913 TCTGGTGGGCCGAGAGCCTCTGTGGGTCGGGCGTCCGTCGAGGGCTGATAGCCG
                                                   g
6967 CCGGAGAGCCGGAGTCTTCAGAGTCCGCGCCGGAGCGGAGACGATCGGATCCCC
7021 TCGGGTTGGCAGAGAACGATGCTGTCCGTACCTGCACCGCAGTGAAGTGCTACG
7075 ATGGAGACCGCGCTTATAAGCGCCCCGAGGAGAGCCCGCCCCCAGGTAAGCGGA
7129 CCAATGGCCGATTTTCGCCGCGGACTTCCCCGACGGCCGGCCAATGGGATTTTT
7183 CTCGCCCGCTTCCTCTCGCGTCTGCTTTGCATGCCCGGCCCAAGATGGCGGCCG
7237 CCGGCCAATGGGATTTCGCGAGGAACTTCCTCGCGAGGACCATTTGCATGCCCG
7291 GCCCCGCGGCGGCCATCTTGCCCACTCGACGGCCAATGGGATTTCTCTCGCCC
7345 ACTTCCTCTCGCGTCTACTTTGCATGTCCGGCCCCGAGGGCGCCATCTTGGCCC
7399 CTCGACGGCCAATGGGATTTCTCTCCCTACTTCCTCTCGCGTCTACTTTGCATG
7453 TCCGGCCCCGCGGCGGCCATCTCGGCTCGCCCGGGCCAATGGGCGCGCGGAGG
7507 CGTCTCCCGCGCGCCTCTGATTTGCATGCCCGGCCCGCTCTGCGGCCATCTTGG
7561 CCGCGGGCGGCCAATGAGATTGTCCGAAAATCCCTCGCGCGGGCGCGAGGCGCA
7615 TGCTCGGCACGCGACCCACCCCGTGGTGCTAGCGAGCCAATCAGATGATTTTC
7669 GGGGAAGCTTCCGTGTGCACGTCATTTGCATGCTCGCCCCACGTGGCCGCCCTC
7723 GGCCAATGGGGCCTCACGGTGCAAGCTTCCGTGTGTCTGCACGTGGTCCGCATG
7777 TGTTGTGGTGGTCTCTGTGTTGTGTGGTGGTCTCTGTGTTGTGTGGTGGTCTCT
7831 GTGTTGTGTGGTGGTCTCTGTGTTGTGTGGTGGTCTCTGTGTTGTGTGGTGGTC
7885 TCTGTGTTGTGTGGTGGTCTCTGTGTTGTGTGGTGGTCTCTGTGTTGTGTGGTG
7939 GTCTCTGTGTTGTGTGGTGGTCTCTGTGTTGTGTGGTGGTATCACCGCCTCCCC
7993 CTGCCACTCGCGAGACCCCGAGACCCCCGTTTCCCCCTCCTCGAGACCCCTGAG
8047 ACCCCCGAGACCCTCCCGCGACCCCCGCGGTCGCCCCACCCGCGCCTCGCGCTC
8101 GGCGCGCGCTCCGAGGGCGCCCCAGCCGGTCGGAGAGACGAGCGGAACCGCCGT
8155 CGGACCGGGGACCGGCGACCGGACCCGAACCGGGAAGCGACGCCGGGGCGGGAG
8209 AACCGGACCCGAACCTCGAGCCCGGACCCGCCCGGACCCGGAAGGAAGGAGCCG
8263 GACAGCCACGCCTTGGATACTTTTGTCGCCCACCCACCCCCTCCTCTCCCCCAC
8317 CCCTCTATCTCTCTCTCCCGGTCCCCCCTCCCACCCCACGAGACACGCCCCAGA
         ...                                *
8371 GTG(AAA)AAAAAAATAAAAGTTGTTCTCGTTGCACCGTCTTCCGGCTCGTGTCGT
8425 CCTTCCGCGGTACC
```

FIG. 2B(C)

```
  1  GGATCCGCAGCGCCGCGCTTTCAGACCCAGGAGCCGTCGACCCACCGCGGAGGGC
 55  CCGCTTCCCACGACGGCGCGCCATCGTCCCGGGACGCCCGAGGGGGC
109  GGGGGAGCCCCGACGCCCGGGGCGGGGGCGTGGACGCCCCGGGCGAAGA

163  CAAACAAAGGGGCCGGGCACCCGGTTAAAAACGGGGCCCTCGACACC    ATG GGC
  1                                                   M   G

217  TGC ACG GTC TCT CGG AGA CGG ACG ACC ACC GCC GAG GCT TCC AGC GCC TGG GGG
  3   C   T   V   S   R   R   R   T   T   T   A   E   A   S   S   A   W   G

271  ATC TTT GGC TTC TAC CGC CCC AGA AGC CCC TCG CCA CCG CCG CAG CGC CTG TCA
 21   I   F   G   F   Y   R   P   R   S   P   S   P   P   P   Q   R   L   S

325  CTG CCA CTC ACC GTC ATG GAC TGC CCC ATC TGC CTG GAC GTC GCG GCC ACC GAG
 39   L   P   L   T   V   M   D   C   P   I   C   L   D   V   A   A   T   E

379  GCG CAG ACG CTG CCG TGC ATG CAC TTC TGT CTG GAC TGC ATC CAG CGC TGG
 57   A   Q   T   L   P   C   M   H   K   F   C   L   D   C   I   Q   R   W

433  ACC CTG ACG AGC ACC GCC TGC CCG CTG TGC AAG GCC CGC GTC ACC TCC ATC CTC
 75   T   L   T   S   T   A   C   P   L   C   K   A   R   V   T   S   I   L

487  CAC CAC GTG GAC GGT TCG TTT GTG GAG ACG CCC CGT GAG GCG ACG
 93   H   H   V   D   A   S   F   V   E   T   P   V   E   G   A   T

541  GAT GTC GAC GGG GAA GAG GAT GAG CCG GGG GGA TTC GCG GGG TGG
111   D   V   D   G   E   E   D   E   P   V   G   G   F   A   G   I   W

595  GGT GAA GAC TAT ACC GAG GTG CGC CAC GAG GCC TTC AAC CAG GGG TCC
129   G   E   D   Y   T   E   V   R   H   E   A   E   F   N   Q   G   S

649  GGG TCT CGC GCC CCC AGA GTC CCC GTC TTC CTT TAT GGG
147   G   S   G   S   R   A   P   R   V   P   V   F   N   W   L   Y   G

703  CAG GTC ACG TCG ATC ATC CAG CAG AGC CAC GGG ATG CGC GAG CGC GTG GAC AAC
165   Q   V   T   S   I   I   Q   E   S   H   G   M   R   E   A   V   D   N

757  ATC GTC GAG ATT ATC CAG CAG GAG CAC CAC GGG ATG AAC CGC CAG CGC GTG ACC GAG GCC
183   I   V   E   I   I   Q   E   H   G   M   N   R   Q   R   V   T   E   A
```

FIG. 3A

```
811   ATG CTC CCC ATG TTT GGG GCA AAC ACC CAC GCC CTC GTC GAT ACG CTG TTT GAC
201    M   L   P   M   F   G   A   N   T   H   A   L   V   D   T   L   F   D

865   ATA TCG GCG CAG TGG CGG CGG ATG CAG AGG CGA GCC CCG ATG AGC CAC CAG
219    I   S   A   Q   W   R   R   M   Q   R   R   A   P   M   S   H   Q

919   GGT GTG AAC TAT ATC GAC GAG TCC GAG ACG GCA TCC GAG CAC TCT GAG GTG
237    G   V   N   Y   I   D   E   S   E   T   A   S   E   H   S   E   V

973   TCT TCC CCC GAC GAG GAA GAC TCG GGC GCC AGC TCG GGG CAC ACG GAG
255    S   S   P   D   E   E   D   S   G   A   S   S   G   V   H   T   E

1027  GAT CTG ACG GAG GCC TCC GAG GAC TCC GCG GAC CCG GCG CCC AGG CGC
273    D   L   T   E   A   S   E   D   S   A   D   Q   R   P   A   R   R

1081  TCC CCG CGC AGG GCC CGA CGG GTG CTG AGG CGC GAG CAG CGC CGG AGA ACC
291    S   P   R   R   A   R   R   A   V   L   R   R   E   Q   R   R   T

1135  CGG TGC CTG CGA CGC GGC CGG ACG GGA CAG CAG GCC GAG ACT CCG GAG
309    R   C   L   R   R   G   R   T   G   G   Q   Q   A   E   T   P   E

1189  GCG CCA TCG TCC GGG GAG TCC TCT GCG CAG CAT GGT GCC TCG GGG GCC GGG
327    A   P   S   S   G   E   S   S   A   Q   H   G   A   S   G   A   G

1243  GCC GGC CCG GGG TCG GCG AAC ACC GCC GCT TCG GCT CGC TCC CCC TCG TCT
345    A   G   P   G   S   A   N   T   A   A   S   A   R   S   P   S

1297  TCA CCC TCC TCC TCG ATG CGG CGC CCG TCG CCC CCC TCT GCC CCC GAG ACC
363    S   P   S   S   S   M   R   R   P   S   P   S   A   P   E   T

1351  GCC GCC CCC CGG GGC GGG CCT CCG GCG TCT AGC TCG TCG GGA TCC CCC CGC TCC
381    A   A   P   R   G   G   P   P   A   S   S   S   G   S   P   R   S

1405  GCT ACC ATC TTC ATC GAC CTC ACC CAG CAG GAC GAC TGA                GCTCCCTCTTCCTCG
399    A   T   I   F   I   D   L   T   Q   Q   D   D   D   *

1459  CCGCGGACTGGGGCGACCCTGTTGCTGCTGCTGCCGCCGCTCCTGCCCCCA
1513  CTTCGGCTCCCGCTCCTGCTCCTCCCGGCCCCACTCCTCTGTTCCTGTTCCTG
1567  TTCCTGTTCCTGTTCCTGTTCCCGTGCTCCTGGTCCTCCGGCTCCCGGCCACCCA
1621  CCTTCCGCTCCTGCTGCTGCGGGTCTCCAGGCCCAGCCCCAGACAAATAAAAAGATATATT
1675  TTTTCAGTC
```

FIG. 3B

```
EPO   41  LTVMDCPICLDVAATEAQ--TLPCMHKFCLDCIQRWTLTSTACPLCKARVTSILHHVDSDASFVETPVE  101
              *  **          * ****  **   *     ****  *    ****  **
ICPO 111  DEGDVCAVCTDEIAPHLRCDTFPCMHRFCIPCMKTWMQLRNTCPLCNAKLVYLIVGVTPSGSFSTIPIV 171

EPO   41  LTVMDCPICLDVAATEAQTLPCMHKFCLDCIQRWTLTSTACPLCKARVTSILHHVDSDASFVETPVE   101
              *  **         * * * ** **  **   *     ****  *  ****   * *
EPO   61  ASDNTCTICMSTVSDLGKTMPCLHDFCFVCIRAWTSTSVQCPLCRCPVQSILHKIVSDTSYKEYEVH   64
      14                       24                 44                      64
```

FIG. 4

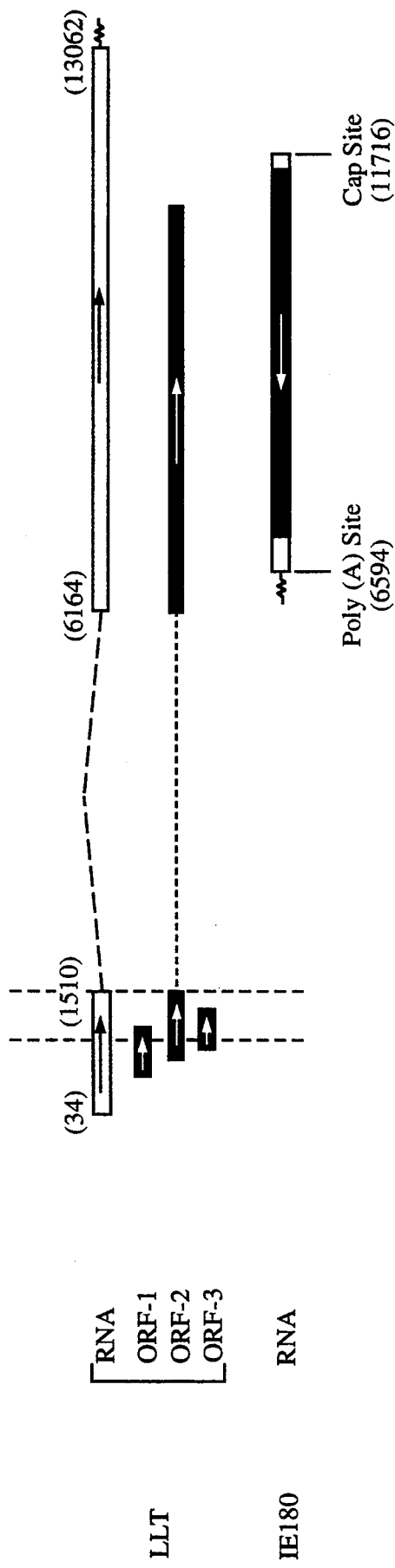
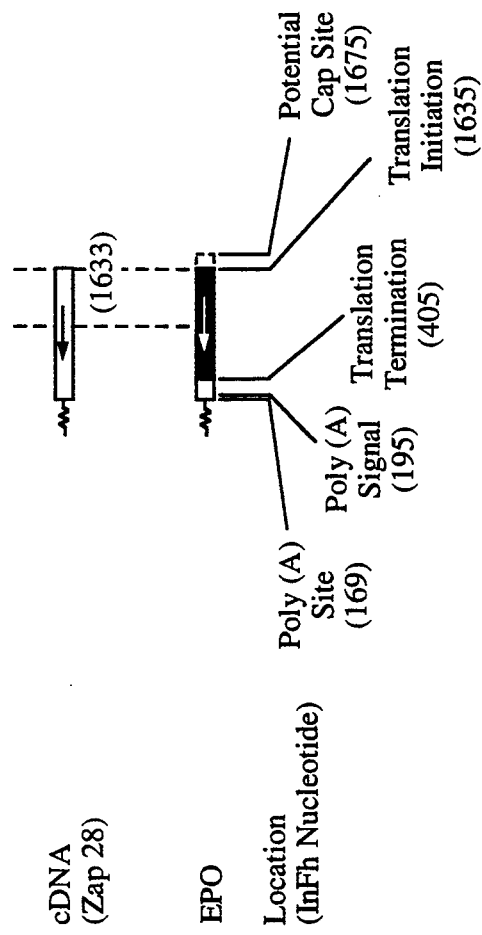
FIG. 5B
FIG. 5C

PSEUDORABIES VIRUS DELETION MUTANTS INVOLVING THE EPO AND LLT GENES

BACKGROUND OF THE INVENTION

1. Field of the Invention

Pseudorabies (Aujeszky's disease) is caused by a herpesvirus belonging to the alphaherpesvirus subfamily. It is a contagious and sometimes fatal disease of swine. Infection during gestation can result in fetal death and abortion. It is estimated that annual losses to the swine industry due to pseudorabies is as high as 60 million dollars in the United States. This economic impact has resulted in a decision by the swine industry and regulatory officials to eradicate the pseudorabies virus (PRV). The virus also infects cattle, sheep, canines, and felines.

During the initial phase of the acute disease, PRV replicates in the upper respiratory tract. Virus can then disseminate by vascular, lymphoid and nervous tissues [D. P. Gustafson, In Diseases of Swine, ed. by A. D. Leman, et al., 6th edition, pp. 274-289, Iowa State University Press, Ames, IA]. Infectious virus and/or viral genome can be detected from lung, tonsil, brain stem, trigeminal ganglia and peripheral blood lymphocytes [F. Wang et al., J. Leukocyte Biol. 43: 256-264 (1988); G. Wittmann et al., Arch. Virol. 66: 227-240 (1980); H. J. Rhiza In Latent Herpes Virus Infections in Veterinary Medicine, ed. by G. Wittman et al., Martinus Nijhoff publishers, The Hague pp. 429-444 (1984); H. J. Rhiza et al., In Proc. 14th International Herpes Workshop, Nyborg, Denmark, p. 55 (1989)]. Clinical symptoms include intense pruritis, violent excitement, fits, paralysis, and eventually death. Upon cessation of clinical signs and recovery from infection, the virus is not eliminated from the animal and persists with the animal indefinitely. Sometimes, the infection is subclinical and goes unnoticed. The animal also becomes a carrier of pseudorabies. In either case, the virus exists in various cell types of the animal in a noninfectious form and is commonly known as a latent infection. The complete viral genome is present but fails to replicate fully to produce infectious virus. The latent virus can reactivate spontaneously or be induced to reactivate by exogenous stimuli, the carrier animal disseminates infectious virus to susceptible animals which may result in death of the animal or establishment of new PRV carriers. Thus, the latent virus is the source and reservoir of the disease and is regarded as an obstacle to the successful control and eradication of PRV.

This invention relates to a PRV deletion mutant vaccine characterized by a high degree of immunogenicity and yet a significant attenuation and reduced level of latency as compared to field strains of the virus.

2. Description of the Prior Art

A. The PRY Genome and Transcription Products

The PRV genome is a linear, duplex DNA molecule with a molecular weight of approximately $90 \times 10^6$ [T. Ben-Porat et al., "Molecular Biology of Pseudorabies Virus," In B. Roizman (ed.), The Herpesviruses, Vol. 3, Plenum Publishing Corporation, NY, pp. 105-173 (1985)]. The genome is organized into the unique long ($U_L$), internal repeat ($I_R$), unique short ($U_S$), and terminal repeat ($T_R$) sequences.

It is estimated that the genetic material is capable of coding for 50 to 100 viral genes. The transcription pattern of PRV in infected cells is extremely complex; however, the genes are expressed in a coordinated, and temporally regulated manner [L. T. Feldman et al., Virology 116: 250-263 (1982); Virology 97: 316-327 (1979); S. Ihara et al., Virology 131: 437-454 (1983); and T. Rakusanova et al., Virology 46: 877-889 (1971)]. In general, herpesvirus genes are categorized into three classes: immediate-early (IE), early, and late genes. The IE genes are transcribed immediately upon infection and do not require de novo protein synthesis. Transcription of early genes depends on IE protein expression and occurs before viral DNA replication. The late genes are transcribed after the onset of viral protein and DNA synthesis.

During herpesvirus latency, a restricted region of the viral genome is transcriptionally active. RNAs denoted as latency-associated transcripts (LATs) are detectable in animals latently infected with the virus [Stevens et al., Science 235: 1056-1059 (1987)]. For pseudorabies virus, the LATs are located downstream of the immediate-early (IE180) gene and in the antiparallel orientation. Since the pseudorabies LATs are the only genetic elements present during latency, it is expected that they play a role in the establishment, maintenance and/or reactivation of the latent virus.

PRV is similar in genomic structure and function to herpes simplex virus type 1 (HSV-1), which is also an alphaherpesvirinae.

On the one hand, many gene homologs have been reported between the two viruses; on the other hand, some genes present in HSV-1 are not present in PRV. There are five HSV-1 immediate-early genes (infected cell polypeptide 0 [ICP0], ICP4, ICP22, ICP27, and ICP47) and only one PRV immediate-early gene (IE180). Analysis of the DNA and deduced amino acid sequences showed that HSV-1 ICP4 and PRV IE180 share extensive homology at two specific regions of the polypeptide [A. K. Cheung, Nucleic Acids Res. 17: 4637-4646 (1989); Cheung et al., Virus Genes,4: 261-265 (1990); Vicek et al., Virus Genes, 2: 335-346 (1989)]. Biologically, these two viruses also exhibit many common characteristics, one of which is their ability to establish latency in their respective hosts.

The HSV-1 LATs, 2 kb or less, are transcribed in the opposite sense with respect to ICP0, and they overlap the 3' end of the ICP0 mRNA. They are not polyadenylated at the 3' end, and a protein product encoded by the LATs has not been identified. Recent reports suggested that there may be a polyadenylated 8.5-kb LAT [Dokson et al., J. Virol., 63: 3844-3851 (1989); Zwaagstra et al., Virus Genes, 64: 5019-5028 (1990)]; however, the exact nature of this transcript has not been fully elucidated. This RNA, designated the large latency transcript (LLT), has been proposed to overlap the entire ICP0 in the opposite orientation but does not overlap ICP4. It has been suggested that the LATs are stable introns derived from the 8.5-kb LLT.

The LATs of PRV were first localized to the 3' end of the immediate-early gene IE180 [A. K. Cheung, J. Virol., 63: 2908-2913 (1989)], a homolog of HSV-1 (ICP4 and not ICP0). They are transcribed in the antiparallel orientation with respect to IE180. Recent reports [Lokensgard et al, Arch. Virol., 110: 129-136 (1990); Priola et al., J. Virol., 64: 4755-4760 (1990)] indicated that PRV LATs are encoded by DNA sequences that extend over 14 kb of the viral genome. Several RNA species (0.95, 2.0, and 5.0 kb) have been reported, and apparently, contradictory results have been obtained regarding the poly(A) nature of the LATs.

B. PRY Vaccines

It is generally known that the herpesviruses genome contains nonessential regions, which can be modified to attenuate the virus. The extent of modification must be carefully controlled. A virus which is insufficiently attenuated will either retain pathogenicity or revert to virulent state. One which is too extensively attenuated will fail to elicit an adequate immune response. Appropriately attenuated viruses will manifest the safety of subunit vaccines and efficacy of live virus vaccines.

European Patent Publication No. 0 141 458 entitled "Deletion Mutant of a Herpesvirus and Vaccine Containing Same" contemplates the construction of attenuated PRV having deletions in the $U_S$ region or in the repeat sequences. Little information is given on attenuation by deletion in the repeat sequences.

U.S. Pat. No. 4,514,497, entitled "Modified Live Pseudorabies Viruses" teaches temperature resistant PRV having deletions in the thymidine kinase (Tk) gene located in the $U_L$ region.

Pat. No. PCT/US86/01804 entitled "Pseudorabies Virus Deletion Mutants and Vaccines Containing Same" assigned to Syntrovet Incorporation has indicated the importance of the junction region between the unique long and internal repeat region for the attenuation of PRV. However, there is no description of its involvement in PRV latency. This is not surprising, since the latency-associated transcripts for herpes simplex virus were first described in 1987, and those for PRV were not described until 1989 [first by Cheung, J. Virol. 63: 2908–2913 (July 1989); then by Lokengard et al., Arch. Virol. 110: 129–136 (1990)].

Kit et al., U.S. Pat. No. 4,711,850, herein incorporated by reference, teach the construction of PRV mutants containing deletion and/or insertion mutations in a major viral glycoprotein gene, g92, such that no antigenic polypeptides encoded by the viral gene are produced. Animals vaccinated with the routants can be distinguished from animals infected with PRV field strains and known PRV vaccines. A comprehensive discussion of PRV disease, the development of vaccines to control the disease, the genomes of PRV strains, and PRV envelope proteins is given in columns 1–11 of this patent.

SUMMARY OF THE INVENTION

As a prelude to this invention, Cheung [Journal of Virology, 65: 5260–5271 (1991)] has identified and sequenced an 8.5-kb PRV-specific poly(A)RNA species in the trigeminal ganglia of a latently infected swine. This mRNA, referred to herein as "PRV LLT", has an open reading frame (ORF) capable of encoding a 200-kDa protein. Cheung, supra, has also identified a PRV early polypeptide homologous to the HSV-1 ICP0, designated early protein 0 (EP0). The gene for PRV EP0 is transcribed to a 1.75 kb polyadenylated mRKA. The direction of transcription of the LLT gene is antiparallel to that of the IE180 gene and the EP0 gene. The latency transcript overlaps the entire IE180 gene and most of the EP0 gene.

In conjunction with these findings, we have discovered a novel region of the PRV genome suitable as a target for modification in the construction of an attenuated virus which has reduced ability to reactivate from latency. Attentuation can be achieved by functionally disabling the expression of the EP0 gene, or by disrupting the synthesis of the LLT, or both. In the preferred embodiment of the invention described below, a substantial portion of the EP0 gene and complementary portion of the overlapping LLT gene are deleted. The resultant virus is characterized by a significant level of attentuation and substantially reduced latency potential as compared to the field strains of the virus. Moreover, the deletion mutant retains the immunogenicity of the field strain.

In accordance with this discovery, it is an object of the invention to correlate the novel EP0 gene and the LLT with PRV virulence.

It is also an object of the invention to identify a strategy for disabling the EP0 gene and thereby blocking expression of the EP0 protein in PRV.

Another object of the invention is to produce an attenuated, PRV capable of eliciting a strong immune response in animals susceptible to the disease.

A further object of the invention is to provide a novel, nonpathogenic and highly protective PRV swine vaccine comprising the PRV having a substantial portion of the EP0 gene deleted.

Other objects and advantages of the invention will become readily apparent from the ensuing description.

BRIEF DESCRIPTION OF THE FIGURES

FIGS. 2a and 2b show the nucleotide sequence of the PRV LLT and predicted amino acid sequence of ORF-2.

FIG. 3 shows the nucleotide and deduced amino acid sequences of the EP0 gene.

FIG. 4 is a comparison of the deduced homologous protein domain of PRV EP0 with the protein domains of HSV-1 ICP0 and varicella-zoster gene 61.

DETAILED DESCRIPTION OF THE INVENTION

"Vaccine" is defined herein in its broad sense to refer to any type of biological agent in an administrable form capable of stimulating an immune response in an animal inoculated with the vaccine. For purposes of this invention, the vaccine may comprise either the mutant virus itself or an immunogenic (antigenic) component thereof.

The basic strategy for constructing the vaccines of the invention is to first clone target PRV DNA sequences in a plasmid, and then to modify the cloned DNA prior to reinserting it into the viral genome. As previously mentioned and as discussed in further detail below, the modification should be sufficient to functionally disable the expression of the EP0 gene, to disrupt the synthesis of the LLT, or both. These genes are present in naturally-occurring and all commercial vaccine pseudorabies viruses. The modification may be in the form of a deletion, an insertion, or both. In the case of producing a deletion mutant, a hybrid plasmid containing the viral DNA and a selectable marker is treated with a restriction enzyme known to cause the desired deletion. The modified DNA is then reinserted into the viral genome for the purpose of rendering the virus nonpathogenic. The conventional technique for reinsertion is to co-transfect animal cells with both the modified viral DNA-containing plasmid and also wild type intact virus. The animal cells are cultured under suitable conditions to permit recombination of the modified viral DNA with the viral genome. The mutated virus is thereafter selected and recovered.

Figure 1D:
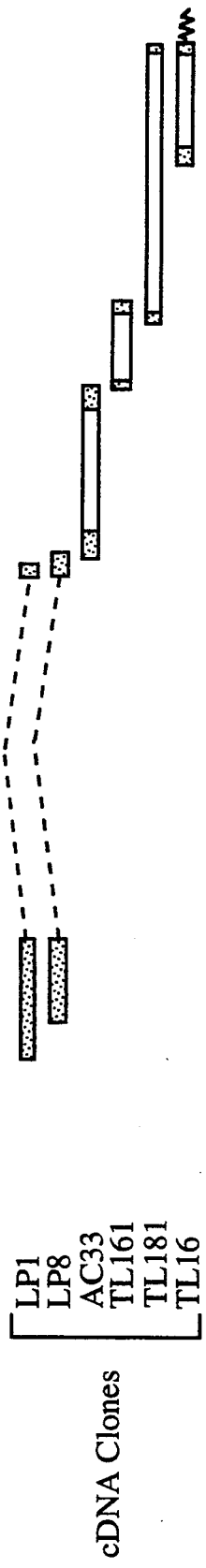
FIG. 1 comprises: (A) a schematic diagram of the PRV genome and its BamHI restriction enzyme map; (B) an expanded diagram of BamHI-G, -P, -J, -I, and -E and KpnI-F and -E restriction fragments in this region; (C) a diagram of available genomic DNA nucleotide sequences of three different strains of PRV and the location of PRV IE180; (D) a diagram of six overlapping cDNA clones; (E) a diagram of the PRV LLT and three possible open reading frames thereof; (F) the intron boundaries of the LLT gene; and (G) a diagram depicting the localization of a cDNA clone and its corresponding EP0 transcript.
Figure 1E:
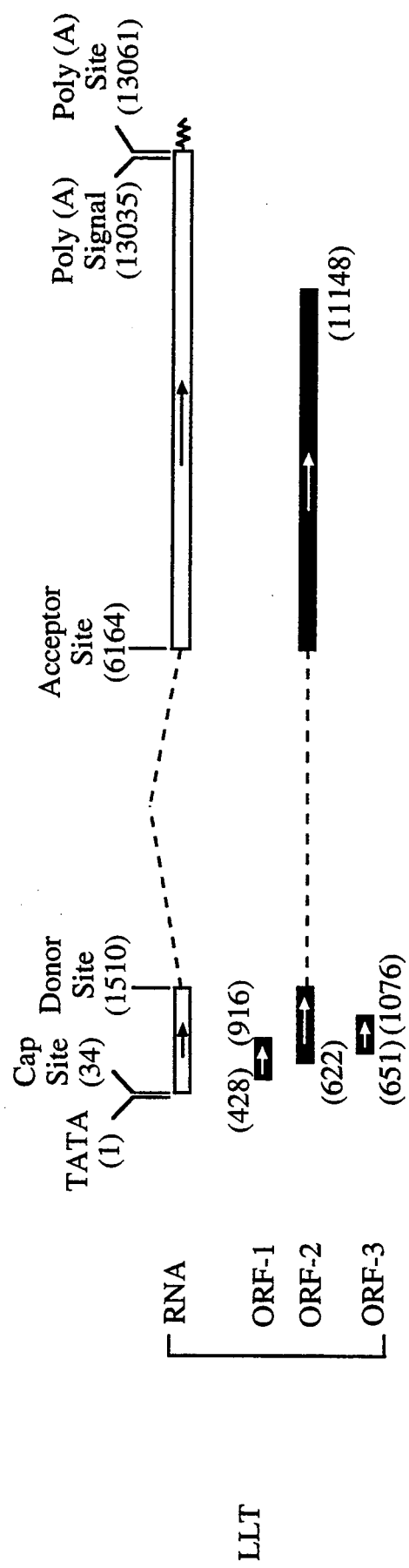
Figures 1F, 1G:
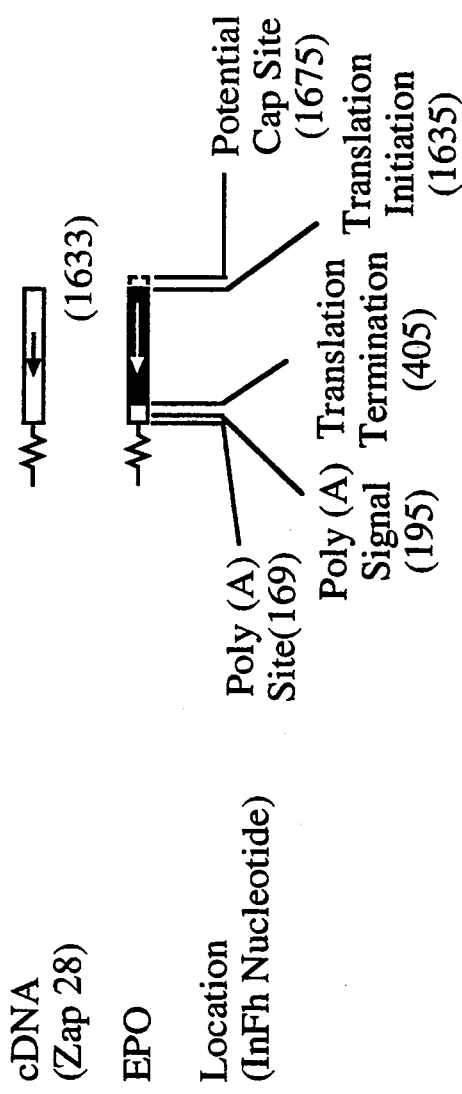

FIG. 1 depicts the relationship between the PRV genome fragments and transcripts pertinent to the ensuing discussion.

FIG. 1 (A) is a schematic diagram of the PRV genome and BamHI restriction enzyme map. The genome is organized into the unique long ($U_L$), internal repeat ($I_R$), unique short ($U_S$), and terminal repeat ($T_R$) sequences. FIG. 1 (B) is an expanded diagram of BamHI-G, -P, -J, -I, and -E and KpnI-F and -E restriction fragments in this region. FIG. 1 (C) shows available genomic DNA nucleotide sequences of three different strains of PRV (InFh, Ka, and Becker) and the location of PRV IE180. The direction of IE180 transcription is indicated by an arrow (leftward), and the poly(A) tail is indicated by a squiggle. Shaded areas represent the coding sequence. FIG. 1 (D) depicts six overlapping cDNA clones. The cDNA library was constructed with total cellular RNAs from the trigeminal ganglia of a latently infected swine. The standard method with oligo(dT) primer was used for cDNA synthesis [Gubler et al., Gene, 25: 263–269 (1983)] and the cDNA was cloned into the lambda gt10 vector system [Huyah et al., In D. M. Glover (ed.), vol I, IRL Press, Oxford, 49–78 (1985)]. Nick-translated probes derived from BamHI-P, -J, and -I were used to screen for PRV-specific clones. DNA inserts were exercised and subcloned into Bluescript plasmids (Stratagene), and the DNA sequences were determined by the dideoxy-chain termination method [Sanger et al., Proc. Natl. Acad. Sci. USA74: 5463–5467 (1977)]. Areas for which nucleotide sequences have been determined are stippled. Dotted lines indicate splicing. FIG. 1 (E) is the LLT. Points of interest are indicated by the first nucleotide of the element. The direction of transcription is rightward, with a poly(A) tail at the 3' end. Three possible ORFs are shaded; the coordinates for the coding sequences (based on PRV-InFh and -Ka) are also indicated. In FIG. 1 (F) intron boundaries are shown. The nucleotide sequence and deduced amino acid residues (in single-letter code) in the vicinity of the splice junctions are shown. The consensus dinucleotides present at the intron boundaries are underlined. Nucleotide 1510(+), together with nucleotides 6164 and 6165, codes for the glycine residue. FIG. 1 (G) identifies the localization of a cDNA clone (Zap28) and its corresponding EP0 transcript. Arrows indicate the direction of transcription, dotted lines indicate splicing, and squiggles indicate poly(A) tracks. Shaded areas indicate ORFs.

The PRV latency gene is encoded by DNA sequences present in the BamHI-G, -P, -J, -I add -E fragments of the virus genome. The nucleotide sequence (SEQ ID No. 1) of the complete PRV LLT and predicted amino acid sequence (SEQ ID NO. 2) of ORF-2 are given in FIG. 2. The basic sequence is derived from PRV-InFh (from nucleotides 1 to 7013) and PRV-Ka (from nucleotides 7014 to 8425). In FIG. 2, PRV-Becker nucleotides that differ from the prototype are indicated in small letters above the basic sequence, the corresponding amino acid residue changes are presented at the third position of the codon, deletions are indicated by parentheses with dots on top, and insertions are indicated above the basic sequence in brackets. Nucleotide coordinates after the splice junction at nucleotide 1511 apply only to LLT. DNA nucleotide sequences of the TATA box and the poly(A) signal and the amino acid sequences of the histidine-rich, acidic residue-rich, and cysteine-rich regions of the polypeptide are underlined. The RNA cap site, poly(A) addition site, and termination codon are indicated by asterisks.

As mentioned earlier, the latency gene transcript (LLT) overlaps and is transcribed in the opposite orientation with respect to the EP0 and the immediately early gene (IE180). EP0 is nonessential for replication, the latency gene is the only gene expressed during PRV latency, and the IE180 gene is absolutely necessary for PRV replication. However, two copies of IE180 are present in the genome (one in the internal repeat and one in the terminal repeat). It is expected that PRV lacking one of the IE180 copies is viable. Therefore, deletion in the non-overlapping regions of these 3 genes will generate single deletion routants, while deletions in overlapping regions will generate double deletion mutants.

The nucleotide sequence (SEQ ID NO. 3) and the deduced amino acid sequence (SEQ ID NO. 4) of EP0 are given in FIG. 3. The DNA nucleotide sequence was determined by the dideoxy-chain termination method [Sanger et al. supra]. The first six nucleotides of this sequence constitute a BamHI restriction site, which is located between BamHI-P and BamHI-J in FIG. 1; transcription is leftward, as indicated by the arrow. The potential cap site and the termination codon are indicated by asterisks. The cysteine-rich zinc finger motif and the polyadenylation signal are underlined. The actual poly(A) addition site is located at the last nucleotide of the sequence.

The most important domain of the EP0 gene is likely to be the cysteine-rich zinc-finger domain from amino acid 40 to amino acid 100, since this region is conserved among other herpesviruses (e.g. herpes simplex virus type 1 and varicella-zoster virus). FIG. 4 is a comparison of the deduced homologous protein domain of PRV EP0 (SEQ ID NO. 5) with the protein domains of HSV-1 ICP0 (SEQ ID NO. 6) and varicella-zoster gene 61 (SEQ ID NO. 7). The coordinates indicate the positions of the amino acid residues in their respective polypeptides. Gaps are introduced into the sequence (in dashes) for best alignment. Identical residues are indicated by asterisks between the sequences. Cysteine residues that are part of the zinc finger motif are overlined. The DNA sequence encoding this cysteine-rich domain also encodes an amino acid sequence specific to the latency gene in the opposite orientation. In fact, deletion in the EP0 gene other than the first 200 bp of EP0 will automatically delete some of the DNA sequences encoding the latency gene. The important domain of LLT has not been elucidated at present, but the latency gene is expected to play a role in the establishment, maintenance, or reactivation of PRV latency. The deletion may be totally comprised of a portion of EP0 sequence or a portion of the LLT sequence. Furthermore, a sequence nonessential for replication may be deleted from both EP0 and LLT sequences, from both of the LLT and IE180 sequences, or from a portion of each of EP0, LLT and IE180. Though disablement of a gene can be accomplished by single point mutation, the risk of reversion is minimized with more extensive modification. Accordingly, it is preferred that the deletion comprise at least 100 base pairs, and more preferably several hundred base pairs. Moreover, in the design of a commercial pseudorabies vaccine, it may be desirable to incorporate the aforementioned modifications in conjunction with other functional modifications currently in use in commercial vaccines. For example, it may be advantageous to also incorporate one or more of the gp1, gpX or TK deletions.

Figure 5A:
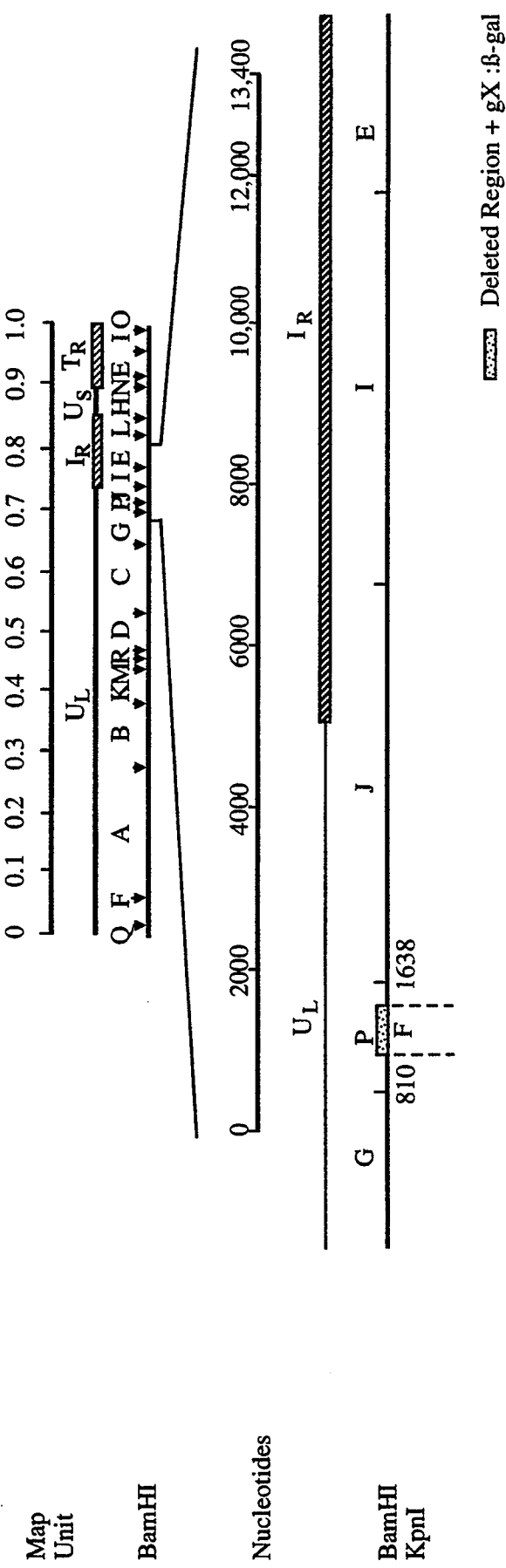
FIG. 5 outlines a strategy to delete a portion of the latency gene and the EP0 gene simultaneously. The figure includes: (A) map unit and BamHI fragments of the PRV genome; (B) location of the LLT transcript and the immediately early gene (IE180) transcript; and (C) location of the EP0 transcript.
Figure 6:
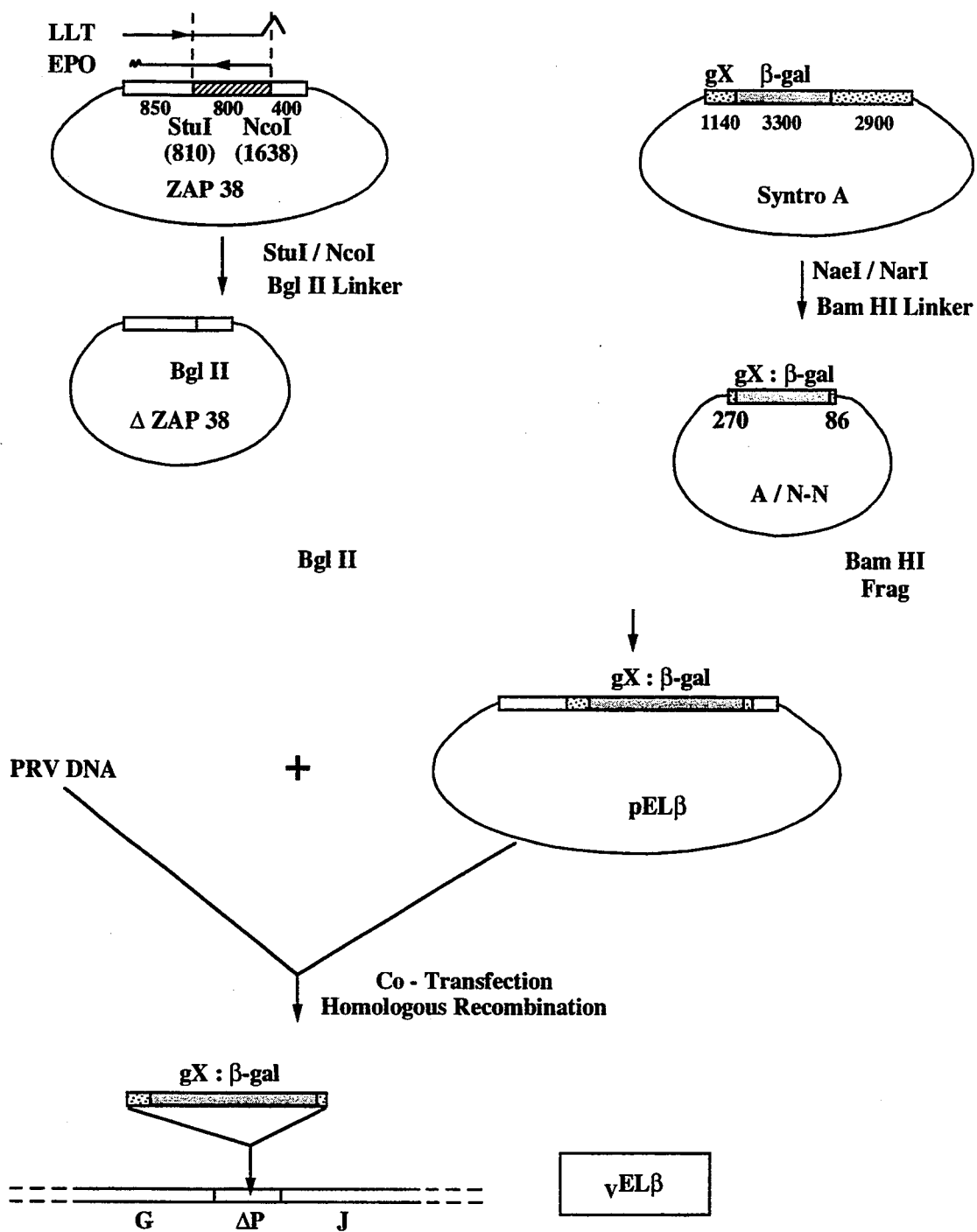
FIG. 6 is a schematic diagram showing the starting materials (plasmids ZAP38, plasmid Syntro A and wild type PRV DNA) and the procedures to generate a recombinant virus in which the 800 bp Stu-NcoI fragment of BamHI-P is replaced by the E. coli beta-galactosidase gene.
Figure 7A:
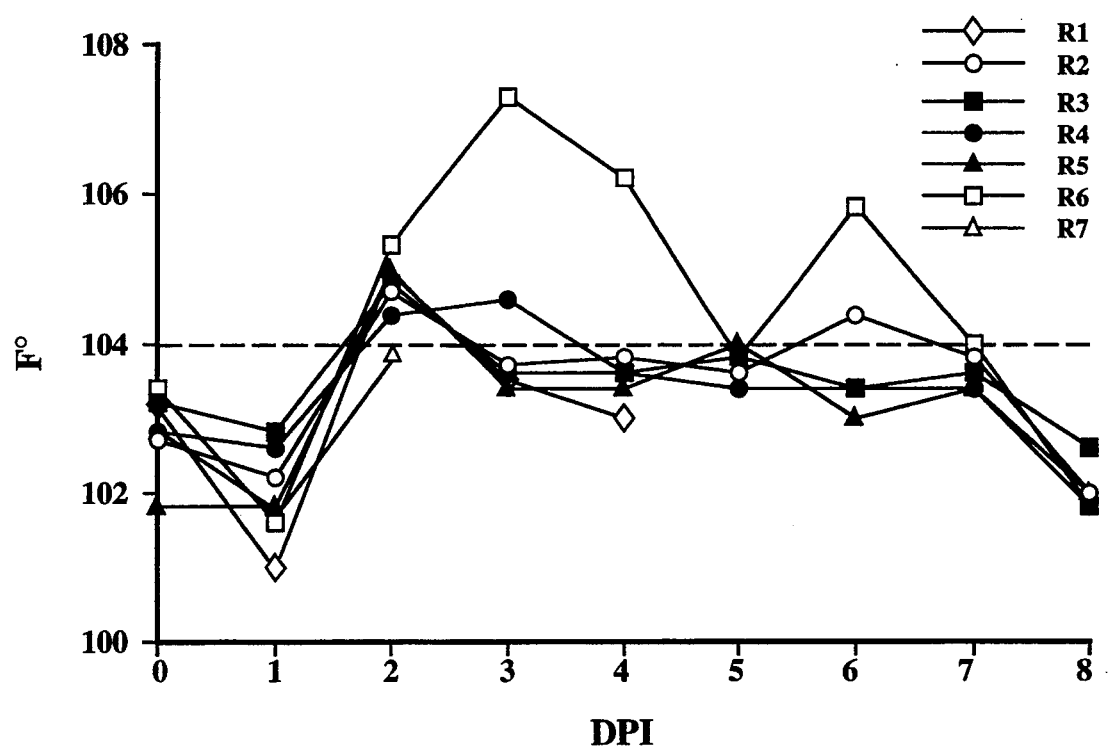
FIGS. 7a and 7b are a graphical depiction of the comparative body temperature profiles of swine following Indiana-Funkhauser (InFh) and EL$\beta$-001 virus infection.
Figure 7B:
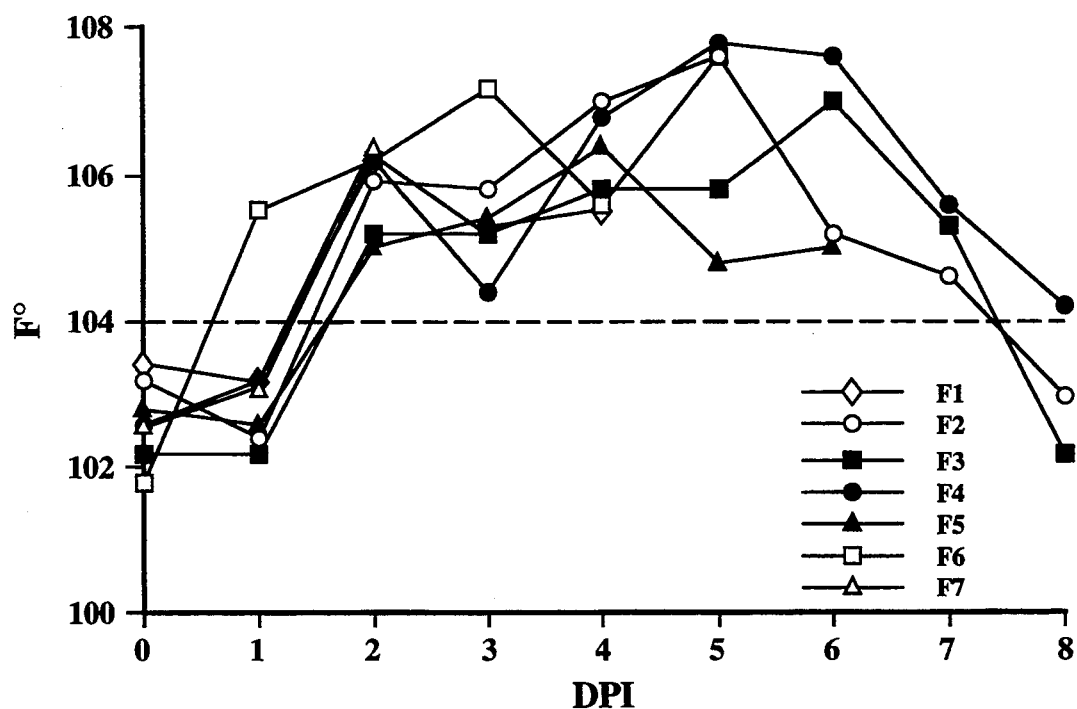

In an embodiment of the invention illustrated in the Examples, below, a nonessential sequence comprising about 800 base pairs present in both the EP0 and the LLT sequences have been deleted and replaced by the *E. coli* β-galactosidase gene in an attenuated PRV virus. The strategy for this double deletion is outlined in FIG. 5. FIG. 5A shows the map unit and BamHI fragments of the PRV genome. The location of the LLT transcript and the IE180 transcript are shown in FIG. 5B. FIG. 5C depicts the location of the EP0 transcripts. In the expanded BamHI, G, -P, -J, -I, -E diagram of FIG. 5A, the region represented by the stippled box in BamHI-P (nucleotide 810 to 1638), when deleted, will yield deletions both in the LLT and in the EP0 transcripts. The deleted DNA sequences will be replaced by the β-galactosidase gene under the control of the PRV gX gene promoter. A schematic diagram for constructing this virus, designated ELβ-001, is depicted in FIG. 6. ELβ-001 does not grow as well in tissue culture as the field strain viruses in that it yields smaller plaque size and reduced titer. It also exhibits reduced virulence in animal experiments when compared to the parent InFh virus.

The modified virus of the invention is prepared for administration by formulation in an effective immunization dosage with a pharmaceutically acceptable carrier or diluent, such as physiological saline. The expression "effective immunization dosage" is defined as being that amount which will induce immunity in a vaccinated animal against challenge by a virulent strain of PRV. Immunity is considered as having been induced in a population of animals when the level of protection for the population is significantly higher than that of an unvaccinated control group. Typically, the vaccine will contain at least about $10^3$ PFU (plaque-forming units) of the virus, and preferably between $10^4$ and $10^6$ PFU.

Appropriate adjuvants as known in the art may also be included in the vaccine formulation. In many cases, the vaccinal efficacy can be enhanced by combining the deletion mutant virus with other viral agents into bivalent or polyvalent vaccines.

The vaccines of this invention may be administered by any conventional route as recognized in the art. For example, the vaccine may be administered intranasally, orally, or by injection. The modes of injection contemplated include intramuscular, subcutaneous, interperitoneal and intravenous injection.

Animals vaccinated with the modified viruses prepared in accordance with this invention will have reduced fever, reduced virus shedding and fewer clinical signs of the pseudorabies disease. The virus is effective in eliciting an immune response capable of protecting swine from a lethal PRV challenge. Swine vaccinated with PRV lacking the EP0 gene and latency gene harbors less PRV DNA in the nervous tissue, and these animals showed reduced ability to yield reactivatable virus.

Notwithstanding the aforementioned similarities between the PRV EP0 and the HSV ICP0, EP0 is an early protein gene whereas ICP0 is an immediately early gene. Also, ICP0 is located in the repeat sequence, but EP0 is not. There is only limited and patchy homology between the amino acid sequence of EP0 and that of ICP0.

The following examples are intended only to further illustrate the invention and are not intended to limit the scope of the invention which is defined by the claims.

Materials and Methods

In the ensuing example, the starting wild-type PRV was the virulent, InFh strain. The virus was propagated in Madin-Darby bovine kidney cells (MDBK). The PRV DNA was prepared by the method described in Paul et al. [Arch. Virol. 73: 193–198 (1982)]. Plasmid DNA was prepared by the method of Maniatis et al., Molecular Cloning: A Laboratory Manual, Cold Spring Harbor Laboratory Press (1982)]. DNA fragments were purified from agarose gels following electrophoretic resolution according to the "Gene Clean Kit" purchased from Bio 101, Inc. DNA was transformed into *E. coli* strain XL-1 Blue by methods described by Maniatis, supra; and DNA was transfected into animal cells using the lipofectin reagents purchased from Bethesda Research Laboratories (BRL).

Viruses obtained from tissue culture monolayers infected with pseudorabies recombinant viruses were selected for the presence of the β-galactosidase gene in Bluo-gal (BRL)-containing agar plates.

Restriction fragments of DNA were rendered blunt using S1 nuclease or the Klenow fragment of *E. coli* DNA polymerase, and terminal phosphate residues were removed by digestion with calf-intestine phosphatase, all as described in Maniatis, supra.

EXAMPLE 1

Construction of ELβ-001

Deletions were concurrently introduced into the EP0 and latency genes of the InFn strain of PRV as described, below, in reference to FIG. 6.

A contiguous nucleotide sequence containing the right hand most 400 base pairs of BamHI-G, the complete BamHI-P, and the left hand most 200 base pairs of BamHI-J of PRV InFh strain was cloned into the Bluescript plasmid resulting in plasmid ZAP38. Contained within this region is a 800 base pairs StuI-NcoI fragment which encodes a portion of the latency gene (rightward orientation) and a portion of the EP0 gene (leftward orientation). Plasmid ZAP38 was cut with StuI and NcoI enzymes, blunt-ended, BglII linker added, digested with BglII and religated to create a deletion of 800 base pairs with the addition of a new BglII site (plasmid ΔZAP38). Plasmid Syntro A that contains the β-galactosidase gene with PRV gX DNA sequences (1140 base pairs at the 5' end and 2900 base pairs at the 3' end) was cut with NaeI and NarI enzymes, blunt ended, BamHI linker added, digested with BamHI and religated into Bluescript vector to yield plasmid A/N-N. Plasmid A/N-N has shorter PRV sequence at the 5' end (270 bp) and the 3' end (86 bp). The BamHI fragment containing the β-galactosidase gene in plasmid A/N-N was then inserted into the BglII site of plasmid ΔZAP38 to generate plasmid pEIβ. Plasmid pELβ was used in a transfection experiment in the presence of wild type pseudorabies virus DNA in MDBK cells. Recombinant viruses were generated via homologous recombination and the recombinant viruses were selected in the presence of Bluo-gal that yielded blue color plaques.

Candidate recombinant viruses (V) were isolated from wild type PRV by plaque purification DNA from the candidate recombinants was analyzed by restriction digestion and Southern blotting to establish the presence of a deletion in the viral genome. By this procedure, a PRV mutant having a confirmed deletion in BamHI-P has been isolated and is hereafter referred to as ELβ-001. Viral DNA isolated from the parent InFh virus and ELβ-001 gave similar BamHI restriction enzyme patterns. However, hybridization of the blots with BamHI-P probe showed that the regular size BamHI-P fragment in the InFh genome and a BamHI-P clone was replaced by a higher molecular weight fragment in ELβ-001. Hybridization with the β-galactosidase DNA probe showed the ELβ-001 genome contains the β-galactosidase gene while the parent virus does not. Furthermore, the β-galactosidase gene was inserted into the BamHI-P fragment of ELβ-001. Hybridization with the 800 StuI-NcoI fragment probe showed that this DNA sequence is present in the InFh genome but deleted in the ELβ-001 genome. Thus ELβ-001 had suffered a deletion in both the EP0 and latency genes but acquired the β-galactosidase gene which is expressed during replication. The β-galactosidase gene is a selectable marker and is not critical for PRV attenuation or latency.

EXAMPLE 2

Animal Trials with ELβ-001

Animal studies with young (5-day-old) and weaned (4-week-old) piglets were initiated to compare the safety (degree of virulence) of ELβ-001 with that of the parent wild-type PRV, InFh. The level of antigenicity as measured by the humoral immune response, and the degree of protection from a fatal challenge dose of InFh was also determined. All piglets used in these studies were first shown to be negative for PRV antibody by the latex agglutination test.

Four-week-old Piglets

Initial experiments were conducted with two groups (R and F) of 4-week-old, weaned piglets (eight piglets in a group). These animals were infected intranasally with $1.4\times10^6$ PFU of either ELβ-001 (R group) or InFh (F group) virus. Nasal swabs were taken daily to measure virus shedding (Table 3), daily body temperatures were determined (FIG. 7) and the pigs were observed for clinical signs. Blood samples were taken at designated times and the serum was tested for antibody to PRV. At predetermined times post-inoculation, pigs were euthanized and trigeminal ganglia removed to test for the presence of PRV virus genomes (Table 6).

The results indicate the ELβ-001 replicates in 4-week-old piglets and causes minimum clinical signs; only a slightly elevated temperature was detected (FIG. 7). Serum antibody could be detected in all R-group and F-group piglets by 7 to 8 days post-inoculation. One piglet in each group had a weak antibody response by the latex agglutination test while four piglets in each group developed a strong antibody response. No clinical signs were observed for the R-group piglets whereas sneezing, inappetence, shivering, and huddling, depression and CNS signs were observed in the F group animals. Two of five control F group piglets showed CNS signs, and two of five died by day 7 post-inoculation (Table 3).

Daily temperatures and nasal swabs of the R- and F-group piglets indicate the ELβ-001 replicates less than InFh virus in 4-week-old piglets. Only one R-group piglet (R-6) had an elevated temperature [above 104° C. F.)] lasting for more than a single day (FIG. 7A). In contrast, all of the F-group piglets had elevated temperatures lasting for 4–6 days post-inoculation (FIG. 7B). Moreover, the replication of ELβ-001 virus in the nasal cavity of these piglets was reduced compared to that of InFh virus (Table 3). InFh virus was recovered easily from all F-group piglets between 7 and 8 days post-inoculation. For the R-group piglets, the amount and duration of virus shedding was significantly less. The results indicate that ELβ-001 is less virulent for weaned piglets.

Five-Day-Old Piglets

To compare the effect of ELβ-001 and InFh in younger animals and to determine the dose response to these viruses a total of 43 piglets (5 days old) were used. Initially, two groups of 10 and 9 piglets were infected intranasally with $1.4\times10^6$ PFU of ELβ-001 (B-group) or $1.4\times10^6$ PFU of InFh (T-group) virus. Both nasal (Table 2) and pharangeal (Table 1) swabs were taken for 8 days post-inoculation. Similar to the older piglets, the ELβ-001 virus replicated less extensively in the 5-day-old piglets. Virus was recovered from all the B-group piglets, although some animals were shedding at a very low level. InFh virus replicated extensively in these piglets (T-group) and by day 5 had killed all of these piglets. At this dosage, only 3 of 7 piglets survived the ELβ-001 inoculation (Table 4).

Three lower doses were used to determine the effect of ELβ-001 and InFh on the 5-day-old piglets. At the low doses, all of the ELβ-001 infected piglets survived; whereas, with InFh, only the piglets inoculated with $5\times10^3$ PFU survived (Table 4). Piglets infected with $5\times10^3$ PFU ELβ-001 showed no clinical signs of pseudorabies virus disease; at $5\times10^4$ PFU, two piglets were normal and two piglets were off feed and depressed; and at $5\times10^4$ all four of the ELβ-001 infected piglets were inappetent, depressed and had some diarrhea (Table 5). These results show that ELβ-001 is more pathogenic for 5-day-old piglets than for 4-week-old piglets but, this deletion mutant is still significantly less virulent than InFh for 5-day-old piglets.

Protection

The piglets infected with ELβ-001 at 5 days of age were positive for PRV antibody by 17 days post-inoculation (Table 5). When these piglets were 3 weeks old, the groups infected with $5 \times 10^3$ PFU (four piglets), $5 \times 10^4$ PFU (four piglets), and $1.4 \times 10^6$ PFU (three surviving piglets) of ELβ-001 were challenged with $10^7$ PFU per nostril of InFh. All 11 vaccinated piglets survived the challenge virus exposure without notable clinical signs (Table 5). Even the group of piglets free of clinical signs with the lowest dose of ELβ-001 ($5 \times 10^3$ PFU) was also solidly protected. Twelve control piglets (3 weeks of age), negative for PRV antibody, all were anorexic and depressed, some showed CNS signs and all died within a range of 5 to 8 days post-challenge (Table 5). These experiments indicate that ELβ-001 induces solid protective immunity even when challenged with wild-type PRV at a young age.

Virus Reactivation and Genome Detection

Studies were also conducted to examine the ability of ELβ-001 to reactivate from infected swine after induction with dexamethasone and to determine the amount of ELβ-001 or InFh genome harbored in the trigeminal ganglia of these infected animals. The results (Table 6) showed that the parent InFh virus reactivated more readily and harbored more DNA genome in comparison with ELβ-001 infected animals.

TABLE 1

Virus shedding patterns (pharyngeal) in 5-day-old piglets infected with ELβ-001 and InFh

| Pig No. | 1 | 2 | 3 | 4 | 5 | 6 | 7 | 8 |
|---|---|---|---|---|---|---|---|---|
| B1[a] | 69 | 87 | 175 | 0 | | | | |
| B2[b] | 42 | 3 | 74 | 5 | 5 | | | |
| B3[b] | 0 | 3 | 0 | 2 | 1 | 0 | 0 | 0 |
| B4 | 3 | 7 | 0 | 0 | 3 | 1 | 0 | 0 |
| B5[b] | 25 | 15 | 0 | 0 | 0 | | | |
| B6 | 8 | 144 | 42 | 2 | 0 | 51 | 166 | 3 |
| B7[a] | 6 | 136 | | | | | | |
| B8 | 1 | 2 | 15 | 0 | 4 | 16 | TNTC | 1 |
| B9[b] | 0 | 0 | 0 | 1 | 0 | 0 | 0 | 0 |
| B10[a] | 56 | | | | | | | |
| T1[a] | TNTC | | | | | | | |
| T2[b] | TNTC | TNTC | TNTC | | | | | |

TABLE 1-continued

Virus shedding patterns (pharyngeal) in 5-day-old piglets infected with ELβ-001 and InFh

| Pig No. | 1 | 2 | 3 | 4 | 5 | 6 | 7 | 8 |
|---|---|---|---|---|---|---|---|---|
| T3[b] | TNTC | TNTC | TNTC | | | | | |
| T4[b] | TNTC | TNTC | TNTC | TNTC | | | | |
| T5[b] | 121 | TNTC | TNTC | | | | | |
| T6[b] | 8 | TNTC | TNTC | TNTC | | | | |
| T7[b] | TNTC | TNTC | TNTC | TNTC | | | | |
| T8[b] | TNTC | TNTC | 0 | | | | | |
| T9[a] | 80 | TNTC | | | | | | |

B = ELβ-001.
T = InFh virus.
TNTC = Too numerous to count.
[a]Euthanized.
[b]Dead

TABLE 2

Virus shedding patterns (nasal) in 5-day-old piglets infected with ELβ-001 and InFh

| Pig No. | 1 | 2 | 3 | 4 | 5 | 6 | 7 | 8 |
|---|---|---|---|---|---|---|---|---|
| B1[a] | 0 | 0 | 0 | 3 | | | | |
| B2[b] | 0 | 0 | 0 | 2 | 0 | | | |
| B3[b] | 0 | 0 | 0 | 2 | 0 | 0 | 0 | 0 |
| B4 | 0 | 0 | 0 | 1 | 0 | 1 | 0 | 0 |
| B5[b] | 0 | 0 | 0 | 0 | 0 | | | |
| B6 | 0 | 0 | 0 | 0 | 0 | 24 | 0 | 0 |
| B7[a] | 0 | 0 | | | | | | |
| B8 | 0 | 0 | 0 | 4 | 0 | 1 | 0 | 1 |
| B9[b] | 0 | 0 | 0 | 0 | 6 | 0 | 0 | 1 |
| B10[a] | 0 | | | | | | | |
| T1[a] | 1 | | | | | | | |
| T2[b] | 0 | 41 | 4 | | | | | |
| T3[b] | 15 | 1 | 17 | | | | | |
| T4[b] | 0 | 3 | 9 | 44 | | | | |
| T5[b] | 1 | 5 | 11 | | | | | |
| T6[b] | 10 | 36 | 106 | TNTC | | | | |
| T7[b] | 7 | 2 | 300 | TNTC | | | | |
| T8[b] | 3 | 97 | 87 | | | | | |
| T9[a] | 3 | 98 | | | | | | |

B = ELβ-001.
T = InFh virus.
TNTC = Too numerous to count.
[a]Euthanized.
[b]Dead

TABLE 3

Virus shedding patterns (nasal) in 4-week-old piglets infected with InFh or ELβ-001

| Pig No. | 1 | 2 | 3 | 4 | 5 | 6 | 7 | 8 |
|---|---|---|---|---|---|---|---|---|
| R1[a] | 4 | 0 | 0 | 0 | | | | |
| R2 | 2 | 0 | 0 | 0 | 0 | 0 | 0 | 0 |
| R3 | 0 | TNTC | 0 | 46 | 72 | 188 | 251 | 0 |
| R4 | 0 | 0 | 0 | 0 | 0 | 0 | 0 | 0 |
| R5 | 2 | 7 | 1 | 0 | 0 | 0 | 0 | 0 |
| R6 | 0 | 0 | 7 | TNTC | TNTC | TNTC | 3 | 0 |
| R7[a] | 0 | 0 | | | | | | |
| R8[a] | 6 | | | | | | | |
| F1[a] | 1 | TNTC | TNTC | TNTC | | | | |
| F2 | 0 | TNTC | 43 | TNTC | TNTC | TNTC | 2 | 3 |
| F3 | 0 | 231 | 55 | TNTC | TNTC | TNTC | 23 | 1 |
| F4 | 16 | TNTC | TNTC | TNTC | TNTC | TNTC | TNTC | TNTC |
| F5[b] | 0 | TNTC | TNTC | TNTC | TNTC | TNTC | | |
| F6[b] | 54 | 42 | TNTC | | | | | |
| F7[a] | 1 | TNTC | | | | | | |
| F8[a] | 70 | | | | | | | |

F = InFh virus.
R = ELβ-001.
TNTC = Too numerous to count.
[a]Euthanized.
[b]Dead

TABLE 4

Comparative virulence of InFh and ELβ-001 viruses for 5-day-old and 4-week-old piglets.

| Age | Inoculum[a] | ELβ-001 Survivors/Total | InFh Survivors/Total |
|---|---|---|---|
| 5-days | $5 \times 10^3$ | 4/4 | 4/4 |
| | $5 \times 10^4$ | 4/4 | 1/4 |
| | $5 \times 10^5$ | 4/4 | 0/4 |
| | $1.4 \times 10^6$ | 3/7 | 0/7 |
| 4-wks | $1.4 \times 10^6$ | 5/5[b] | 3/5[c] |

[a]PFU/nostril
[b]No clinical signs
[c]Clinical signs: sneezing, inappetent, huddling, lethargic, CNS signs

TABLE 5

Responses and protection of 5-day old piglets vaccinated with ELβ-001

| Group | Dose[a] of ELβ | Pig # | POST-VACCINATION Antibody[b] | POST-VACCINATION Clinical[c] | Pig # | POST-CHALLENGE Antibody[b] | POST-CHALLENGE Clinical[c] |
|---|---|---|---|---|---|---|---|
| A | $5 \times 10^3$ | 1 | + | N | | NT | N |
| | | 2 | + | N | | + | N |
| | | 3 | + | N | | + | N |
| | | 4 | + | N | | + | N |
| B | $5 \times 10^4$ | 5 | + | A | | NT | N |
| | | 6 | + | N | | + | N |
| | | 7 | + | A | | + | N |
| | | 8 | + | N | | + | N |
| C | $5 \times 10^5$ | 9 | NT[d] | A | | Not challenged | |
| | | 10 | NT | A,S | | | |
| | | 11 | NT | A,S | | | |
| | | 12 | NT | A,S | | | |
| D | $1.4 \times 10^6$ | B2 | NT | A,S,D | | — | — |
| | | B3 | + | A,S,D | | — | — |
| | | B4 | + | A,S | | NT | N |
| | | B5 | NT | A,S,D | | — | — |
| | | B6 | ++ | A,S | | NT | N |
| | | B8 | + | A,S | | NT | N |
| | | B9 | NT | A,S,D | | — | — |
| E | Challenge controls (3 wk old pigs) | | | | C1 | | D |
| | | | | | C2 | | D[f] |
| | | | | | C3 | | D[f] |
| | | | | | C4 | | D |
| | | | | | C5 | | D |
| | | | | | C6 | | D[f] |
| | | | | | C7 | | D |
| | | | | | C8 | | D |
| | | | | | C9 | | D |
| | | | | | C10 | | D |
| | | | | | C11 | | D |
| | | | | | C12 | | D |

[a]PFU/nostril
[b]Latex agglutination test; + = weak positive; ++ = strong positive
[c]N = normal; A = anorexic/depressed; S = scours; D = dead
[d]NT = not tested.
[e]Challenge dose = $10^7$ PFU InFh/nostil
[f]CNS signs

TABLE 6

Reactivation of InFh and ELβ-001 viruses in swine

| Group[a] | No. of pigs | Acute infection Virus isolation | Acute infection (PRV gennome/mg DNA)[b] | Post-dexamethasone treatment Virus isolation | Post-dexamethasone treatment (PRV gennome/mg DNA)[b] |
|---|---|---|---|---|---|
| I | 3 | YES (euthanized) | >200 | N/A | N/A |
| | 5 | YES | N/A | NO | <20 |
| II | 3 | YES (euthanized) | >200 | N/A | N/A |
| | 2 | YES (died) | >200 | N/A | N/A |
| | 3 | YES | N/A | YES | >200 |
| III | 1 | NT (euthanized) | >200 | NT | N/A |
| | 5 | NT | N/A | NT | <20 |
| IV | 1 | NT (euthanized) | >200 | NT | N/A |
| | 1 | NT (died) | >200 | NT | N/A |
| | 4 | NT | N/A | NT | >200 |

N/A = Not applicable
NT = Not Tested
[a]Experiment I - Group I and Group II swine were infected with $1.4 \times 10^6$ PFU/nostril of ELβ-001 and InFh, respectively.
Experiment II - Group III swine were initially infected with $2 \times 10^4$ PFU/nostril and 5 days later with $2 \times 10^6$ PFU/nostril of ELβ-001, while Group IV swine were infected with $2 \times 10^6$ PFU/nostril of InFh. For Group III, euthanasia was carried out on day 6 before the second dose of ELβ-001
[b]Trigeminal ganglion

We claim:

1. A pseudorabies virus having a genomic modification selected from the group consisting of a deletion, and insertion or both in: (1) the early protein 0 gene whereby said virus is characterized by the inability to express the early protein 0; or (2) the large latency transcript gene whereby said virus is characterized by the inability to express said large latency transcript, with the provision that the modification to the large latency transcript is in conjunction with another modification which serves to attenuate the virus.

2. A pseudorabies virus as described in claim 1 wherein said modification is in an overlapping region of the early protein 0 gene and the large latency transcript gene.

3. A pseudorabies virus as described in claim 1 wherein said modification is in an overlapping region of the large latency transcript gene and the immediately-early 180 gene.

4. A pseudorabies virus as described in claim 1 wherein said modification comprises a deletion.

5. A pseudorabies virus as described in claim 1 wherein said modification comprises a deletion in the overlapping region of the early protein 0 gene and the large latency transcript gene.

6. A pseudorabies virus as described in claim 5 wherein said virus is EL$\beta$-001.

7. A vaccine comprising the virus of claim 1 in an effective immunization dosage with a pharmaceutically acceptable carrier or diluent.

8. A vaccine comprising the virus of claim 2 in an effective immunization dosage with a pharmaceutically acceptable carrier or diluent.

9. A vaccine comprising the virus of claim 5 in an effective immunization dosage with a pharmaceutically acceptable carrier or diluent.

10. A vaccine comprising the virus of claim 6 in an effective immunization dosage with a pharmaceutically acceptable carrier or diluent.

11. A method of immunizing an animal against psuedorabies comprising administering to said animal a vaccine comprising a pseudorabies virus having a genomic modification selected from the group consisting of a deletion, and insertion or both in: (1) the early protein 0 gene whereby said virus is characterized by the inability to express the early protein 0; or (2) the large latency transcript gene whereby said virus is characterized by the inability to express said large latency transcript with the provision that the modification to the large latency transcript is in conjunction with another modification which serves to attenuate the virus.

12. A method as described in claim 11 wherein said modification is in an overlapping region of the early protein 0 gene and the large latency transcript gene.

13. A method as described in claim 11 wherein said modification is in an overlapping region of the large latency transcript gene and the immediately-early 180 gene.

14. A method as described in claim 11 wherein said modification is a deletion.

15. A method as described in claim 11 wherein said modification is a deletion in the overlapping region of the early protein 0 gene and the large latency transcript gene.

16. A method as described in claim 15 wherein said virus is EL$\beta$-001.

17. A method as described in claim 11, wherein said animal is a swine.

18. A method as described in claim 11 wherein said virus is present in said vaccine at level of $10^3$–$10^6$ PFU per dose.

19. A method for producing a pseudorabies virus deletion mutant comprising the steps:

(a) constructing a hybrid plasmid comprising a cloning vector, a selectable marker, and a DNA fragment of pseudorabies virus containing substantially all of the pseudorabies virus EP0 gene and flanking sequences thereof;

(b) deleting DNA sequences from the hybrid plasmid such that the early protein 0 is not expressed, while retaining pseudorabies virus DNA sequences adjacent to each side of the deletion;

(c) replacing the deleted sequences from step (b) with the selectable marker;

(d) co-transfecting in pseudorabies virus host cells the resulting plasmid from step (b) with infectious psuedorabies virus DNA; and (e) selecting by means of the selectable marker psuedorabies virus deletion mutants which are characterized by the inability to express the early protein 0.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 8438 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudorabies virus ( i x ) FEATURE:
        ( A ) NAME/KEY: CDS
        ( B ) LOCATION: 622..6495

( i x ) FEATURE:
        ( A ) NAME/KEY: variation
        ( B ) LOCATION: replace(1099, "g")

( i x ) FEATURE:
        ( A ) NAME/KEY: variation
        ( B ) LOCATION: replace(1267, "t")

( i x ) FEATURE:
        ( A ) NAME/KEY: variation
        ( B ) LOCATION: replace(1381, "c")

( i x ) FEATURE:
        ( A ) NAME/KEY: variation
        ( B ) LOCATION: replace(1566, "c")

( i x ) FEATURE:
        ( A ) NAME/KEY: variation
        ( B ) LOCATION: replace(7010, "g")

( x i ) SEQUENCE DESCRIPTION: SEQ ID NO:1:

```
TATATAATCC  CCGGTCCGCG  CTCCGCCCAC  CCATCACAGC  AGCCGCGGAC  GCTGCGCGCC        60

GGAGCGGTCC  ATCTCGCCAG  CCAGCCAACC  AGCCGAGCCG  CCCAGCCGAC  CCGAGAGCCC       120

CGAGAGCCAG  ACTCCCTCAG  CCATAGAAGA  CACCGGGCGG  GAGAGACGGA  CTGAAAAAAT       180

ATATCTTTTT  TTATTTTGTC  TGGGCCTGGA  GACCCGCAGC  AGGAGCGGAG  GTGGGTGCGG       240

GGCCGGGAGC  CGGAGCAGGA  CCGGGAACAG  GAACAGGAAC  AGGAACAGGA  ACAGGAGTGG       300

GGCCGGGAGC  AGGAGCAGGA  GCGGGAGCCG  AAGTGGGGGC  AGGAGCGGCG  GCGGCCGCAG       360

CAGCAACAGG  GTCGCCCCAG  TCCGCGGCGA  GGAAGAGGGA  GCTCAGTCGT  CGTCCTGGGT       420

GAGGTCGATG  AAGATGGTAG  CGGAGCGGGG  GGATCCCGAC  GAGCTAGACG  CCGGAGGCCC       480

GCCCCGGGGG  GCGGCGGTCT  CGGGGGCAGA  GGCAGAGGGC  GACGGGCGCC  GCATCGAGGA       540

GGAGGGTGAA  GACGAGGGGG  AGGAGCGAGC  CGAAGCGGCG  GTGTTCGCCG  ACCCCGGGCC       600

GGCCCCGGCC  CCCGAGGCAC  C ATG CTG CGC AGA GGA CCC CTC GCC GGA CGA            651
                         Met Leu Arg Arg Gly Pro Leu Ala Gly Arg
                          1               5                  10

TGG CGC CTC CGG AGT CTC GCC CTG GGC CTG TCC GCC CGT CCG GCC GCG            699
Trp Arg Leu Arg Ser Leu Ala Leu Gly Leu Ser Ala Arg Pro Ala Ala
                15                  20                  25

TCG CAG GCA CCG GGT CCG TCT CTG CTC GCG CCT CAG CAC GGC CGC CCG            747
Ser Gln Ala Pro Gly Pro Ser Leu Leu Ala Pro Gln His Gly Arg Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 30  |     |     |     | 35  |     |     |     | 40  |     |     |     |     |      |
| TCG | GGC | CCT | GCG | CGG | GGA | GCG | CCT | GGG | CGC | CGG | CCT | CTG | GTC | GTC | CGC | 795  |
| Ser | Gly | Pro | Ala | Arg | Gly | Ala | Pro | Gly | Arg | Arg | Pro | Leu | Val | Val | Arg |      |
|     |     | 45  |     |     |     |     | 50  |     |     |     | 55  |     |     |     |     |      |
| GGA | CTC | GGA | GGC | CTC | CGT | CAG | ATC | CTC | CGT | GTG | CAC | CCC | GCT | GCT | CGA | 843  |
| Gly | Leu | Gly | Gly | Leu | Arg | Gln | Ile | Leu | Arg | Val | His | Pro | Ala | Ala | Arg |      |
|     | 60  |     |     |     |     | 65  |     |     |     |     | 70  |     |     |     |     |      |
| GGC | GCC | CGA | GTC | TTC | CTC | GTC | GGG | GGA | AGA | CAC | CTC | AGA | GTC | AGA | GTG | 891  |
| Gly | Ala | Arg | Val | Phe | Leu | Val | Gly | Gly | Arg | His | Leu | Arg | Val | Arg | Val |      |
| 75  |     |     |     |     | 80  |     |     |     |     | 85  |     |     |     |     | 90  |      |
| TGC | CTC | GGA | CTC | GGA | CGT | GTC | GAT | ATA | GTT | CAC | ACC | CTG | GTG | GCT | CAT | 939  |
| Cys | Leu | Gly | Leu | Gly | Arg | Val | Asp | Ile | Val | His | Thr | Leu | Val | Ala | His |      |
|     |     |     |     | 95  |     |     |     |     | 100 |     |     |     |     | 105 |     |      |
| CGG | GGC | TCG | CCT | CTG | CAT | CCG | CCG | CAT | CCA | CTG | CGC | CGA | TAT | GTC | AAA | 987  |
| Arg | Gly | Ser | Pro | Leu | His | Pro | Pro | His | Pro | Leu | Arg | Arg | Tyr | Val | Lys |      |
|     |     |     | 110 |     |     |     | 115 |     |     |     | 120 |     |     |     |     |      |
| CAG | CGT | ATC | GAC | GAG | GGC | GTG | GGT | GTT | TGC | CCC | AAA | CAT | GGG | GAG | CAT | 1035 |
| Gln | Arg | Ile | Asp | Glu | Gly | Val | Gly | Val | Cys | Pro | Lys | His | Gly | Glu | His |      |
|     |     | 125 |     |     |     |     | 130 |     |     |     |     | 135 |     |     |     |      |
| GGC | CTC | GGT | CAC | GCG | CTG | GCG | GTT | CAT | CCC | GTG | CTC | CTG | GAT | AAT | CTC | 1083 |
| Gly | Leu | Gly | His | Ala | Leu | Ala | Val | His | Pro | Val | Leu | Leu | Asp | Asn | Leu |      |
|     | 140 |     |     |     |     | 145 |     |     |     |     | 150 |     |     |     |     |      |
| GAC | GAT | GTT | GTC | CAC | TAC | GGC | CTC | GCG | GAT | GGG | GTC | GCT | CTC | GAT | GAC | 1131 |
| Asp | Asp | Val | Val | His | Tyr | Gly | Leu | Ala | Asp | Gly | Val | Ala | Leu | Asp | Asp |      |
| 155 |     |     |     |     | 160 |     |     |     |     | 165 |     |     |     |     | 170 |      |
| CGT | CGA | GAC | CTG | CCC | ATA | AAG | CCA | GTT | GAA | GAC | GGG | GAC | TCT | GGG | GCG | 1179 |
| Arg | Arg | Asp | Leu | Pro | Ile | Lys | Pro | Val | Glu | Asp | Gly | Asp | Ser | Gly | Ala |      |
|     |     |     |     | 175 |     |     |     |     | 180 |     |     |     |     | 185 |     |      |
| GGC | GCG | AGA | CCC | AGA | CCC | GGA | GCC | CTG | CCC | TTC | GGC | CTC | CTC | GTG | GCG | 1227 |
| Gly | Ala | Arg | Pro | Arg | Pro | Gly | Ala | Leu | Pro | Phe | Gly | Leu | Leu | Val | Ala |      |
|     |     |     | 190 |     |     |     | 195 |     |     |     | 200 |     |     |     |     |      |
| CAC | CTC | CTC | GGT | ATA | GTC | TTC | ACC | CCA | GAT | GAC | CGC | GAA | GCC | CCC | CCC | 1275 |
| His | Leu | Leu | Gly | Ile | Val | Phe | Thr | Pro | Asp | Asp | Arg | Glu | Ala | Pro | Pro |      |
|     |     | 205 |     |     |     |     | 210 |     |     |     |     | 215 |     |     |     |      |
| TAC | CGG | CTC | ATC | CTC | TTC | CCC | GTC | GAC | ATC | CGT | CGC | CCC | CTC | CAC | GGG | 1323 |
| Tyr | Arg | Leu | Ile | Leu | Phe | Pro | Val | Asp | Ile | Arg | Arg | Pro | Leu | His | Gly |      |
|     | 220 |     |     |     |     | 225 |     |     |     |     | 230 |     |     |     |     |      |
| CGT | CTC | CAC | AAA | CGA | AGC | GTC | GCT | GTC | CAC | GTG | GTG | GAG | GAT | GGA | GGT | 1371 |
| Arg | Leu | His | Lys | Arg | Ser | Val | Ala | Val | His | Val | Val | Glu | Asp | Gly | Gly |      |
| 235 |     |     |     |     | 240 |     |     |     |     | 245 |     |     |     |     | 250 |      |
| GAC | GCG | GGC | ATT | GCA | CAG | CGG | GCA | GGC | GGT | GCT | CGT | CAG | GGT | CCA | GCG | 1419 |
| Asp | Ala | Gly | Ile | Ala | Gln | Arg | Ala | Gly | Gly | Ala | Arg | Gln | Gly | Pro | Ala |      |
|     |     |     |     | 255 |     |     |     |     | 260 |     |     |     |     | 265 |     |      |
| CTG | GAT | GCA | GTC | CAG | ACA | GAA | CTT | GTG | CAT | GCA | CGG | CAG | CGT | CTG | CGC | 1467 |
| Leu | Asp | Ala | Val | Gln | Thr | Glu | Leu | Val | His | Ala | Arg | Gln | Arg | Leu | Arg |      |
|     |     |     | 270 |     |     |     | 275 |     |     |     | 280 |     |     |     |     |      |
| CTC | GGT | GGC | CGC | GAC | GTC | CAG | GCA | GAT | GGG | GCA | GTC | CAT | GAC | GGA | CCA | 1515 |
| Leu | Gly | Gly | Arg | Asp | Val | Gln | Ala | Asp | Gly | Ala | Val | His | Asp | Gly | Pro |      |
|     |     | 285 |     |     |     |     | 290 |     |     |     |     | 295 |     |     |     |      |
| CCA | TCG | TCT | AAC | TCC | CAC | CCG | GGA | CCA | CCG | GGA | CCC | TCG | GGA | CCA | TCT | 1563 |
| Pro | Ser | Ser | Asn | Ser | His | Pro | Gly | Pro | Pro | Gly | Pro | Ser | Gly | Pro | Ser |      |
|     | 300 |     |     |     |     | 305 |     |     |     |     | 310 |     |     |     |     |      |
| ACA | TCC | CAC | CAG | GAC | CCG | CCG | GGA | CCA | CCA | ACA | CCG | TCC | ACC | TCC | CAC | 1611 |
| Thr | Ser | His | Gln | Asp | Pro | Pro | Gly | Pro | Pro | Thr | Pro | Ser | Thr | Ser | His |      |
| 315 |     |     |     |     | 320 |     |     |     |     | 325 |     |     |     |     | 330 |      |
| CAC | CAC | CAT | CAT | CAT | CAA | GGA | CCC | CCA | ACA | TCC | CCA | AGA | CCC | TCT | ACT | 1659 |
| His | His | His | His | His | Gln | Gly | Pro | Pro | Thr | Ser | Pro | Arg | Pro | Ser | Thr |      |
|     |     |     |     | 335 |     |     |     |     | 340 |     |     |     |     | 345 |     |      |
| TCT | TCC | CAC | CAA | GAC | CCT | CCA | GGA | GGA | GGA | CCC | CCA | TCT | GCT | GAG | ACC | 1707 |
| Ser | Ser | His | Gln | Asp | Pro | Pro | Gly | Gly | Gly | Pro | Pro | Ser | Ala | Glu | Thr |      |
|     |     |     |     | 350 |     |     |     |     | 355 |     |     |     |     | 360 |     |      |

| | | | | | | | | | | | | | | | | |
|---|---|---|---|---|---|---|---|---|---|---|---|---|---|---|---|---|
| CAC | CAC | CAC | CAC | CAC | CAA | GAC | CCA | CCA | GGA | GGA | GGA | CCC | CCA | TCC | ACT | 1755 |
| His | His | His | His | His | Gln | Asp | Pro | Pro | Gly | Gly | Gly | Pro | Pro | Ser | Thr | |
| | | 365 | | | | 370 | | | | | | 375 | | | | |
| TCT | TCC | CAT | CAC | CAC | CAC | CAA | GAC | CCT | CCA | GGA | GGA | GGA | CCC | CCG | TCA | 1803 |
| Ser | Ser | His | His | His | His | Gln | Asp | Pro | Pro | Gly | Gly | Gly | Pro | Pro | Ser | |
| | 380 | | | | 385 | | | | | | 390 | | | | | |
| CCC | CCA | CCA | AGA | CCC | TCC | ACC | TCT | TCT | TCT | TCC | TCC | CAC | CAG | GGA | CCC | 1851 |
| Pro | Pro | Pro | Arg | Pro | Ser | Thr | Ser | Ser | Ser | Ser | Ser | His | Gln | Gly | Pro | |
| 395 | | | | | 400 | | | | | 405 | | | | | 410 | |
| CCA | TCC | ACA | AGA | CCA | CCT | CCA | CCC | CAG | AGA | CCA | CCG | CCA | AGA | TGG | CCG | 1899 |
| Pro | Ser | Thr | Arg | Pro | Pro | Pro | Pro | Gln | Arg | Pro | Pro | Pro | Arg | Trp | Pro | |
| | | | | 415 | | | | | 420 | | | | | 425 | | |
| CCT | CCA | TCT | CCC | CAA | AAA | ATC | TCA | GAG | ACT | CGG | GCT | GGT | TCA | GAA | AAT | 1947 |
| Pro | Pro | Ser | Pro | Gln | Lys | Ile | Ser | Glu | Thr | Arg | Ala | Gly | Ser | Glu | Asn | |
| | | | 430 | | | | | 435 | | | | | 440 | | | |
| ACA | GCA | CAA | ACT | TTA | TTT | TCT | CAC | TCT | GAA | AAT | AAA | CTC | TTT | TCT | CAC | 1995 |
| Thr | Ala | Gln | Thr | Leu | Phe | Ser | His | Ser | Glu | Asn | Lys | Leu | Phe | Ser | His | |
| | | 445 | | | | | 450 | | | | | 455 | | | | |
| CCG | ATG | GGA | GAA | GGA | GGA | GAA | GGG | GAC | CGG | GGG | ACC | GCG | GGA | GGA | GAA | 2043 |
| Pro | Met | Gly | Glu | Gly | Gly | Glu | Gly | Asp | Arg | Gly | Thr | Ala | Gly | Gly | Glu | |
| | 460 | | | | | 465 | | | | | 470 | | | | | |
| GGG | GAC | CGG | GAC | GAT | CCT | CGG | CCG | CCG | AGC | CCT | CCG | CCG | CGG | CCG | CCG | 2091 |
| Gly | Asp | Arg | Asp | Asp | Pro | Arg | Pro | Pro | Ser | Pro | Pro | Pro | Arg | Pro | Pro | |
| 475 | | | | | 480 | | | | | 485 | | | | | 490 | |
| CCG | CCG | CTT | CCA | CCA | CCG | CCG | CCA | CCT | CCG | CCG | CCG | CCG | CAG | CCA | CCT | 2139 |
| Pro | Pro | Leu | Pro | Pro | Pro | Pro | Pro | Pro | Pro | Pro | Pro | Pro | Gln | Pro | Pro | |
| | | | | 495 | | | | | 500 | | | | | 505 | | |
| CCG | GCC | GGG | GGA | TCC | GCG | CGG | AGG | AGA | AGG | AGA | GGA | GGA | GGA | GGA | GGG | 2187 |
| Pro | Ala | Gly | Gly | Ser | Ala | Arg | Arg | Arg | Arg | Arg | Gly | Gly | Gly | Gly | Gly | |
| | | | | 510 | | | | | 515 | | | | | 520 | | |
| CCA | CCG | GGC | CGG | GGA | GGC | AGG | CGC | CGG | GGA | GGC | AAG | CGC | CGC | CGG | GCC | 2235 |
| Pro | Pro | Gly | Arg | Gly | Gly | Arg | Arg | Arg | Gly | Gly | Lys | Arg | Arg | Arg | Ala | |
| | | 525 | | | | | 530 | | | | | 535 | | | | |
| GAG | GGG | ACC | GAG | GCC | GCC | GCC | GCG | GAC | GCA | GAG | GAG | GAG | GAG | GAC | GGG | 2283 |
| Glu | Gly | Thr | Glu | Ala | Ala | Ala | Ala | Asp | Ala | Glu | Glu | Glu | Glu | Asp | Gly | |
| | 540 | | | | | 545 | | | | | 550 | | | | | |
| GAC | GAG | GAC | GAG | GAC | GAG | GAC | CGG | GCC | GAG | GAC | GAG | GGG | AGA | GAA | GAC | 2331 |
| Asp | Glu | Asp | Glu | Asp | Glu | Asp | Arg | Ala | Glu | Asp | Glu | Gly | Arg | Glu | Asp | |
| 555 | | | | | 560 | | | | | 565 | | | | | 570 | |
| GGA | GGA | GAA | GGG | CCT | CGA | GGA | GCC | GGT | GGA | GGG | GCC | GGA | GAG | TCA | GAG | 2379 |
| Gly | Gly | Glu | Gly | Pro | Arg | Gly | Ala | Gly | Gly | Gly | Ala | Gly | Glu | Ser | Glu | |
| | | | | 575 | | | | | 580 | | | | | 585 | | |
| TCA | GAG | TCA | GAG | TCC | AGC | CGG | GCC | GAG | GGG | GCG | CCC | CGC | TCA | GCG | GAG | 2427 |
| Ser | Glu | Ser | Glu | Ser | Ser | Arg | Ala | Glu | Gly | Ala | Pro | Arg | Ser | Ala | Glu | |
| | | | 590 | | | | | 595 | | | | | 600 | | | |
| CAG | CAG | GTA | GGG | GTT | GCC | GGC | GTC | CTC | GGC | CTC | CTC | GTC | GTC | CGA | GAT | 2475 |
| Gln | Gln | Val | Gly | Val | Ala | Gly | Val | Leu | Gly | Leu | Leu | Val | Val | Arg | Asp | |
| | | 605 | | | | | 610 | | | | | 615 | | | | |
| GGC | CTC | CAC | CTT | GAT | GGG | CCC | GAG | CGG | GCC | GCG | GGG | CCG | GCC | GTC | GCC | 2523 |
| Gly | Leu | His | Leu | Asp | Gly | Pro | Glu | Arg | Ala | Ala | Gly | Pro | Ala | Val | Ala | |
| | | 620 | | | | | 625 | | | | | 630 | | | | |
| GCC | GCG | GAA | GCC | GAC | GAT | CTC | CAC | CGC | GGC | AGA | GTC | CTC | CCC | GTC | CTC | 2571 |
| Ala | Ala | Glu | Ala | Asp | Asp | Leu | His | Arg | Gly | Arg | Val | Leu | Pro | Val | Leu | |
| 635 | | | | | 640 | | | | | 645 | | | | | 650 | |
| GCC | GGG | CCC | CCG | GGC | GCC | CGA | GGG | CCG | GTG | GGT | CTC | CAC | GGC | GCC | GCC | 2619 |
| Ala | Gly | Pro | Pro | Gly | Ala | Arg | Gly | Pro | Val | Gly | Leu | His | Gly | Ala | Ala | |
| | | | | 655 | | | | | 660 | | | | | 665 | | |
| GGC | GGC | GGC | GCG | GAC | GCT | GGT | CTC | GAA | GGG | CGC | AAA | GTC | CCA | GCG | CAC | 2667 |
| Gly | Gly | Gly | Ala | Asp | Ala | Gly | Leu | Glu | Gly | Arg | Lys | Val | Pro | Ala | His | |
| | | | 670 | | | | | 675 | | | | | 680 | | | |
| GGC | CGG | CGG | GGC | GCC | CGC | GGC | CGC | GAG | GGC | GCC | CGG | GGC | CAG | CAC | CAG | 2715 |
| Gly | Arg | Arg | Gly | Ala | Arg | Gly | Arg | Glu | Gly | Ala | Arg | Gly | Gln | His | Gln | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 685 |     |     |     |     | 690 |     |     |     |     |     | 695 |     |     |      |
| CGG | GGC | GGC | CTC | GGC | GTC | GGG | CTC | CAG | CAG | CGC | CGC | GGC | GCA | GAA | GGC | 2763 |
| Arg | Gly | Gly | Leu | Gly | Val | Gly | Leu | Gln | Gln | Arg | Arg | Gly | Ala | Glu | Gly |      |
|     | 700 |     |     |     | 705 |     |     |     |     | 710 |     |     |     |     |     |      |
| GCG | CAG | CTC | GGC | CGG | CAG | GCC | CTC | GGG | GCC | GCG | GAG | CTC | GGC | GAG | GCC | 2811 |
| Ala | Gln | Leu | Gly | Arg | Gln | Ala | Leu | Gly | Ala | Ala | Glu | Leu | Gly | Glu | Ala |      |
| 715 |     |     |     |     | 720 |     |     |     |     | 725 |     |     |     |     | 730 |      |
| CCG | GCG | GCC | GCA | GGA | GAC | GAA | GAC | GGG | CCG | CAG | CGG | GGC | GCC | GAG | CCC | 2859 |
| Pro | Ala | Ala | Ala | Gly | Asp | Glu | Asp | Gly | Pro | Gln | Arg | Gly | Ala | Glu | Pro |      |
|     |     |     |     | 735 |     |     |     |     | 740 |     |     |     |     | 745 |     |      |
| CCA | GCG | GTT | GGC | CGC | GCG | GTG | CCC | GAA | GGC | GGC | GCC | CGC | GTC | AAA | GTC | 2907 |
| Pro | Ala | Val | Gly | Arg | Ala | Val | Pro | Glu | Gly | Gly | Ala | Arg | Val | Lys | Val |      |
|     |     |     | 750 |     |     |     |     | 755 |     |     |     |     | 760 |     |     |      |
| CGG | GTC | CCC | GAG | CCC | GAG | CGC | GGA | GCG | CTG | GCG | GGC | CAT | GTC | CTT | GCA | 2955 |
| Arg | Val | Pro | Glu | Pro | Glu | Arg | Gly | Ala | Leu | Ala | Gly | His | Val | Leu | Ala |      |
|     | 765 |     |     |     |     | 770 |     |     |     |     | 775 |     |     |     |     |      |
| GCC | GTC | CAC | GGT | GGG | GAG | CAC | GCG | CTC | GCG | GTA | GGC | GCG | CGG | CGG | CAG | 3003 |
| Ala | Val | His | Gly | Gly | Glu | His | Ala | Leu | Ala | Val | Gly | Ala | Arg | Arg | Gln |      |
| 780 |     |     |     |     | 785 |     |     |     |     | 790 |     |     |     |     |     |      |
| CGG | GAC | CGG | GGT | CCG | GGG | CCC | GGC | GCG | GGT | GCT | CAC | CGT | GTA | GCG | CAC | 3051 |
| Arg | Asp | Arg | Gly | Pro | Gly | Pro | Gly | Ala | Gly | Ala | His | Arg | Val | Ala | His |      |
| 795 |     |     |     |     | 800 |     |     |     |     | 805 |     |     |     |     | 810 |      |
| GTT | GTC | CTG | GCG | GCA | GAG | GCG | CAG | CGG | CTC | GGC | CCC | GGG | GTG | CAG | GCG | 3099 |
| Val | Val | Leu | Ala | Ala | Glu | Ala | Gln | Arg | Leu | Gly | Pro | Gly | Val | Gln | Ala |      |
|     |     |     |     | 815 |     |     |     |     | 820 |     |     |     |     | 825 |     |      |
| GGC | GAA | GGA | GGC | CTC | CAC | GCG | GGC | GAA | GCA | GGC | CGG | GCC | CAC | GAT | GGA | 3147 |
| Gly | Glu | Gly | Gly | Leu | His | Ala | Gly | Glu | Ala | Gly | Arg | Ala | His | Asp | Gly |      |
|     |     |     | 830 |     |     |     |     | 835 |     |     |     |     | 840 |     |     |      |
| GCT | CGA | GTC | CAG | GAC | GGC | CGC | GCG | GAG | CTC | GCG | GCA | CTC | GGG | CCA | GCG | 3195 |
| Ala | Arg | Val | Gln | Asp | Gly | Arg | Ala | Glu | Leu | Ala | Ala | Leu | Gly | Pro | Ala |      |
|     |     | 845 |     |     |     |     | 850 |     |     |     |     | 855 |     |     |     |      |
| CAC | GGC | GCA | CTG | GGC | GGC | CGG | GTC | CAG | GCG | GGC | GCG | GAC | GTA | GAC | GTG | 3243 |
| His | Gly | Ala | Leu | Gly | Gly | Arg | Val | Gln | Ala | Gly | Ala | Asp | Val | Asp | Val |      |
|     | 860 |     |     |     |     | 865 |     |     |     |     | 870 |     |     |     |     |      |
| GTA | GTC | CCC | CAC | GGC | CGG | GCC | GTC | CGC | GGG | CCA | GTC | CTC | GAT | GGT | GTC | 3291 |
| Val | Val | Pro | His | Gly | Arg | Ala | Val | Arg | Gly | Pro | Val | Leu | Asp | Gly | Val |      |
| 875 |     |     |     |     | 880 |     |     |     |     | 885 |     |     |     |     | 890 |      |
| CAG | CAC | GAT | GAG | CCG | GCG | CCG | CGC | CGC | GCC | GAG | CCG | CGA | GCA | GAG | GTA | 3339 |
| Gln | His | Asp | Glu | Pro | Ala | Pro | Arg | Arg | Ala | Glu | Pro | Arg | Ala | Glu | Val |      |
|     |     |     |     | 895 |     |     |     |     | 900 |     |     |     |     | 905 |     |      |
| CTC | GAC | GGC | GCC | GGC | GAA | GCC | GAG | GTC | CCG | CGC | CGA | GAG | CAG | CAG | CAC | 3387 |
| Leu | Asp | Gly | Ala | Gly | Glu | Ala | Glu | Val | Pro | Arg | Arg | Glu | Gln | Gln | His |      |
|     |     |     | 910 |     |     |     |     | 915 |     |     |     |     | 920 |     |     |      |
| CCC | CTG | GGC | GTT | GAG | GCG | GCC | GAT | GTC | GGG | GCG | CCC | GGT | CCA | GTT | CCC | 3435 |
| Pro | Leu | Gly | Val | Glu | Ala | Ala | Asp | Val | Gly | Ala | Pro | Gly | Pro | Val | Pro |      |
|     |     | 925 |     |     |     |     | 930 |     |     |     |     | 935 |     |     |     |      |
| GGC | CCA | GGC | GTG | CGA | GTC | CGG | CGT | GCA | GAG | GCG | GTG | GGC | GAA | GGC | GGC | 3483 |
| Gly | Pro | Gly | Val | Arg | Val | Arg | Arg | Ala | Glu | Ala | Val | Gly | Glu | Gly | Gly |      |
|     | 940 |     |     |     |     | 945 |     |     |     |     | 950 |     |     |     |     |      |
| GAG | CAG | CGC | CGA | GAG | GCC | GCC | GCG | GCG | CGG | GTC | CCA | GGC | CGG | GCG | CGG | 3531 |
| Glu | Gln | Arg | Arg | Glu | Ala | Ala | Ala | Ala | Arg | Val | Pro | Gly | Arg | Ala | Arg |      |
| 955 |     |     |     |     | 960 |     |     |     |     | 965 |     |     |     |     | 970 |      |
| GGC | GCC | CTC | GGC | GGG | CTC | GGC | GCA | GAG | CTC | CTC | GTG | GGG | CAG | CGG | GTC | 3579 |
| Gly | Ala | Leu | Gly | Gly | Leu | Gly | Ala | Glu | Leu | Leu | Val | Gly | Gln | Arg | Val |      |
|     |     |     |     | 975 |     |     |     |     | 980 |     |     |     |     | 985 |     |      |
| GTA | GAG | CAC | CAC | CAC | GCG | CAC | GTC | CTC | GGG | GTC | GGC | TAT | CTG | CCG | CAT | 3627 |
| Val | Glu | His | His | His | Ala | His | Val | Leu | Gly | Val | Gly | Tyr | Leu | Pro | His |      |
|     |     |     | 990 |     |     |     |     | 995 |     |     |     |     | 1000|     |     |      |
| CCA | GGC | GGC | GCG | GCG | GCG | GAG | CGG | GGC | GCC | CGC | GGC | CCC | GCG | GCG | CGC | 3675 |
| Pro | Gly | Gly | Ala | Ala | Ala | Glu | Arg | Gly | Ala | Arg | Gly | Pro | Ala | Ala | Arg |      |
|     |     |     |     | 1005|     |     |     |     | 1010|     |     |     |     | 1015|     |      |

-continued

| | |
|---|---|
| GGC GAT GTG CGC CAG GGC GGC CGG GTC GAA GGT GAG CGC CGG GCG CCA<br>Gly Asp Val Arg Gln Gly Gly Arg Val Glu Gly Glu Arg Arg Ala Pro<br>     1020                           1025                      1030 | 3723 |
| GAG TTC GGG GAA GAC CTC CTG GTC CAC GAG GGC GCG GGC CAC CTC GGG<br>Glu Phe Gly Glu Asp Leu Leu Val His Glu Gly Ala Gly His Leu Gly<br>1035                       1040                     1045                     1050 | 3771 |
| CGG GCA GTA GGC GGC GAG GGC CGC GGC GGA GGG CCG CGG CGT GTG GGT<br>Arg Ala Val Gly Gly Glu Gly Arg Gly Gly Gly Pro Arg Arg Val Gly<br>                         1055                     1060                   1065 | 3819 |
| CTC GCC GGC CGG GAC GCG GCG GAA GCC GCC GTC GGG CGC GGG GTG CTC<br>Leu Ala Gly Arg Asp Ala Ala Glu Ala Ala Val Gly Arg Gly Val Leu<br>                 1070                     1075                   1080 | 3867 |
| GGG CAT GGG CCC GAG CGG GCG CCG GAG CCG GTC GTC CTC GGA GGA GGA<br>Gly His Gly Pro Glu Arg Ala Pro Glu Pro Val Val Leu Gly Gly Gly<br>          1085                     1090                     1095 | 3915 |
| GGA GGA GGA GGA GGA GGA CAC GAG CGC GGG AGC GGG GTC CGG AGC GGG<br>Gly Gly Gly Gly Gly Gly His Glu Arg Gly Ser Gly Val Arg Ser Gly<br>        1100                     1105                    1110 | 3963 |
| CCC GAG TCC GAG GGA GCG GCG CTT GCG CCG GGG CCC CCG GTC CTC TTC<br>Pro Glu Ser Glu Gly Ala Ala Leu Ala Pro Gly Pro Pro Val Leu Phe<br>1115                     1120                     1125                     1130 | 4011 |
| GTC GTC GCG GTG GCC GTG GCC GTC CCC GCG GAG GGC CGA GCC GGA GAG<br>Val Val Ala Val Ala Val Ala Val Pro Ala Glu Gly Arg Ala Gly Glu<br>                              1135                    1140                    1145 | 4059 |
| CCC CTC GTC CTC CTC GCC GTC CCC GGG GCG GCG GGC CCC GGG CGC GCG<br>Pro Leu Val Leu Leu Ala Val Pro Gly Ala Ala Gly Pro Gly Arg Ala<br>                 1150                     1155                   1160 | 4107 |
| GCG CTT CTT CTT GCG CCG CTC GGG CGC TGG GTC CGG GCC GGC GGC GGG<br>Ala Leu Leu Leu Ala Pro Leu Gly Arg Trp Val Arg Ala Gly Gly Gly<br>         1165                     1170                    1175 | 4155 |
| GGA GCT GGC GTA GCC GGA GGA GCC GGA GAG GCC GGA CTT GGT GCC GGA<br>Gly Ala Gly Val Ala Gly Gly Ala Gly Glu Ala Gly Leu Gly Ala Gly<br>                 1180                     1185                   1190 | 4203 |
| GCT GGA CTT GGT GCT GGA GCC GGA CTT GGT GCT GGC GGG GCT GGA GGG<br>Ala Gly Leu Gly Ala Gly Ala Gly Leu Gly Ala Gly Gly Ala Gly Gly<br>1195                     1200                     1205                     1210 | 4251 |
| CCC GGA GCC GGG GAG GCC GGA GGG GGC GCC CGC CGC CGC CGG CGC CGG<br>Pro Gly Ala Gly Glu Ala Gly Gly Gly Ala Arg Arg Arg Arg Arg Arg<br>                         1215                     1220                   1225 | 4299 |
| CGC TGG GAC GAC GAG GCC GGG CTG CTC GGG CCA GAG CGG GGG CAG GCC<br>Arg Trp Asp Asp Glu Ala Gly Leu Leu Gly Pro Glu Arg Gly Gln Ala<br>                 1230                     1235                   1240 | 4347 |
| GGG CGC GGG CTC CGC GGG CCC GGG CCG CGC GGC GGC CTC GGC GAG CCG<br>Gly Arg Gly Leu Arg Gly Pro Gly Pro Arg Gly Gly Leu Gly Glu Pro<br>             1245                     1250                    1255 | 4395 |
| GGC CCC GGC CAC GTT GGC CGG GGC GAA GAG GGC CGC GGC GTA GGT CCA<br>Gly Pro Gly His Val Gly Arg Gly Glu Glu Gly Arg Gly Val Gly Pro<br>         1260                     1265                    1270 | 4443 |
| GGC GGC CTC GCG GGC GCG GGC CCC GTC CAC GCT GTA GCG CAC CAG CGG<br>Gly Gly Leu Ala Gly Ala Gly Pro Val His Ala Val Ala His Gln Arg<br>1275                     1280                     1285                     1290 | 4491 |
| CGC CAC GGT GCG GGC GAC GAG GGC GAC AGA GTC CGC GGC CTG CTG CCG<br>Arg His Gly Ala Gly Asp Glu Gly Asp Arg Val Arg Gly Leu Leu Pro<br>                         1295                     1300                    1305 | 4539 |
| CTC GGC CGG GCC GGC CCC GGG GAT CGC GTC GCG GAG CGC GAG CAG CGC<br>Leu Gly Arg Ala Gly Pro Gly Asp Arg Val Ala Glu Arg Glu Gln Arg<br>                 1310                     1315                   1320 | 4587 |
| GGC GGT CAC CTC CTC GAG GCA GGC GGG CCC GAG GGC GGC CGG GGC GCG<br>Gly Gly His Leu Leu Glu Ala Gly Gly Pro Glu Gly Gly Arg Gly Ala<br>             1325                     1330                    1335 | 4635 |
| GGC GGG CGC GGG CAG CCG GAG CGG GCA GGG CAG CAG GCG CTC GAG GAC<br>Gly Gly Arg Gly Gln Pro Glu Arg Ala Gly Gln Gln Ala Leu Glu Asp | 4683 |

-continued

|     | 1340 |     |     |     | 1345 |     |     |     | 1350 |     |     |     |     |     |     |      |
|-----|------|-----|-----|-----|------|-----|-----|-----|------|-----|-----|-----|-----|-----|-----|------|
| GCC | GCG  | GCA | GGC | CAG | GAC  | GCA | GGC | GTC | CGC  | CAG | CTC | GCG | GGG | CAC | GCG | 4731 |
| Ala | Ala  | Ala | Gly | Gln | Asp  | Ala | Gly | Val | Arg  | Gln | Leu | Ala | Gly | His | Ala |      |
| 1355|      |     |     | 1360|      |     |     | 1365|      |     |     | 1370|     |     |     |      |
| GCC | GGG  | CTG | CGC | GGC | GGC  | GAA | GGC | GGC | GCG  | GAC | GCG | GGC | GCA | GAG | GGC | 4779 |
| Ala | Gly  | Leu | Arg | Gly | Gly  | Glu | Gly | Gly | Ala  | Asp | Ala | Gly | Ala | Glu | Gly |      |
|     |      |     |     | 1375|      |     |     |     | 1380 |     |     |     | 1385|     |     |      |
| CTC | GAC  | GGT | CGC | CTC | CCC  | GGC | GCG | GGG | GTC  | CGC | GGC | GCG | GCC | CGG | GTA | 4827 |
| Leu | Asp  | Gly | Arg | Leu | Pro  | Gly | Ala | Gly | Val  | Arg | Gly | Ala | Ala | Arg | Val |      |
|     |      |     |     | 1390|      |     |     | 1395|      |     |     | 1400|     |     |     |      |
| GGC | CAT  | GTC | GGC | GTA | GGC  | CCG | GCG | GAG | GCT  | CTG | CAG | GAT | GAA | GGT | CTT | 4875 |
| Gly | His  | Val | Gly | Val | Gly  | Pro | Ala | Glu | Ala  | Leu | Gln | Asp | Glu | Gly | Leu |      |
|     |      | 1405|     |     |      | 1410|     |     |      | 1415|     |     |     |     |     |      |
| CTG | GGT  | GCG | ATC | GTA | GCG  | GCG | GCT | CAT | GGC  | CAC | GGC | GCT | CAC | CGC | GTG | 4923 |
| Leu | Gly  | Ala | Ile | Val | Ala  | Ala | Ala | His | Gly  | His | Gly | Ala | His | Arg | Val |      |
|     | 1420 |     |     |     |      | 1425|     |     |      |     | 1430|     |     |     |     |      |
| CGG | CAG  | GGC | CCA | GAG | CGG  | GTC | CTG | GGC | GGC  | CAT | GGC | GTC | CCC | GAT | GTG | 4971 |
| Arg | Gln  | Gly | Pro | Glu | Arg  | Val | Leu | Gly | Gly  | His | Gly | Val | Pro | Asp | Val |      |
| 1435|      |     |     |     | 1440 |     |     |     |      | 1445|     |     |     |     | 1450|      |
| CGG | CAG  | CGG | CGG | GGT | CAC  | GCT | GCC | GGT | GAT  | GAA | GGA | GCC | GTG | GCC | GTG | 5019 |
| Arg | Gln  | Arg | Arg | Gly | His  | Ala | Ala | Gly | Asp  | Glu | Gly | Ala | Val | Ala | Val |      |
|     |      |     |     |     | 1455 |     |     |     |      | 1460|     |     |     | 1465|     |      |
| GGG | CGC  | GTG | GAC | CCG | GCG  | CTG | GCA | GAA | CTG  | GTT | GAA | GCG | CTG | GTC | GGG | 5067 |
| Gly | Arg  | Val | Asp | Pro | Ala  | Leu | Ala | Glu | Leu  | Val | Glu | Ala | Leu | Val | Gly |      |
|     |      |     |     | 1470|      |     |     |     | 1475 |     |     |     | 1480|     |     |      |
| GGC | CTG  | CAT | CCG | CGG | GTT  | CTG | CAG | CCA | GGA  | CAT | GGC | CTC | GCC | GGC | GGC | 5115 |
| Gly | Leu  | His | Pro | Arg | Val  | Leu | Gln | Pro | Gly  | His | Gly | Leu | Ala | Gly | Gly |      |
|     |      |     |     | 1485|      |     |     |     | 1490 |     |     |     | 1495|     |     |      |
| CCC | GCT  | GTA | GAT | GAG | GCG  | CAC | GAG | GGC | CTC  | GTG | CTG | CTT | CCT | CGA | GTC | 5163 |
| Pro | Ala  | Val | Asp | Glu | Ala  | His | Glu | Gly | Leu  | Val | Leu | Leu | Pro | Arg | Val |      |
|     |      | 1500|     |     |      | 1505|     |     |      |     | 1510|     |     |     |     |      |
| CCC | CAT  | CTC | CGG | GAT | GAA  | GAC | GGG | CAC | GGG  | CCC | GGC | CGC | GGC | GCG | GTA | 5211 |
| Pro | His  | Leu | Arg | Asp | Glu  | Asp | Gly | His | Gly  | Pro | Gly | Arg | Gly | Ala | Val |      |
| 1515|      |     |     |     | 1520 |     |     |     |      | 1525|     |     |     |     | 1530|      |
| GCG | GGC  | CGC | GGC | CTG | GCG  | GAC | GTC | GTC | CTC  | GTC | CCA | GAG | CCC | CTC | GCG | 5259 |
| Ala | Gly  | Arg | Gly | Leu | Ala  | Asp | Val | Val | Leu  | Val | Pro | Glu | Pro | Leu | Ala |      |
|     |      |     |     | 1535|      |     |     |     | 1540 |     |     |     | 1545|     |     |      |
| GGA | GTC  | CCC | GGC | GCC | GCC  | GTA | GCG | GAC | GCG  | GCC | GTC | GGC | CGG | AGG | GTC | 5307 |
| Gly | Val  | Pro | Gly | Ala | Ala  | Val | Ala | Asp | Ala  | Ala | Val | Gly | Arg | Arg | Val |      |
|     |      |     | 1550|     |      |     |     | 1555|     |     |     | 1560|     |     |     |      |
| GGA | GCC  | GGG | CCA | GGG | CTC  | CCC | GAG | CGG | GGT  | GAG | CAG | CGG | CCC | GTC | GGT | 5355 |
| Gly | Ala  | Gly | Pro | Gly | Leu  | Pro | Glu | Arg | Gly  | Glu | Gln | Arg | Pro | Val | Gly |      |
|     |      | 1565|     |     |      | 1570|     |     |      |     | 1575|     |     |     |     |      |
| CGG | CGG  | GGG | CCC | GTC | GGC  | CAT | GAG | CGA | GAG  | GTG | GTT | GTT | GGT | GGA | GCG | 5403 |
| Arg | Arg  | Gly | Pro | Val | Gly  | His | Glu | Arg | Glu  | Val | Val | Val | Gly | Gly | Ala |      |
|     | 1580 |     |     |     |      | 1585|     |     |      |     | 1590|     |     |     |     |      |
| GCG | CTT  | CCT | GCG | CGG | GGG  | CCG | GGC | GGG | CTC  | CGG | GGC | CGG | GGC | CGG | GGA | 5451 |
| Ala | Leu  | Pro | Ala | Arg | Gly  | Pro | Gly | Gly | Leu  | Arg | Gly | Arg | Gly | Arg | Gly |      |
| 1595|      |     |     |     | 1600 |     |     |     |      | 1605|     |     |     |     | 1610|      |
| GGC | CGC  | GGC | GGA | GGA | GGA  | GGT | GGC | GGA | GGA  | GGA | GGC | CGA | GGG | CCG |     | 5499 |
| Gly | Arg  | Gly | Gly | Gly | Gly  | Gly | Gly | Gly | Gly  | Gly | Gly | Arg | Gly | Pro |     |      |
|     |      |     |     | 1615|      |     |     |     | 1620 |     |     |     | 1625|     |     |      |
| CGG | GGC  | CGC | GGC | GGG | CGC  | CGG | CGG | AGA | CGG  | TGG | CGG | CCC | GGC | GCG | GGC | 5547 |
| Arg | Gly  | Arg | Gly | Gly | Arg  | Arg | Arg | Arg | Arg  | Trp | Arg | Pro | Gly | Ala | Gly |      |
|     |      |     |     |     | 1630 |     |     |     |      | 1635|     |     |     |     | 1640|      |
| GAG | TGG  | GGC | GCC | GGG | CCG  | GAC | TCC | TTC | GTC  | TTC | TTC | TCC | CTC | GGA | GGA | 5595 |
| Glu | Trp  | Gly | Ala | Gly | Pro  | Asp | Ser | Phe | Val  | Phe | Phe | Ser | Leu | Gly | Gly |      |
|     |      |     | 1645|     |      |     |     | 1650|     |     |     | 1655|     |     |     |      |
| GGA | CGA  | GGA | CGA | GGA | GGA  | CGA | GGA | GGA | CGA  | GGA | CGA | GGA | GGC | CGA |     | 5643 |
| Gly | Arg  | Gly | Arg | Gly | Gly  | Arg | Gly | Gly | Arg  | Gly | Arg | Gly | Gly | Arg |     |      |
|     | 1660 |     |     |     |      | 1665|     |     |      |     | 1670|     |     |     |     |      |

-continued

| | | | | | | | | | | | | | | | | |
|---|---|---|---|---|---|---|---|---|---|---|---|---|---|---|---|---|
| GCG | CCG | CGC | GGC | GGC | GGC | GGC | GGC | GGC | GGG | GGC | CCG | GGG | GGC | GGA | GGG | 5691 |
| Ala | Pro | Arg | Gly | Gly | Gly | Gly | Gly | Gly | Gly | Gly | Pro | Gly | Gly | Gly | Gly | |
| 1675 | | | | | 1680 | | | | | 1685 | | | | | 1690 | |

| | | | | | | | | | | | | | | | | |
|---|---|---|---|---|---|---|---|---|---|---|---|---|---|---|---|---|
| CGA | GCG | GGC | CGG | GGA | GAG | GTC | CGA | GTC | GCT | GCC | GCC | GCT | GCT | GGA | GCT | 5739 |
| Arg | Ala | Gly | Arg | Gly | Glu | Val | Arg | Val | Ala | Ala | Ala | Ala | Ala | Gly | Ala | |
| | | | | 1695 | | | | | 1700 | | | | | 1705 | | |

| | | | | | | | | | | | | | | | | |
|---|---|---|---|---|---|---|---|---|---|---|---|---|---|---|---|---|
| GCT | GAA | GCC | GCG | GCC | GCG | GCG | GAG | GGC | GCC | CTC | TCC | GGC | GCG | GCG | CCG | 5787 |
| Ala | Glu | Ala | Ala | Ala | Ala | Ala | Glu | Gly | Ala | Leu | Ser | Gly | Ala | Ala | Pro | |
| | | | 1710 | | | | | 1715 | | | | | 1720 | | | |

| | | | | | | | | | | | | | | | | |
|---|---|---|---|---|---|---|---|---|---|---|---|---|---|---|---|---|
| GCG | GGG | CTG | TCT | CTG | CAG | GGG | CGC | CCC | GCC | GTC | CCC | GGC | GAG | GCC | GAG | 5835 |
| Ala | Gly | Leu | Ser | Leu | Gln | Gly | Arg | Pro | Ala | Val | Pro | Gly | Glu | Ala | Glu | |
| | | 1725 | | | | | 1730 | | | | | 1735 | | | | |

| | | | | | | | | | | | | | | | | |
|---|---|---|---|---|---|---|---|---|---|---|---|---|---|---|---|---|
| TCC | GTC | CTC | GTC | CTT | CTC | GGG | GCC | GCG | GGC | GAC | GGG | CTC | GAC | GGC | GAC | 5883 |
| Ser | Val | Leu | Val | Leu | Leu | Gly | Ala | Ala | Gly | Asp | Gly | Leu | Asp | Gly | Asp | |
| | 1740 | | | | | 1745 | | | | | 1750 | | | | | |

| | | | | | | | | | | | | | | | | |
|---|---|---|---|---|---|---|---|---|---|---|---|---|---|---|---|---|
| GGT | GGT | GGT | GGA | GCT | GGA | GCT | GGA | GTT | GGG | GTT | GGA | GGA | GAC | GGG | GCT | 5931 |
| Gly | Gly | Gly | Gly | Ala | Gly | Ala | Gly | Val | Gly | Val | Gly | Gly | Asp | Gly | Ala | |
| 1755 | | | | | 1760 | | | | | 1765 | | | | | 1770 | |

| | | | | | | | | | | | | | | | | |
|---|---|---|---|---|---|---|---|---|---|---|---|---|---|---|---|---|
| CCG | GGC | GCC | AAG | CGG | CCG | AGG | ATC | GAG | CCG | CCT | CGC | GGC | GGC | GGG | CTC | 5979 |
| Pro | Gly | Ala | Lys | Arg | Pro | Arg | Ile | Glu | Pro | Pro | Arg | Gly | Gly | Gly | Leu | |
| | | | 1775 | | | | | 1780 | | | | | 1785 | | | |

| | | | | | | | | | | | | | | | | |
|---|---|---|---|---|---|---|---|---|---|---|---|---|---|---|---|---|
| GTC | GAG | CAG | GGG | CTC | GCG | GTG | CTG | GTG | ATG | GTG | ACG | ACC | GCG | GTC | CCC | 6027 |
| Val | Glu | Gln | Gly | Leu | Ala | Val | Leu | Val | Met | Val | Thr | Thr | Ala | Val | Pro | |
| | | | 1790 | | | | | 1795 | | | | | 1800 | | | |

| | | | | | | | | | | | | | | | | |
|---|---|---|---|---|---|---|---|---|---|---|---|---|---|---|---|---|
| TCC | GCC | GGA | GGG | GGC | GCC | GCC | GCC | GCC | GGG | CGC | CGA | GAC | CGG | CCC | GGC | 6075 |
| Ser | Ala | Gly | Gly | Gly | Ala | Ala | Ala | Ala | Gly | Arg | Arg | Asp | Arg | Pro | Gly | |
| | | | | 1805 | | | | | 1810 | | | | | 1815 | | |

| | | | | | | | | | | | | | | | | |
|---|---|---|---|---|---|---|---|---|---|---|---|---|---|---|---|---|
| GGC | GGG | GGA | GGC | TGG | GGA | AGC | GGG | CCC | CCG | CCG | TGC | CGG | CGC | TGC | GGC | 6123 |
| Gly | Gly | Gly | Gly | Trp | Gly | Ser | Gly | Pro | Pro | Pro | Cys | Arg | Arg | Cys | Gly | |
| | | 1820 | | | | | 1825 | | | | | 1830 | | | | |

| | | | | | | | | | | | | | | | | |
|---|---|---|---|---|---|---|---|---|---|---|---|---|---|---|---|---|
| CAC | CGC | TGC | TGG | CTG | TGC | TGG | TGG | CGC | CGG | GGT | CCG | AGG | CCG | CGC | CGC | 6171 |
| His | Arg | Cys | Trp | Leu | Cys | Trp | Trp | Arg | Arg | Gly | Pro | Arg | Pro | Arg | Arg | |
| 1835 | | | | | 1840 | | | | | 1845 | | | | | 1850 | |

| | | | | | | | | | | | | | | | | |
|---|---|---|---|---|---|---|---|---|---|---|---|---|---|---|---|---|
| CGG | CCC | GGG | CTC | ACC | GAC | CGG | GTC | CCC | CCT | CGC | GGG | GGA | CCA | TCT | CCG | 6219 |
| Arg | Pro | Gly | Leu | Thr | Asp | Arg | Val | Pro | Pro | Arg | Gly | Gly | Pro | Ser | Pro | |
| | | | | 1855 | | | | | 1860 | | | | | 1865 | | |

| | | | | | | | | | | | | | | | | |
|---|---|---|---|---|---|---|---|---|---|---|---|---|---|---|---|---|
| CGG | GGC | CGC | CGA | GGG | GCC | GGG | GGA | GCC | GGA | GGA | GCC | GGA | GGA | GCC | GGA | 6267 |
| Arg | Gly | Arg | Arg | Gly | Ala | Gly | Gly | Ala | Gly | Gly | Ala | Gly | Gly | Ala | Gly | |
| | | | 1870 | | | | | 1875 | | | | | 1880 | | | |

| | | | | | | | | | | | | | | | | |
|---|---|---|---|---|---|---|---|---|---|---|---|---|---|---|---|---|
| GGA | GGA | GGA | GGC | CGG | GGA | GGC | TGC | GGA | GGG | GGA | CGA | GCG | CCC | GGG | GCC | 6315 |
| Gly | Gly | Gly | Gly | Arg | Gly | Gly | Cys | Gly | Gly | Gly | Arg | Ala | Pro | Gly | Ala | |
| | | 1885 | | | | | 1890 | | | | | 1895 | | | | |

| | | | | | | | | | | | | | | | | |
|---|---|---|---|---|---|---|---|---|---|---|---|---|---|---|---|---|
| GCC | GGG | GGC | CCC | GGC | CTC | TGC | CGC | TGC | GAG | TGC | TGC | CGG | GGT | CGG | CGG | 6363 |
| Ala | Gly | Gly | Pro | Gly | Leu | Cys | Arg | Cys | Glu | Cys | Cys | Arg | Gly | Arg | Arg | |
| 1900 | | | | | 1905 | | | | | 1910 | | | | | | |

| | | | | | | | | | | | | | | | | |
|---|---|---|---|---|---|---|---|---|---|---|---|---|---|---|---|---|
| CCG | GGG | CCC | GGA | GCC | GGC | CCG | GGA | CCG | GGG | CCC | GAG | GAC | GAG | GTG | ACC | 6411 |
| Pro | Gly | Pro | Gly | Ala | Gly | Pro | Gly | Pro | Gly | Pro | Glu | Asp | Glu | Val | Thr | |
| 1915 | | | | | 1920 | | | | | 1925 | | | | | 1930 | |

| | | | | | | | | | | | | | | | | |
|---|---|---|---|---|---|---|---|---|---|---|---|---|---|---|---|---|
| GTG | CTC | GGA | GCC | CTG | ATG | GAG | AGC | CCG | ACC | GGG | GGA | CCC | GGC | GGC | CGG | 6459 |
| Val | Leu | Gly | Ala | Leu | Met | Glu | Ser | Pro | Thr | Gly | Gly | Pro | Gly | Gly | Arg | |
| | | | | 1935 | | | | | 1940 | | | | | 1945 | | |

| | | | | | | | | | | | |
|---|---|---|---|---|---|---|---|---|---|---|---|
| GGA | CCC | GGG | CTC | GTC | CTC | CTC | CTC | GTC | TTC | GTC | GTC | TAGCACCACG | 6505 |
| Gly | Pro | Gly | Leu | Val | Leu | Leu | Leu | Val | Phe | Val | Val | | |
| | | | 1950 | | | | | 1955 | | | | | |

| | | | | |
|---|---|---|---|---|
| ATCTCGCCCG | AGCCCGGCG | GGCGTGCCGC | TGCTGCTGGG | CCGAAGGAGG | ACGGGCGGC | 6565 |
| CTCGTGGCTC | CGGCCGCGGC | CGCGAGGACG | GCGGCCTCGG | CCTCGGCGGC | GTCGTCGGAG | 6625 |
| AAGAGGCCGC | CCGGGCCGAA | GAGGAGATCC | TCGCCGGAGG | AGCCGCGGCG | CCGGGAGCCC | 6685 |
| TGGCTGCCGC | CGTCGGGGCC | GGACGCGATG | CCCTCTTCCT | CGGCCGCGGC | GGCGGCGGCC | 6745 |
| GCCAGGAGCT | GGCTGAAGTT | GCCCTCGGTC | TCGATGAAGT | CAAAGAGATC | GTCGGCCATG | 6805 |

| | | | | | |
|---|---|---|---|---|---|
| GTCTCGATCG | GGGTCTTTCT | GCCTGAGCGA | GGCCGGGCGC | CGAGCGCGGA | GAGCGGGCGG | 6865 |
| CGGAGAAGAA | GGAGGAAGGC | GGCCGGAGGA | GGAGAAGAAG | ACTCTTCTCT | GGTGGGCCGA | 6925 |
| GAGCCTCTGT | GGGTCGGGCG | TCCGTCGAGG | GCTGATAGCC | GCCGGAGAGC | CGGAGTCTTC | 6985 |
| AGAGTCCGCG | CCGGAGCGGA | GACGATCGGA | TCCCCTCGGG | TTGGCAGAGA | ACGATGCTGT | 7045 |
| CCGTACCTGC | ACCGCAGTGA | AGTGCTACGA | TGGAGACCGC | GCTTATAAGC | GCCCCGAGGA | 7105 |
| GAGCCCGCCC | CCAGGTAAGC | GGACCAATGG | CCGATTTTCG | CCGCGGACTT | CCCCGACGGC | 7165 |
| CGGCCAATGG | GATTTTCTC | GCCCGCTTCC | TCTCGCGTCT | GCTTTGCATG | CCCGGCCCAA | 7225 |
| GATGGCGGCC | GCCGGCCAAT | GGGATTTCGC | GAGGAACTTC | CTCGCGAGGA | CCATTTGCAT | 7285 |
| GCCCGGCCCC | CGCGGCGGCC | ATCTTGCCCA | CTCGACGGCC | AATGGGATTT | CTCTCGCCCA | 7345 |
| CTTCCTCTCG | CGTCTACTTT | GCATGTCCGG | CCCCGAGGGC | GCCATCTTGG | CCCCTCGACG | 7405 |
| GCCAATGGGA | TTTCTCTCCC | TACTTCCTCT | CGCGTCTACT | TTGCATGTCC | GGCCCCCGCG | 7465 |
| GCGGCCATCT | CGGCTCGCCC | GGGCCAATGG | CGCGCGGAG | GCGTCTCCCG | CGCGCCTCTG | 7525 |
| ATTTGCATGC | CCGGCCCGCT | CTGCGGCCAT | CTTGGCCGCG | GGCGGCCAAT | GAGATTGTCC | 7585 |
| GAAAATCCCT | CGCGCGGGCG | CGAGGCGCAT | GCTCGGCACG | CGACCCACCC | CCGTGGTGCT | 7645 |
| AGCGAGCCAA | TCAGATGATT | TTCGGGGAAG | CTTCCGTGTG | CACGTCATTT | GCATGCTCGC | 7705 |
| CCCACGTGGC | CGCCCTCGGC | CAATGGGGCC | TCACGGTGCA | AGCTTCCGTG | TGTCTGCACG | 7765 |
| TGGTCCGCAT | GTGTTGTGGT | GGTCTCTGTG | TTGTGTGGTG | GTCTCTGTGT | TGTGTGGTGG | 7825 |
| TCTCTGTGTT | GTGTGGTGGT | CTCTGTGTTG | TGGTGGTC | TCTGTGTTGT | GGTGGTCT | 7885 |
| CTGTGTTGTG | TGGTGGTCTC | TGTGTTGTGT | GGTGGTCTCT | GTGTTGTGTG | GTGGTCTCTG | 7945 |
| TGTTGTGTGG | TGGTCTCTGT | GTTGTGTGGT | GGTATCACCG | CCTCCCCTG | CCACTCGCGA | 8005 |
| GACCCCGAGA | CCCCCGTTTC | CCCCTCCTCG | AGACCCCTGA | GACCCCGAG | ACCCTCCCGC | 8065 |
| GACCCCCGCG | GTCGCCCCAC | CCGCGCCTCG | CGCTCGGCGC | GCGCTCCGAG | GGCGCCCCAG | 8125 |
| CCGGTCGGAG | AGACGAGCGG | AACCGCCGTC | GGACCGGGGA | CCGGCGACCG | GACCCGAACC | 8185 |
| GGGAAGCGAC | GCCGGGGCGG | GAGAACCGGA | CCCGAACCTC | GAGCCCGGAC | CCGCCCGGAC | 8245 |
| CCGGAAGGAA | GGAGCCGGAC | AGCCACGCCT | TGGATACTTT | TGTCGCCCAC | CCACCCCCTC | 8305 |
| CTCTCCCCCA | CCCCTCTATC | TCTCTCTCCC | GGTCCCCCT | CCCACCCCAC | GAGACACGCC | 8365 |
| CCAGAGTGAA | AAAAAAAATA | AAGTTGTTC | TCGTTGCACC | GTCTTCCGGC | TCGTGTCGTC | 8425 |
| CTTCCGCGGT | ACC | | | | | 8438 |

( 2 ) INFORMATION FOR SEQ ID NO:2:

( i ) SEQUENCE CHARACTERISTICS:
        ( A ) LENGTH: 1958 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Arg  Arg  Gly  Pro  Leu  Ala  Gly  Arg  Trp  Arg  Leu  Arg  Ser  Leu
 1              5                        10                       15

Ala  Leu  Gly  Leu  Ser  Ala  Arg  Pro  Ala  Ala  Ser  Gln  Ala  Pro  Gly  Pro
            20                       25                       30

Ser  Leu  Leu  Ala  Pro  Gln  His  Gly  Arg  Pro  Ser  Gly  Pro  Ala  Arg  Gly
        35                       40                       45

Ala  Pro  Gly  Arg  Arg  Pro  Leu  Val  Val  Arg  Gly  Leu  Gly  Gly  Leu  Arg
    50                       55                       60

Gln  Ile  Leu  Arg  Val  His  Pro  Ala  Ala  Arg  Gly  Ala  Arg  Val  Phe  Leu
65                       70                       75                       80
```

```
Val Gly Gly Arg His Leu Arg Val Arg Val Cys Leu Gly Leu Gly Arg
                85                  90                      95
Val Asp Ile Val His Thr Leu Val Ala His Arg Gly Ser Pro Leu His
            100                 105             110
Pro Pro His Pro Leu Arg Arg Tyr Val Lys Gln Arg Ile Asp Glu Gly
        115                 120             125
Val Gly Val Cys Pro Lys His Gly His Gly Leu Gly His Ala Leu
    130             135             140
Ala Val His Pro Val Leu Leu Asp Asn Leu Asp Asp Val Val His Tyr
145             150             155                     160
Gly Leu Ala Asp Gly Val Ala Leu Asp Asp Arg Arg Asp Leu Pro Ile
            165             170             175
Lys Pro Val Glu Asp Gly Asp Ser Gly Ala Gly Ala Arg Pro Arg Pro
            180             185             190
Gly Ala Leu Pro Phe Gly Leu Leu Val Ala His Leu Leu Gly Ile Val
        195             200             205
Phe Thr Pro Asp Asp Arg Glu Ala Pro Pro Tyr Arg Leu Ile Leu Phe
    210             215             220
Pro Val Asp Ile Arg Arg Pro Leu His Gly Arg Leu His Lys Arg Ser
225             230             235                     240
Val Ala Val His Val Val Glu Asp Gly Gly Asp Ala Gly Ile Ala Gln
            245             250             255
Arg Ala Gly Gly Ala Arg Gln Gly Pro Ala Leu Asp Ala Val Gln Thr
            260             265             270
Glu Leu Val His Ala Arg Gln Arg Leu Arg Leu Gly Gly Arg Asp Val
        275             280             285
Gln Ala Asp Gly Ala Val His Asp Gly Pro Pro Ser Ser Asn Ser His
    290             295             300
Pro Gly Pro Pro Gly Pro Ser Gly Pro Ser Thr Ser His Gln Asp Pro
305             310             315                     320
Pro Gly Pro Pro Thr Pro Ser Thr Ser His His His His His Gln
            325             330             335
Gly Pro Pro Thr Ser Pro Arg Pro Ser Thr Ser Ser His Gln Asp Pro
            340             345             350
Pro Gly Gly Gly Pro Pro Ser Ala Glu Thr His His His His His Gln
        355             360             365
Asp Pro Pro Gly Gly Gly Pro Pro Ser Thr Ser Ser His His His His
    370             375             380
Gln Asp Pro Pro Gly Gly Gly Pro Pro Ser Pro Pro Pro Arg Pro Ser
385             390             395                     400
Thr Ser Ser Ser Ser His Gln Gly Pro Pro Ser Thr Arg Pro Pro
            405             410             415
Pro Pro Gln Arg Pro Pro Pro Arg Trp Pro Pro Pro Ser Pro Gln Lys
            420             425             430
Ile Ser Glu Thr Arg Ala Gly Ser Glu Asn Thr Ala Gln Thr Leu Phe
        435             440             445
Ser His Ser Glu Asn Lys Leu Phe Ser His Pro Met Gly Glu Gly Gly
    450             455             460
Glu Gly Asp Arg Gly Thr Ala Gly Gly Glu Gly Asp Arg Asp Asp Pro
465             470             475                     480
Arg Pro Pro Ser Pro Pro Arg Pro Pro Pro Leu Pro Pro Pro
            485             490             495
Pro Pro Pro Pro Pro Pro Pro Gln Pro Pro Ala Gly Gly Ser Ala
            500             505             510
```

-continued

| | | | | | | | | | | | | | | |
|---|---|---|---|---|---|---|---|---|---|---|---|---|---|---|
| Arg | Arg | Arg | Arg | Arg | Gly | Gly | Gly | Gly | Pro | Pro | Gly | Arg | Gly | Gly |
| | 515 | | | | 520 | | | | | | 525 | | | |
| Arg | Arg | Arg | Gly | Gly | Lys | Arg | Arg | Ala | Glu | Gly | Thr | Glu | Ala | Ala |
| | 530 | | | | | 535 | | | | 540 | | | | |
| Ala | Ala | Asp | Ala | Glu | Glu | Glu | Asp | Gly | Asp | Glu | Asp | Glu | Asp | Glu |
| 545 | | | | | 550 | | | | 555 | | | | | 560 |
| Asp | Arg | Ala | Glu | Asp | Glu | Gly | Arg | Glu | Asp | Gly | Gly | Glu | Gly | Pro | Arg |
| | | | | 565 | | | | | 570 | | | | | 575 |
| Gly | Ala | Gly | Gly | Gly | Ala | Gly | Glu | Ser | Glu | Ser | Glu | Ser | Glu | Ser | Ser |
| | | | | 580 | | | | | 585 | | | | | 590 | |
| Arg | Ala | Glu | Gly | Ala | Pro | Arg | Ser | Ala | Glu | Gln | Gln | Val | Gly | Val | Ala |
| | | | 595 | | | | 600 | | | | | 605 | | | |
| Gly | Val | Leu | Gly | Leu | Leu | Val | Val | Arg | Asp | Gly | Leu | His | Leu | Asp | Gly |
| | 610 | | | | | 615 | | | | | 620 | | | | |
| Pro | Glu | Arg | Ala | Ala | Gly | Pro | Ala | Val | Ala | Ala | Ala | Glu | Ala | Asp | Asp |
| 625 | | | | | 630 | | | | | 635 | | | | | 640 |
| Leu | His | Arg | Gly | Arg | Val | Leu | Pro | Val | Leu | Ala | Gly | Pro | Pro | Gly | Ala |
| | | | | 645 | | | | | 650 | | | | | 655 | |
| Arg | Gly | Pro | Val | Gly | Leu | His | Gly | Ala | Ala | Gly | Gly | Gly | Ala | Asp | Ala |
| | | | | 660 | | | | | 665 | | | | | 670 | |
| Gly | Leu | Glu | Gly | Arg | Lys | Val | Pro | Ala | His | Gly | Arg | Arg | Gly | Ala | Arg |
| | | | | 675 | | | | | 680 | | | | | 685 | |
| Gly | Arg | Glu | Gly | Ala | Arg | Gly | Gln | His | Gln | Arg | Gly | Gly | Leu | Gly | Val |
| | | 690 | | | | | 695 | | | | | 700 | | | |
| Gly | Leu | Gln | Gln | Arg | Arg | Gly | Ala | Glu | Gly | Ala | Gln | Leu | Gly | Arg | Gln |
| 705 | | | | | | 710 | | | | | 715 | | | | 720 |
| Ala | Leu | Gly | Ala | Ala | Glu | Leu | Gly | Glu | Ala | Pro | Ala | Ala | Ala | Gly | Asp |
| | | | | 725 | | | | | 730 | | | | | 735 | |
| Glu | Asp | Gly | Pro | Gln | Arg | Gly | Ala | Glu | Pro | Pro | Ala | Val | Gly | Arg | Ala |
| | | | 740 | | | | | 745 | | | | | 750 | | |
| Val | Pro | Glu | Gly | Gly | Ala | Arg | Val | Lys | Val | Arg | Val | Pro | Glu | Pro | Glu |
| | | | 755 | | | | | 760 | | | | | 765 | | |
| Arg | Gly | Ala | Leu | Ala | Gly | His | Val | Leu | Ala | Ala | Val | His | Gly | Gly | Glu |
| | | 770 | | | | | 775 | | | | | 780 | | | |
| His | Ala | Leu | Ala | Val | Gly | Ala | Arg | Arg | Gln | Arg | Asp | Arg | Gly | Pro | Gly |
| 785 | | | | | 790 | | | | | 795 | | | | | 800 |
| Pro | Gly | Ala | Gly | Ala | His | Arg | Val | Ala | His | Val | Val | Leu | Ala | Ala | Glu |
| | | | | 805 | | | | | 810 | | | | | 815 | |
| Ala | Gln | Arg | Leu | Gly | Pro | Gly | Val | Gln | Ala | Gly | Glu | Gly | Gly | Leu | His |
| | | | 820 | | | | | 825 | | | | | 830 | | |
| Ala | Gly | Glu | Ala | Gly | Arg | Ala | His | Asp | Gly | Ala | Arg | Val | Gln | Asp | Gly |
| | | 835 | | | | | 840 | | | | | 845 | | | |
| Arg | Ala | Glu | Leu | Ala | Ala | Leu | Gly | Pro | Ala | His | Gly | Ala | Leu | Gly | Gly |
| | 850 | | | | | 855 | | | | | 860 | | | | |
| Arg | Val | Gln | Ala | Gly | Ala | Asp | Val | Asp | Val | Val | Pro | His | Gly | Arg |
| 865 | | | | | 870 | | | | | 875 | | | | | 880 |
| Ala | Val | Arg | Gly | Pro | Val | Leu | Asp | Gly | Val | Gln | His | Asp | Glu | Pro | Ala |
| | | | | 885 | | | | | 890 | | | | | 895 | |
| Pro | Arg | Arg | Ala | Glu | Pro | Arg | Ala | Glu | Val | Leu | Asp | Gly | Ala | Gly | Glu |
| | | | | 900 | | | | | 905 | | | | | 910 | |
| Ala | Glu | Val | Pro | Arg | Arg | Glu | Gln | Gln | His | Pro | Leu | Gly | Val | Glu | Ala |
| | | | 915 | | | | | 920 | | | | | 925 | | |
| Ala | Asp | Val | Gly | Ala | Pro | Gly | Pro | Val | Pro | Gly | Pro | Gly | Val | Arg | Val |
| | 930 | | | | | 935 | | | | | 940 | | | | |
| Arg | Arg | Ala | Glu | Ala | Val | Gly | Glu | Gly | Gly | Glu | Gln | Arg | Arg | Glu | Ala |

|       | 945 |     |     |     |     | 950 |     |     |     |     | 955 |     |     |     |     | 960 |
|-------|-----|-----|-----|-----|-----|-----|-----|-----|-----|-----|-----|-----|-----|-----|-----|-----|

Ala Ala Ala Arg Val Pro Gly Arg Ala Arg Gly Ala Leu Gly Gly Leu
                    965                 970                 975

Gly Ala Glu Leu Leu Val Gly Gln Arg Val Val Glu His His His Ala
            980                 985                 990

His Val Leu Gly Val Gly Tyr Leu Pro His Pro Gly Gly Ala Ala Ala
            995                 1000                1005

Glu Arg Gly Ala Arg Gly Pro Ala Ala Arg Gly Asp Val Arg Gln Gly
            1010                1015                1020

Gly Arg Val Glu Gly Glu Arg Arg Ala Pro Glu Phe Gly Glu Asp Leu
1025                1030                1035                1040

Leu Val His Glu Gly Ala Gly His Leu Gly Arg Ala Val Gly Gly Glu
                1045                1050                1055

Gly Arg Gly Gly Gly Pro Arg Arg Val Gly Leu Ala Gly Arg Asp Ala
            1060                1065                1070

Ala Glu Ala Ala Val Gly Arg Gly Val Leu Gly His Gly Pro Glu Arg
            1075                1080                1085

Ala Pro Glu Pro Val Val Leu Gly Gly Gly Gly Gly Gly Gly Gly Gly
            1090                1095                1100

His Glu Arg Gly Ser Gly Val Arg Ser Gly Pro Glu Ser Glu Gly Ala
1105                1110                1115                1120

Ala Leu Ala Pro Gly Pro Pro Val Leu Phe Val Val Ala Val Ala Val
                1125                1130                1135

Ala Val Pro Ala Glu Gly Arg Ala Gly Glu Pro Leu Val Leu Leu Ala
            1140                1145                1150

Val Pro Gly Ala Ala Gly Pro Gly Arg Ala Ala Leu Leu Leu Ala Pro
            1155                1160                1165

Leu Gly Arg Trp Val Arg Ala Gly Gly Gly Ala Gly Val Ala Gly
            1170                1175                1180

Gly Ala Gly Glu Ala Gly Leu Gly Ala Gly Ala Gly Leu Gly Ala Gly
1185                1190                1195                1200

Ala Gly Leu Gly Ala Gly Gly Ala Gly Gly Pro Gly Ala Gly Glu Ala
            1205                1210                1215

Gly Gly Gly Ala Arg Arg Arg Arg Arg Arg Arg Trp Asp Asp Glu Ala
            1220                1225                1230

Gly Leu Leu Gly Pro Glu Arg Gly Gln Ala Gly Arg Gly Leu Arg Gly
            1235                1240                1245

Pro Gly Pro Arg Gly Gly Leu Gly Glu Pro Gly Pro Gly His Val Gly
            1250                1255                1260

Arg Gly Glu Glu Gly Arg Gly Val Gly Pro Gly Gly Leu Ala Gly Ala
1265                1270                1275                1280

Gly Pro Val His Ala Val Ala His Gln Arg Arg His Gly Ala Gly Asp
                1285                1290                1295

Glu Gly Asp Arg Val Arg Gly Leu Leu Pro Leu Gly Arg Ala Gly Pro
            1300                1305                1310

Gly Asp Arg Val Ala Glu Arg Glu Gln Arg Gly Gly His Leu Leu Glu
            1315                1320                1325

Ala Gly Gly Pro Glu Gly Gly Arg Gly Ala Gly Gly Arg Gly Gln Pro
            1330                1335                1340

Glu Arg Ala Gly Gln Gln Ala Leu Glu Asp Ala Ala Ala Gly Gln Asp
1345                1350                1355                1360

Ala Gly Val Arg Gln Leu Ala Gly His Ala Ala Gly Leu Arg Gly Gly
            1365                1370                1375

Glu Gly Gly Ala Asp Ala Gly Ala Glu Gly Leu Asp Gly Arg Leu Pro
            1380                1385                1390

-continued

```
Gly Ala Gly Val Arg Gly Ala Ala Arg Val Gly His Val Gly Val Gly
    1395                1400                1405

Pro Ala Glu Ala Leu Gln Asp Glu Gly Leu Leu Gly Ala Ile Val Ala
    1410                1415                1420

Ala Ala His Gly His Gly Ala His Arg Val Arg Gln Gly Pro Glu Arg
1425                1430                1435                1440

Val Leu Gly Gly His Gly Val Pro Asp Val Arg Gln Arg Arg Gly His
                1445                1450                1455

Ala Ala Gly Asp Glu Gly Ala Val Ala Val Gly Arg Val Asp Pro Ala
            1460                1465                1470

Leu Ala Glu Leu Val Glu Ala Leu Val Gly Gly Leu His Pro Arg Val
        1475                1480                1485

Leu Gln Pro Gly His Gly Leu Ala Gly Gly Pro Ala Val Asp Glu Ala
        1490                1495                1500

His Glu Gly Leu Val Leu Leu Pro Arg Val Pro His Leu Arg Asp Glu
1505                1510                1515                1520

Asp Gly His Gly Pro Gly Arg Gly Ala Val Ala Gly Arg Gly Leu Ala
                1525                1530                1535

Asp Val Val Leu Val Pro Glu Pro Leu Ala Gly Val Pro Gly Ala Ala
            1540                1545                1550

Val Ala Asp Ala Ala Val Gly Arg Arg Val Gly Ala Gly Pro Gly Leu
        1555                1560                1565

Pro Glu Arg Gly Glu Gln Arg Pro Val Gly Arg Arg Gly Pro Val Gly
    1570                1575                1580

His Glu Arg Glu Val Val Val Gly Gly Ala Ala Leu Pro Ala Arg Gly
1585                1590                1595                1600

Pro Gly Gly Leu Arg Gly Arg Gly Arg Gly Gly Arg Gly Gly Gly Gly
                1605                1610                1615

Gly Gly Gly Gly Gly Gly Gly Arg Gly Pro Arg Gly Arg Gly Gly Arg
            1620                1625                1630

Arg Arg Arg Arg Trp Arg Pro Gly Ala Gly Glu Trp Gly Ala Gly Pro
        1635                1640                1645

Asp Ser Phe Val Phe Phe Ser Leu Gly Gly Gly Arg Gly Arg Gly Gly
    1650                1655                1660

Arg Gly Gly Arg Gly Arg Gly Gly Gly Arg Ala Pro Arg Gly Gly Gly
1665                1670                1675                1680

Gly Gly Gly Gly Gly Pro Gly Gly Gly Gly Arg Ala Gly Arg Gly Glu
                1685                1690                1695

Val Arg Val Ala Ala Ala Ala Ala Gly Ala Ala Glu Ala Ala Ala Ala
            1700                1705                1710

Ala Glu Gly Ala Leu Ser Gly Ala Ala Pro Ala Gly Leu Ser Leu Gln
        1715                1720                1725

Gly Arg Pro Ala Val Pro Gly Glu Ala Glu Ser Val Leu Val Leu Leu
        1730                1735                1740

Gly Ala Ala Gly Asp Gly Leu Asp Gly Asp Gly Gly Gly Ala Gly
1745                1750                1755                1760

Ala Gly Val Gly Val Gly Gly Asp Gly Ala Pro Gly Ala Lys Arg Pro
                1765                1770                1775

Arg Ile Glu Pro Pro Arg Gly Gly Gly Leu Val Glu Gln Gly Leu Ala
            1780                1785                1790

Val Leu Val Met Val Thr Thr Ala Val Pro Ser Ala Gly Gly Gly Ala
        1795                1800                1805

Ala Ala Ala Gly Arg Arg Asp Arg Pro Gly Gly Gly Gly Gly Trp Gly
    1810                1815                1820
```

-continued

```
Ser  Gly  Pro  Pro  Pro  Cys  Arg  Arg  Cys  Gly  His  Arg  Cys  Trp  Leu  Cys
1825                1830                1835                1840

Trp  Trp  Arg  Arg  Gly  Pro  Arg  Pro  Arg  Arg  Arg  Pro  Gly  Leu  Thr  Asp
               1845                1850                1855

Arg  Val  Pro  Pro  Arg  Gly  Gly  Pro  Ser  Pro  Arg  Gly  Arg  Arg  Gly  Ala
               1860                1865                1870

Gly  Gly  Ala  Gly  Gly  Ala  Gly  Gly  Ala  Gly  Gly  Gly  Gly  Gly  Arg  Gly
          1875                1880                1885

Gly  Cys  Gly  Gly  Gly  Arg  Ala  Pro  Gly  Ala  Ala  Gly  Gly  Pro  Gly  Leu
          1890                1895                1900

Cys  Arg  Cys  Glu  Cys  Cys  Arg  Gly  Arg  Arg  Pro  Gly  Pro  Gly  Ala  Gly
1905                1910                1915                1920

Pro  Gly  Pro  Gly  Pro  Glu  Asp  Glu  Val  Thr  Val  Leu  Gly  Ala  Leu  Met
                    1925                1930                1935

Glu  Ser  Pro  Thr  Gly  Gly  Pro  Gly  Gly  Arg  Gly  Pro  Gly  Leu  Val  Leu
               1940                1945                1950

Leu  Leu  Val  Phe  Val  Val
               1955
```

( 2 ) INFORMATION FOR SEQ ID NO:3:

( i ) SEQUENCE CHARACTERISTICS:
       ( A ) LENGTH: 1683 base pairs
       ( B ) TYPE: nucleic acid
       ( C ) STRANDEDNESS: double
       ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
       ( A ) ORGANISM: Pseudorabies virus ( i x ) FEATURE:
       ( A ) NAME/KEY: CDS
       ( B ) LOCATION: 211..1440
       ( D ) OTHER INFORMATION: /product="early protein 0"

( x i ) SEQUENCE DESCRIPTION: SEQ ID NO:3:

```
GGATCCGCAG  CGCCGCTTTC  AGACCCAGGA  GCCGTCGACC  CACCGCGGGA  GGGCCCGCTT      60

CCCACGACGG  CGCGCCCGGG  CCATCGTCCC  GGGACGGCCC  GAGGGGGCGG  GGGGAGCCCC     120

GACGGGGCGG  GCGGAAGGGG  GCGTGGACGC  CCCGGGCGAA  GACAAACAAA  GGGGCCGGGC     180

ACCCGGTTAA  AAAACGGGGC  CCTCGACACC  ATG  GGC  TGC  ACG  GTC  TCT  CGG  AGA     234
                                    Met  Gly  Cys  Thr  Val  Ser  Arg  Arg
                                     1                 5

CGG  ACG  ACC  ACC  GCC  GAG  GCT  TCC  AGC  GCC  TGG  GGG  ATC  TTT  GGC  TTC     282
Arg  Thr  Thr  Thr  Ala  Glu  Ala  Ser  Ser  Ala  Trp  Gly  Ile  Phe  Gly  Phe
     10                  15                  20

TAC  CGC  CCC  AGA  AGC  CCC  TCG  CCA  CCG  CCG  CAG  CGC  CTG  TCA  CTG  CCA     330
Tyr  Arg  Pro  Arg  Ser  Pro  Ser  Pro  Pro  Pro  Gln  Arg  Leu  Ser  Leu  Pro
 25                  30                  35                  40

CTC  ACC  GTC  ATG  GAC  TGC  CCC  ATC  TGC  CTG  GAC  GTC  GCG  GCC  ACC  GAG     378
Leu  Thr  Val  Met  Asp  Cys  Pro  Ile  Cys  Leu  Asp  Val  Ala  Ala  Thr  Glu
               45                  50                  55

GCG  CAG  ACG  CTG  CCG  TGC  ATG  CAC  AAG  TTC  TGT  CTG  GAC  TGC  ATC  CAG     426
Ala  Gln  Thr  Leu  Pro  Cys  Met  His  Lys  Phe  Cys  Leu  Asp  Cys  Ile  Gln
          60                  65                  70

CGC  TGG  ACC  CTG  ACG  AGC  ACC  GCC  TGC  CCG  CTG  TGC  AAT  GCC  CGC  GTC     474
Arg  Trp  Thr  Leu  Thr  Ser  Thr  Ala  Cys  Pro  Leu  Cys  Asn  Ala  Arg  Val
     75                  80                  85
```

| | | | | | | | | | | | | | | | | |
|---|---|---|---|---|---|---|---|---|---|---|---|---|---|---|---|---|
| ACC | TCC | ATC | CTC | CAC | CAC | GTG | GAC | AGC | GAC | GCT | TCG | TTT | GTG | GAG | ACG | 522 |
| Thr | Ser | Ile | Leu | His | His | Val | Asp | Ser | Asp | Ala | Ser | Phe | Val | Glu | Thr | |
| | 90 | | | | 95 | | | | 100 | | | | | | | |

| | | | | | | | | | | | | | | | | |
|---|---|---|---|---|---|---|---|---|---|---|---|---|---|---|---|---|
| CCC | GTG | GAG | GGG | GCG | ACG | GAT | GTC | GAC | GGG | GAA | GAG | GAT | GAG | CCG | GTA | 570 |
| Pro | Val | Glu | Gly | Ala | Thr | Asp | Val | Asp | Gly | Glu | Glu | Asp | Glu | Pro | Val | |
| 105 | | | | | 110 | | | | | 115 | | | | | 120 | |

| | | | | | | | | | | | | | | | | |
|---|---|---|---|---|---|---|---|---|---|---|---|---|---|---|---|---|
| GGG | GGG | GGC | TTC | GCG | GTC | ATC | TGG | GGT | GAA | GAC | TAT | ACC | GAG | GAG | GTG | 618 |
| Gly | Gly | Gly | Phe | Ala | Val | Ile | Trp | Gly | Glu | Asp | Tyr | Thr | Glu | Glu | Val | |
| | | | | 125 | | | | | 130 | | | | | 135 | | |

| | | | | | | | | | | | | | | | | |
|---|---|---|---|---|---|---|---|---|---|---|---|---|---|---|---|---|
| CGC | CAC | GAG | GAG | GCC | GAA | GGG | CAG | GGC | TCC | GGG | TCT | GGG | TCT | CGC | GCC | 666 |
| Arg | His | Glu | Glu | Ala | Glu | Gly | Gln | Gly | Ser | Gly | Ser | Gly | Ser | Arg | Ala | |
| | | | 140 | | | | | 145 | | | | | 150 | | | |

| | | | | | | | | | | | | | | | | |
|---|---|---|---|---|---|---|---|---|---|---|---|---|---|---|---|---|
| CGC | CCC | AGA | GTC | CCC | GTC | TTC | AAC | TGG | CTT | TAT | GGG | CAG | GTC | TCG | ACG | 714 |
| Arg | Pro | Arg | Val | Pro | Val | Phe | Asn | Trp | Leu | Tyr | Gly | Gln | Val | Ser | Thr | |
| | | 155 | | | | | 160 | | | | | 165 | | | | |

| | | | | | | | | | | | | | | | | |
|---|---|---|---|---|---|---|---|---|---|---|---|---|---|---|---|---|
| GTC | ATC | GAG | AGC | GAC | CCC | ATC | CGC | GAG | GCC | GTA | GTG | GAC | AAC | ATC | GTC | 762 |
| Val | Ile | Glu | Ser | Asp | Pro | Ile | Arg | Glu | Ala | Val | Val | Asp | Asn | Ile | Val | |
| | 170 | | | | | 175 | | | | | 180 | | | | | |

| | | | | | | | | | | | | | | | | |
|---|---|---|---|---|---|---|---|---|---|---|---|---|---|---|---|---|
| GAG | ATT | ATC | CAG | GAG | CAC | GGG | ATG | AAC | CGC | CAG | CGC | GTG | ACC | GAG | GCC | 810 |
| Glu | Ile | Ile | Gln | Glu | His | Gly | Met | Asn | Arg | Gln | Arg | Val | Thr | Glu | Ala | |
| 185 | | | | | 190 | | | | | 195 | | | | | 200 | |

| | | | | | | | | | | | | | | | | |
|---|---|---|---|---|---|---|---|---|---|---|---|---|---|---|---|---|
| ATG | CTC | CCC | ATG | TTT | GGG | GCA | AAC | ACC | CAC | GCC | CTC | GTC | GAT | ACG | CTG | 858 |
| Met | Leu | Pro | Met | Phe | Gly | Ala | Asn | Thr | His | Ala | Leu | Val | Asp | Thr | Leu | |
| | | | | 205 | | | | | 210 | | | | | 215 | | |

| | | | | | | | | | | | | | | | | |
|---|---|---|---|---|---|---|---|---|---|---|---|---|---|---|---|---|
| TTT | GAC | ATA | TCG | GCG | CAG | TGG | ATG | CGG | CGG | ATG | CAG | AGG | CGA | GCC | CCG | 906 |
| Phe | Asp | Ile | Ser | Ala | Gln | Trp | Met | Arg | Arg | Met | Gln | Arg | Arg | Ala | Pro | |
| | | | 220 | | | | | 225 | | | | | 230 | | | |

| | | | | | | | | | | | | | | | | |
|---|---|---|---|---|---|---|---|---|---|---|---|---|---|---|---|---|
| ATG | AGC | CAC | CAG | GGT | GTG | AAC | TAT | ATC | GAC | ACG | TCC | GAG | TCC | GAG | GCA | 954 |
| Met | Ser | His | Gln | Gly | Val | Asn | Tyr | Ile | Asp | Thr | Ser | Glu | Ser | Glu | Ala | |
| | | 235 | | | | | 240 | | | | | 245 | | | | |

| | | | | | | | | | | | | | | | | |
|---|---|---|---|---|---|---|---|---|---|---|---|---|---|---|---|---|
| CAC | TCT | GAC | TCT | GAG | GTG | TCT | TCC | CCC | GAC | GAG | GAA | GAC | TCG | GGC | GCC | 1002 |
| His | Ser | Asp | Ser | Glu | Val | Ser | Ser | Pro | Asp | Glu | Glu | Asp | Ser | Gly | Ala | |
| | 250 | | | | | 255 | | | | | 260 | | | | | |

| | | | | | | | | | | | | | | | | |
|---|---|---|---|---|---|---|---|---|---|---|---|---|---|---|---|---|
| TCG | AGC | AGC | GGG | GTG | CAC | ACG | GAG | GAT | CTG | ACG | GAG | GCC | TCC | GAG | TCC | 1050 |
| Ser | Ser | Ser | Gly | Val | His | Thr | Glu | Asp | Leu | Thr | Glu | Ala | Ser | Glu | Ser | |
| 265 | | | | | 270 | | | | | 275 | | | | | 280 | |

| | | | | | | | | | | | | | | | | |
|---|---|---|---|---|---|---|---|---|---|---|---|---|---|---|---|---|
| GCG | GAC | GAC | CAG | AGG | CCG | GCG | CCC | AGG | CGC | TCC | CCG | CGC | AGG | GCC | CGA | 1098 |
| Ala | Asp | Asp | Gln | Arg | Pro | Ala | Pro | Arg | Arg | Ser | Pro | Arg | Arg | Ala | Arg | |
| | | | | 285 | | | | | 290 | | | | | 295 | | |

| | | | | | | | | | | | | | | | | |
|---|---|---|---|---|---|---|---|---|---|---|---|---|---|---|---|---|
| CGG | GCG | GCC | GTG | CTG | AGG | CGC | GAG | CAG | AGA | CGG | ACC | CGG | TGC | CTG | CGA | 1146 |
| Arg | Ala | Ala | Val | Leu | Arg | Arg | Glu | Gln | Arg | Arg | Thr | Arg | Cys | Leu | Arg | |
| | | | 300 | | | | | 305 | | | | | 310 | | | |

| | | | | | | | | | | | | | | | | |
|---|---|---|---|---|---|---|---|---|---|---|---|---|---|---|---|---|
| CGC | GGC | CGG | ACG | GGC | GGA | CAG | GCC | CAG | GGC | GAG | ACT | CCG | GAG | GCG | CCA | 1194 |
| Arg | Gly | Arg | Thr | Gly | Gly | Gln | Ala | Gln | Gly | Glu | Thr | Pro | Glu | Ala | Pro | |
| | | | 315 | | | | | 320 | | | | | 325 | | | |

| | | | | | | | | | | | | | | | | |
|---|---|---|---|---|---|---|---|---|---|---|---|---|---|---|---|---|
| TCG | TCC | GGC | GAG | GGG | TCC | TCT | GCG | CAG | CAT | GGT | GCC | TCG | GGG | GCC | GGG | 1242 |
| Ser | Ser | Gly | Glu | Gly | Ser | Ser | Ala | Gln | His | Gly | Ala | Ser | Gly | Ala | Gly | |
| | 330 | | | | | 335 | | | | | 340 | | | | | |

| | | | | | | | | | | | | | | | | |
|---|---|---|---|---|---|---|---|---|---|---|---|---|---|---|---|---|
| GCC | GGC | CCG | GGG | TCG | GCG | AAC | ACC | GCC | GCT | TCG | GCT | CGC | TCC | TCC | CCC | 1290 |
| Ala | Gly | Pro | Gly | Ser | Ala | Asn | Thr | Ala | Ala | Ser | Ala | Arg | Ser | Ser | Pro | |
| 345 | | | | | 350 | | | | | 355 | | | | | 360 | |

| | | | | | | | | | | | | | | | | |
|---|---|---|---|---|---|---|---|---|---|---|---|---|---|---|---|---|
| TCG | TCT | TCA | CCC | TCC | TCC | TCG | ATG | CGG | CGC | CCG | TCG | CCC | TCT | GCC | TCT | 1338 |
| Ser | Ser | Ser | Pro | Ser | Ser | Ser | Met | Arg | Arg | Pro | Ser | Pro | Ser | Ala | Ser | |
| | | | | 365 | | | | | 370 | | | | | 375 | | |

| | | | | | | | | | | | | | | | | |
|---|---|---|---|---|---|---|---|---|---|---|---|---|---|---|---|---|
| GCC | CCC | GAG | ACC | GCC | GCC | CCC | CGG | GGC | GGG | CCT | CCG | GCG | TCT | AGC | TCG | 1386 |
| Ala | Pro | Glu | Thr | Ala | Ala | Pro | Arg | Gly | Gly | Pro | Pro | Ala | Ser | Ser | Ser | |
| | | | 380 | | | | | 385 | | | | | 390 | | | |

| | | | | | | | | | | | | | | | | |
|---|---|---|---|---|---|---|---|---|---|---|---|---|---|---|---|---|
| TCG | GGA | TCC | CCC | CGC | TCC | GCT | ACC | ATC | TTC | ATC | GAC | CTC | ACC | CAG | GAC | 1434 |
| Ser | Gly | Ser | Pro | Arg | Ser | Ala | Thr | Ile | Phe | Ile | Asp | Leu | Thr | Gln | Asp | |
| | | 395 | | | | | 400 | | | | | 405 | | | | |

| | | | | | |
|---|---|---|---|---|---|
| GAC | GAC | TGAGCTCCCT | CTTCCTCGCC | GCGGACTGGG | GCGACCCTGT TGCTGCTGCG | 1490 |

Asp Asp
410

| GCCGCCGCCG | CTCCTGCCCC | CACTTCGGCT | CCCGCTCCTG | CTCCTGCTCC | CGGCCCCACT | 1550 |
| CCTGTTCCTG | TTCCTGTTCC | TGTTCCTGTT | CCTGTTCCCG | GTCCTGCTCC | GGCTCCCGGC | 1610 |
| CCCGCACCCA | CCTCCGCTCC | TGCTGCGGGT | CTCCAGGCCC | AGACAAAATA | AAAAAGATA | 1670 |
| TATTTTTTCA | GTC | | | | | 1683 |

(2) INFORMATION FOR SEQ ID NO:4:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Cys Thr Val Ser Arg Arg Arg Thr Thr Ala Glu Ala Ser
  1               5                  10                 15

Ser Ala Trp Gly Ile Phe Gly Phe Tyr Arg Pro Arg Ser Pro Ser Pro
                 20                 25                 30

Pro Pro Gln Arg Leu Ser Leu Pro Leu Thr Val Met Asp Cys Pro Ile
              35                 40                 45

Cys Leu Asp Val Ala Ala Thr Glu Ala Gln Thr Leu Pro Cys Met His
      50                 55                 60

Lys Phe Cys Leu Asp Cys Ile Gln Arg Trp Thr Leu Thr Ser Thr Ala
 65                 70                 75                 80

Cys Pro Leu Cys Asn Ala Arg Val Thr Ser Ile Leu His His Val Asp
                 85                 90                 95

Ser Asp Ala Ser Phe Val Glu Thr Pro Val Glu Gly Ala Thr Asp Val
                100                105                110

Asp Gly Glu Glu Asp Glu Pro Val Gly Gly Gly Phe Ala Val Ile Trp
              115                120                125

Gly Glu Asp Tyr Thr Glu Glu Val Arg His Glu Gly Ala Glu Gly Gln
130                135                140

Gly Ser Gly Ser Gly Ser Arg Ala Arg Pro Arg Val Pro Val Phe Asn
145                150                155                160

Trp Leu Tyr Gly Gln Val Ser Thr Val Ile Glu Ser Asp Pro Ile Arg
                 165                170                175

Glu Ala Val Val Asp Asn Ile Val Glu Ile Ile Gln Glu His Gly Met
              180                185                190

Asn Arg Gln Arg Val Thr Glu Ala Met Leu Pro Met Phe Gly Ala Asn
              195                200                205

Thr His Ala Leu Val Asp Thr Leu Phe Asp Ile Ser Ala Gln Trp Met
210                215                220

Arg Arg Met Gln Arg Arg Ala Pro Met Ser His Gln Gly Val Asn Tyr
225                230                235                240

Ile Asp Thr Ser Glu Ser Glu Ala His Ser Asp Ser Glu Val Ser Ser
                 245                250                255

Pro Asp Glu Glu Asp Ser Gly Ala Ser Ser Ser Gly Val His Thr Glu
              260                265                270

Asp Leu Thr Glu Ala Ser Glu Ser Ala Asp Asp Gln Arg Pro Ala Pro
      275                280                285

Arg Arg Ser Pro Arg Arg Ala Arg Ala Ala Val Leu Arg Arg Glu
290                295                300

Gln Arg Arg Thr Arg Cys Leu Arg Arg Gly Arg Thr Gly Gly Gln Ala
305                310                315                320
```

```
Gln  Gly  Glu  Thr  Pro  Glu  Ala  Pro  Ser  Ser  Gly  Glu  Gly  Ser  Ser  Ala
                    325                      330                    335

Gln  His  Gly  Ala  Ser  Gly  Ala  Gly  Ala  Gly  Pro  Gly  Ser  Ala  Asn  Thr
               340                      345                    350

Ala  Ala  Ser  Ala  Arg  Ser  Ser  Pro  Ser  Ser  Ser  Pro  Ser  Ser  Ser  Met
          355                      360                    365

Arg  Arg  Pro  Ser  Pro  Ser  Ala  Ser  Ala  Pro  Glu  Thr  Ala  Ala  Pro  Arg
     370                      375                    380

Gly  Gly  Pro  Pro  Ala  Ser  Ser  Ser  Gly  Ser  Pro  Arg  Ser  Ala  Thr
385                      390                    395                         400

Ile  Phe  Ile  Asp  Leu  Thr  Gln  Asp  Asp  Asp
                    405                      410
```

( 2 ) INFORMATION FOR SEQ ID NO:5:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Pseudorabies virus ( x i ) SEQUENCE DESCRIPTION: SEQ ID NO:5:

```
Leu  Thr  Val  Met  Asp  Cys  Pro  Ile  Cys  Leu  Asp  Val  Ala  Ala  Thr  Glu
1                   5                        10                       15

Ala  Gln  Thr  Leu  Pro  Cys  Met  His  Lys  Phe  Cys  Leu  Asp  Cys  Ile  Gln
          20                      25                        30

Arg  Trp  Thr  Leu  Thr  Ser  Thr  Ala  Cys  Pro  Leu  Cys  Lys  Ala  Arg  Val
          35                      40                        45

Thr  Ser  Ile  Leu  His  His  Val  Asp  Ser  Asp  Ala  Ser  Phe  Val  Glu  Thr
     50                      55                        60

Pro  Val  Glu
65
```

( 2 ) INFORMATION FOR SEQ ID NO:6:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Herpes simplex virus ( x i ) SEQUENCE DESCRIPTION: SEQ ID NO:6:

```
Asp  Glu  Gly  Asp  Val  Cys  Ala  Val  Cys  Thr  Asp  Glu  Ile  Ala  Pro  His
1                   5                        10                       15

Leu  Arg  Cys  Asp  Thr  Phe  Pro  Cys  Met  His  Arg  Phe  Cys  Ile  Pro  Cys
          20                      25                        30

Met  Lys  Thr  Trp  Met  Gln  Leu  Arg  Asn  Thr  Cys  Pro  Leu  Cys  Asn  Ala
          35                      40                        45

Lys  Leu  Val  Tyr  Leu  Ile  Val  Gly  Val  Thr  Pro  Ser  Gly  Ser  Phe  Ser
     50                      55                        60
```

```
        Thr   Ile   Pro   Ile   Val
         65
```

( 2 ) INFORMATION FOR SEQ ID NO:7:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Varicella-zoster virus ( x i ) SEQUENCE DESCRIPTION: SEQ ID NO:7:

```
Ala   Ser   Asp   Asn   Thr   Cys   Thr   Ile   Cys   Met   Ser   Thr   Val   Ser   Asp   Leu
 1                       5                             10                                 15

Gly   Lys   Thr   Met   Pro   Cys   Leu   His   Asp   Phe   Cys   Phe   Val   Cys   Ile   Arg
            20                              25                              30

Ala   Trp   Thr   Ser   Thr   Ser   Val   Gln   Cys   Pro   Leu   Cys   Arg   Cys   Pro   Val
             35                         40                         45

Gln   Ser   Ile   Leu   His   Lys   Ile   Val   Ser   Asp   Thr   Ser   Tyr   Lys   Glu   Tyr
       50                         55                         60

Glu   Val   His
 65
```